(12) United States Patent
Kamino et al.

(10) Patent No.: US 8,134,017 B1
(45) Date of Patent: Mar. 13, 2012

(54) COMPOUND AND USE THEREOF

(75) Inventors: Shinichiro Kamino, Hyogo (JP);
Shuichi Enomoto, Hyogo (JP)

(73) Assignee: Riken, Wako-shi, Saitama (JP)

( * ) Notice: Subject to any disclaimer, the term of this patent is extended or adjusted under 35 U.S.C. 154(b) by 0 days.

(21) Appl. No.: 12/958,504

(22) Filed: Dec. 2, 2010

(51) Int. Cl.
*C07D 491/22* (2006.01)
*C07D 493/04* (2006.01)
*C07D 493/22* (2006.01)
*A61K 31/35* (2006.01)

(52) U.S. Cl. ......... 549/382; 549/224; 424/9.6; 436/800; 514/278; 514/279; 514/453; 546/15; 546/28; 546/36; 548/409; 548/410

(58) Field of Classification Search .................. 549/224, 549/382; 546/15, 28, 36; 548/409, 410; 424/9.6; 436/800; 514/278, 279, 453
See application file for complete search history.

(56) References Cited

OTHER PUBLICATIONS

Hong, Y., et al., "Aggregation-induced emission: phenomenon, mechanism and applications", Chem. Commun. (2009). pp. 4332-4353.
Kamino, S., et al., "Design and synthesis of regioisomerically pure unsymmetrical xanthenes derivatives for staining live cells and their photochemical properties", Bioorganic & Medicinal Chemistry Letters (2008), 18, pp. 4380-4384.
Kamino, S., et al., "A new class of rhodamine luminophores: design, syntheses and aggregation-induced emission enhancement", Chem. Commune. Dec. 21, 2010, 46, pp. 9013-9015.

*Primary Examiner* — Bernard Dentz
(74) *Attorney, Agent, or Firm* — Casimir Jones SC

(57) ABSTRACT

A compound represented by the following formula (1) or (2):

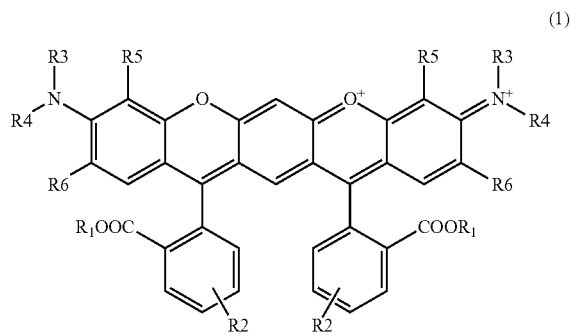

(1)

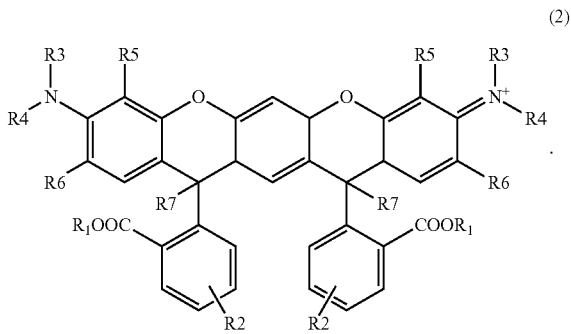

(2)

20 Claims, 34 Drawing Sheets

ABPX01: $R^1 = -C_2H_5$,
ABPX02: $R^1 = -C_3H_7$,
ABPX03: $R^1 = -C_4H_9$,
ABPX04: $R^1 = -C_6H_{13}$.
(a) $CH_3SO_3H$, 95°C, 2hrs.

(a) ABPX01$^+$      (b) ABPX01$^0$ (c) ABPX01$^\pm$

COMPOUND AND USE THEREOF

TECHNICAL FIELD

The present invention relates to a novel compound and use thereof. Particularly, the present invention relates to (a) an aminobenzopyro-xanthene dye, which is a novel pi-electron-extension type rhodamine compound having an aggregation-induced emission characteristic (aggregation-induced emission enhancement; AIEE), (b) a production method for producing the dye, and (c) a technique for using the dye.

BACKGROUND ART

Functional dyes are compounds having various characteristics such as a light-emitting property, photoconductivity, light absorptivity, an energy conversion property, and the like. It is expected that, through the use of such physical properties and reactivity, the functional dyes be applied to cutting-edge fields such as electronics, photonics, and molecular imaging, in particular, information recording that responds to external light, heat, pressure, electric field, and the like, information display, energy conversion, medical diagnosing, agricultural and gardening fields, and the like.

Rhodamine dyes, which are one of the most famous functional dyes, are pi-electron organic dyes having characteristics of: (1) emitting fluorescence in a long-wavelength region; (2) having a high fluorescence quantum yield; (3) having a high water-solubility; and (4) having a high resistance to photobleaching. The rhodamine dyes are widely used as fluorescent probes in molecular biology, and widely used in dye-sensitized solar cells, dye lasers and the like, through the use of these characteristics.

However, the rhodamine dyes tend to form aggregates when the rhodamine dye are dissolved in a solution in high concentration or doped on solids. When forming aggregates, the rhodamine dyes form dimers and cause a π-π stacking. At this time, hydrophobic sites of luminophores in molecules overlap each other face-to-face and form non-emission H-type aggregates. As such, the rhodamine dyes have a problem that due to aggregation under the high-concentration condition, luminous efficiency, color development, photosensitivity, and photosensitization are decreased. Note that, the decrease in the functionality due to the aggregation is a phenomenon that conventional organic functional dyes exhibit, and occurs regardless of whether the functional dyes are rhodamine dyes or not. This phenomenon is the largest factor that limits an applicable range of the functional dyes.

In view of the above problems, Tang and others have reported that a Silole compound exhibits AIEE, i.e., emits light when forming aggregates (Y. Hong, J. W. Y. Lam and B. Z. Tang, Chem. Commun., 4332-4353 (2009)). According to the report of Tang and others, various derivatives are produced. However, these compounds still exhibit low fluorescence quantum yield. That is, no pi-electron AIEE molecule having a high luminous efficiency has been developed so far.

SUMMARY OF INVENTION

Recent studies related to rhodamine dyes are carried out focusing on preventing the π-π stacking between molecules by introducing bulky substituents into a luminophore moiety and increasing hydrophilicity of the molecules. However, the aggregation of dye molecules is an important phenomenon of "photo-switching" of the on-off luminescent states. In view of this, inventors of the present invention think it undesirable to prevent the aggregation.

The present invention is accomplished in view of the above problems. An object of the present invention is to provide (a) a novel compound exhibiting AIEE and having a high luminous efficiency and (b) a technique of using the novel compound. The present invention is more specifically as follows.

A compound of the present invention is a compound represented by the following formula (1) or (2):

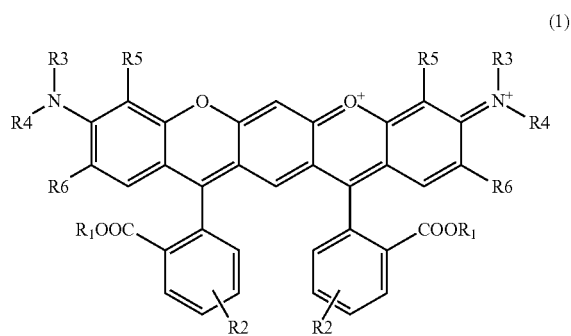

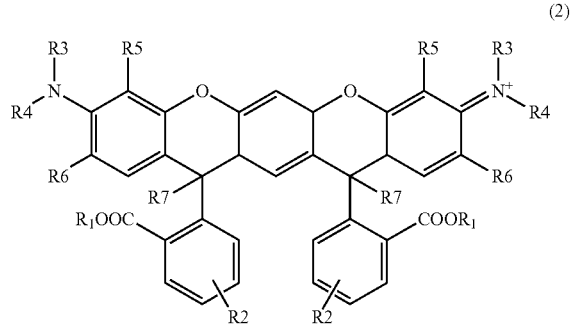

wherein in the formulae (1) and (2), each R1 independently represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; each R2 independently represents a C1 to C8 alkyl group (which may have a nitrogen atom, an oxygen atom, or a sulfur atom as a heteroatom), a halogen atom, a nitro group, a carboxyl group, an amino group, or a hydrogen atom; each R3 and each R4 independently represent a C1 to C8 alkyl group (which may have a nitrogen atom, an oxygen atom, or a sulfur atom as a heteroatom), an allyl group, an aryl group, or a hydrogen atom; each R5 and each R6 independently represent a C1 to C8 alkyl group (which may have a nitrogen atom, an oxygen atom, or a sulfur atom as a heteroatom), an allyl group, a halogen atom, or a hydrogen atom; and R3 and R5, and/or R4 and R6 may be bound to each other to form a ring, and in the formula (2), each R7 independently represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; and R1 and R7 may be bound to each other to form a ring.

A production method of a compound, according to the present invention, is a method for producing a compound, and includes the step of carrying out a condensation process of condensing 2 equivalents of a benzophenone derivative and 1 equivalent of resorcinol in the presence of Lewis acid.

The compound of the present invention exhibits AIEE and has a high luminous efficiency. Especially, the compound of the present invention can solve the following problems that existing organic dyes generally have, such as a quenching effect and a decrease in photosensitivity and photosensitization, which are attributed to aggregation of dyes in solution. In view of this, the compound of the present invention is expected to be applied in various fields such as a fluorescence imaging field, a medical field, and an environment/energy field.

Moreover, with the use of the method of the present invention for producing a compound, it is possible to easily produce an aminobenzopyro-xanthene dye which exhibits AIEE and which has a high luminous efficiency.

Additional objects, features, and strengths of the present invention will be made clear by the description below. Further, the advantages of the present invention will be evident from the following explanation in reference to the drawings.

DESCRIPTION OF EMBODIMENTS

Figure 1:
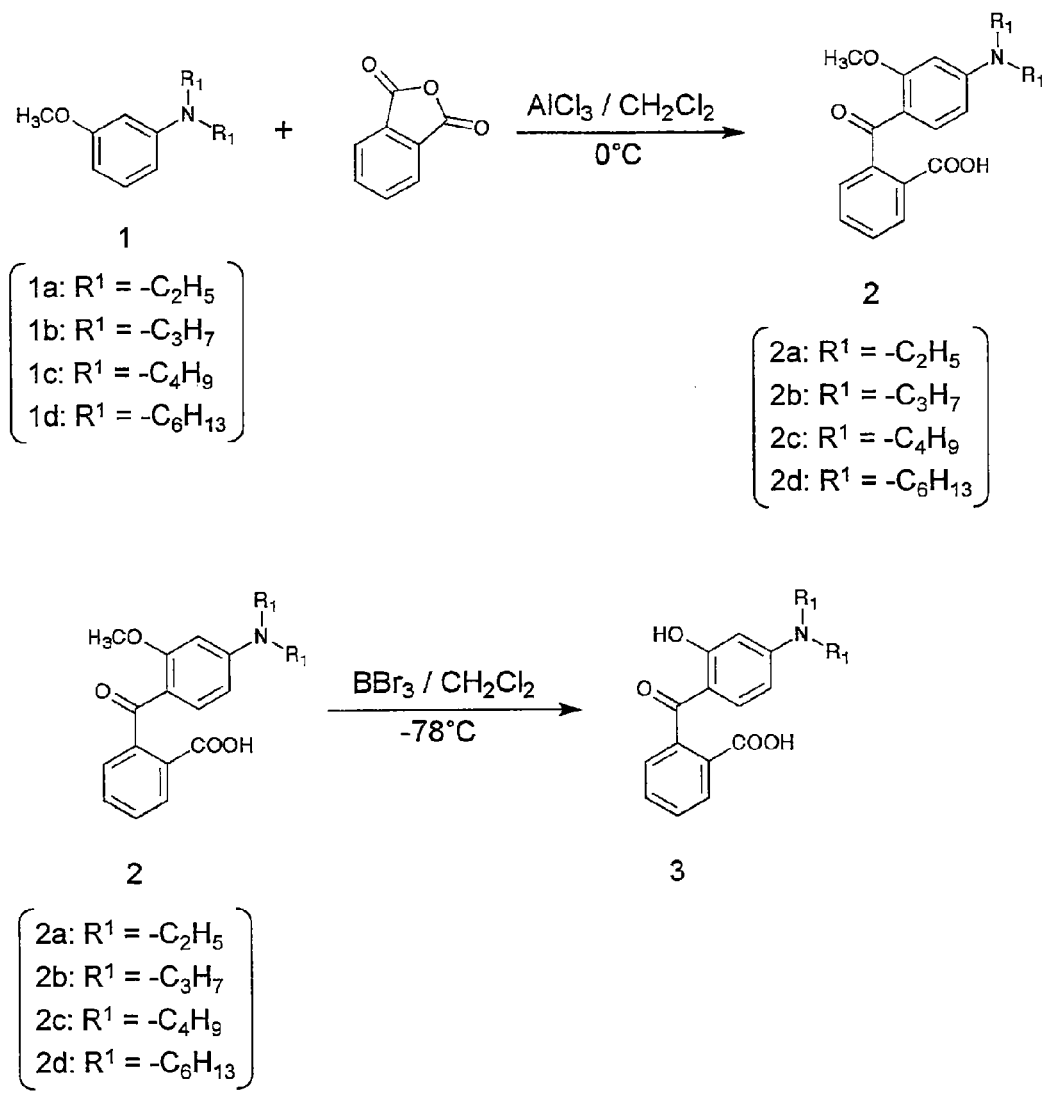
FIG. 1 illustrates a synthetic route for benzophenone derivatives.

The following describes an embodiment of the present invention. Professional Literatures and Patent Literatures described in the Description are all referred to as references in the Description. In the Description, a wording "A to B" indicating a range of values means "not less than A but not more than B", if not otherwise specified. Further, a term "protein" is used as an alternate term of "peptide" or "polypeptide". A term "nucleotide" is used as an alternate term of "polynucleotide", "gene", "nucleic acid", "nucleic acid molecule", "DNA", or "RNA". Further, terms "fluorescence" and "(light) emission" are used synonymously, if not otherwise specified.

<1. Novel Compound>

Effects of intermolecular interactions on emission changes of dye molecules are assumed to be correlated with aggregation morphology, such as H-type (non-emission) aggregation or J-type (emission) aggregation. However, there has been no report of rhodamine dyes having a characteristic of aggregation-induced emission enhancement (AIEE). In view of this, the inventors of the present invention designed pi-electron-extension type molecules having the AIEE characteristic, on the basis of their novel and unique concepts.

The concepts of the inventors are such that (i) the skeleton of a molecule is a rhodamine dye, (ii) an allyl moiety in the molecule is extended and a pi-conjugation of a luminophore moiety is extended as compared with that of conventional rhodamine dyes, and (iii) the luminophore moiety is sandwiched between o-carboxylic acids in benzene moieties in the molecule (luminophore sandwiching structure). In accordance with the concept (ii), the elongated luminophore moiety in a monomeric form is greatly distorted, with the result that no fluorescence is yielded. In the meant time, in accordance with the concept (iii), steric hindrance is caused because the o-carboxylic acids of benzene moieties come close to proximate hydrogens of the luminophore moiety. The steric hindrance disturbs nonradiative deactivation derived from intramolecular rotation and prevents intermolecular π-π stacking. In the aggregation states, J-type aggregation (edge-to-edge direction) is given priority due to the steric hindrance, and the luminophore moiety is partially planarized. As a result, intra-rigidification and planarization of the luminophore are promoted. These result in fluorescence emission enhancement. That is, a novel compound produced on the basis of these concepts has characteristics as follows: when the novel compound is dissolved in a solution at a low concentration and is present in the solution as a monomer, an yield of fluorescence is decreased because the novel compound is structurally distorted. However, when the concentration of the compound in the solution becomes high and the novel compound forms aggregates, intra-rigidification and planarization are increased, thereby reducing structural distortion and yielding fluorescence.

As a result of diligent study, the inventors of the present invention successfully developed a novel pi-electron-extension type rhodamine compound exhibiting AIEE, based on the aforementioned novel and unique concepts. The compound included in the present invention is a novel compound called aminobenzopyro-xanthene dye, and is represented by the following formulae (1) or (2):

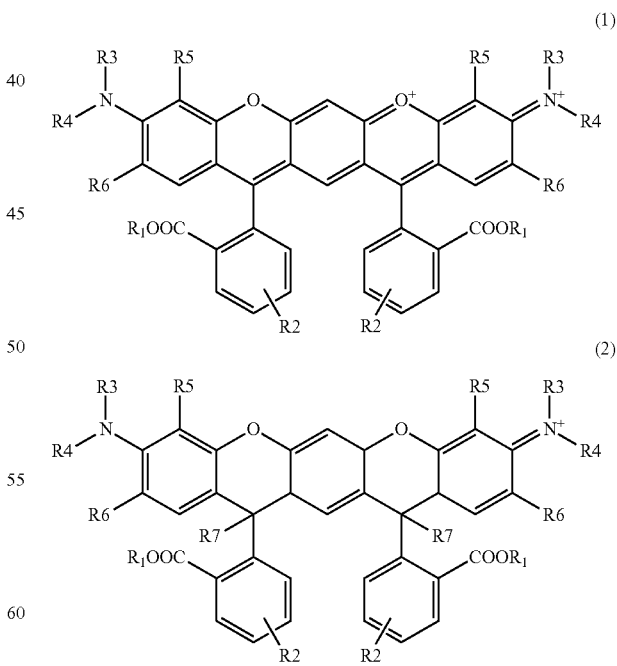

(In the formulae (1) and (2), each R1 independently represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; each R2 independently represents a C1 to C8 alkyl group (which may have a nitrogen atom, an oxygen atom, or a sulfur atom as a heteroatom), a halogen atom, a nitro group, a carboxyl group, an amino group, or a hydrogen atom; each R3 and each R4 independently represent a C1 to C8 alkyl group (which may have a nitrogen atom, an oxygen atom, or a sulfur atom as a heteroatom), an allyl group, an aryl group, or a hydrogen atom; each R5 and each R6 independently represent a C1 to C8 alkyl group (which may have a nitrogen atom, an oxygen atom, or a sulfur atom as a heteroatom), an allyl group, a halogen atom, or a hydrogen atom; and R3 and R5, and/or R4 and R6 may be bound to each other to form a ring. In the formula (2), each R7 independently represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; and R1 and R7 may be bound to each other to form a ring).

In the formulae, the C1 to C8 alkyl group may be straight, branched, or annular. Examples of the C1 to C8 alkyl group may be a methyl group, an ethyl group, a propyl group, an isopropyl group, a butyl group, an isobutyl group, an s-butyl group, a t-butyl group, a pentyl group, an isopentyl group, a neopentyl group, a heptyl group, an octyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1-ethyl-1-methylpropyl group, a cyclopentane group, a cyclohexane group, a cycloheptane group, a cyclooctane group, or the like. Further, a main chain of the alkyl group may have, as a heteroatom, a nitrogen atom, an oxygen atom, or a sulfur atom. Moreover, the amide group may have a protective group or a substituent. The protective group may be, for example: a urethane protective group such as a t-butoxy carbonyl group; an acyl protective group such as a benzoyl group; an alkyl protective group such as a trityl group; or an imine protective group such as dimethyl acetal. The substituent may be, for example, a pyridyl group, a halogen atom, or the like. Further, the substituent and the amide group may be bound to each other via a ligand (for example, an alkylene group such as a methylene group).

The allyl group may be a monovalent unsaturated hydrocarbon group, and may be straight or branched. The halogen atom may be, for example, a fluorine atom, a chlorine atom, a bromine atom, or an iodine atom. The aryl group may be a phenyl group, a tolyl group, a xylyl group, a naphthyl group, or the like.

Further, the aforementioned compound may be any one of compounds represented by the following formulae (3) to (22):

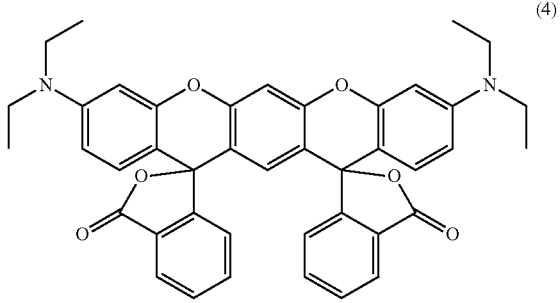
(3)

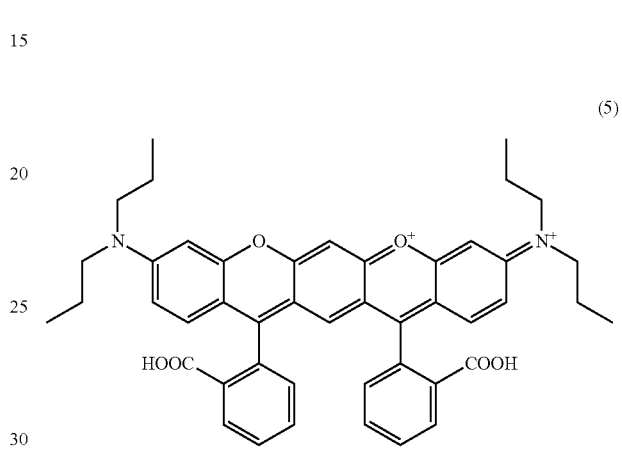
(4)

(5)

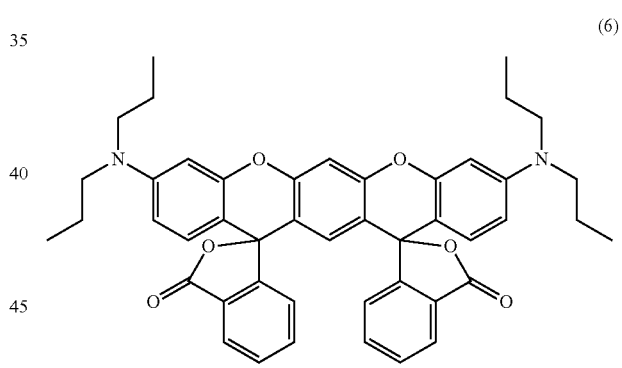
(6)

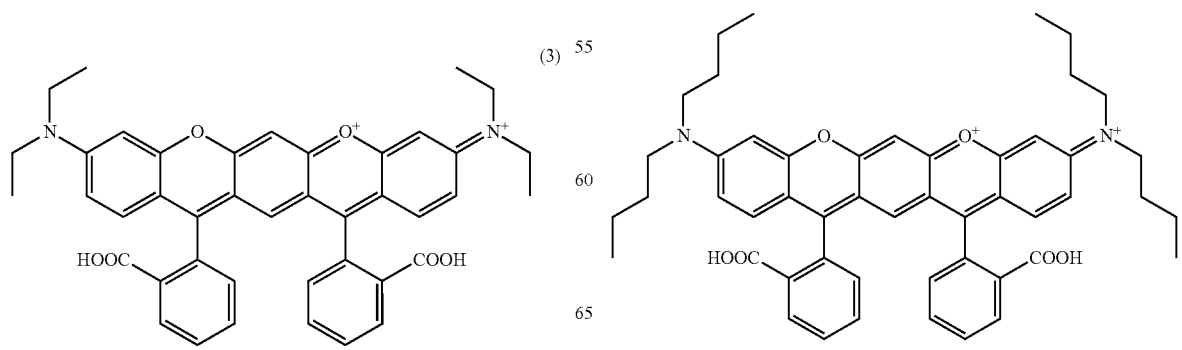
(7)

-continued
(8)
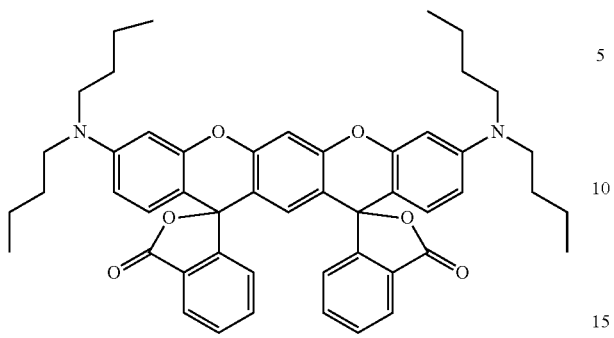
(9)
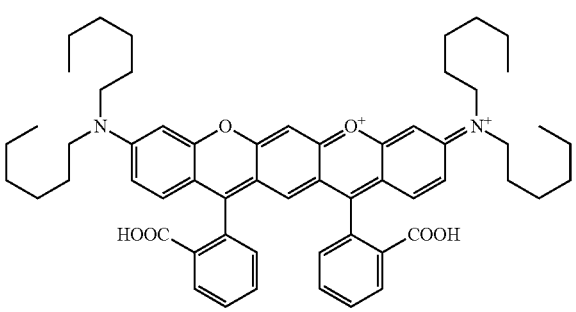
(10)
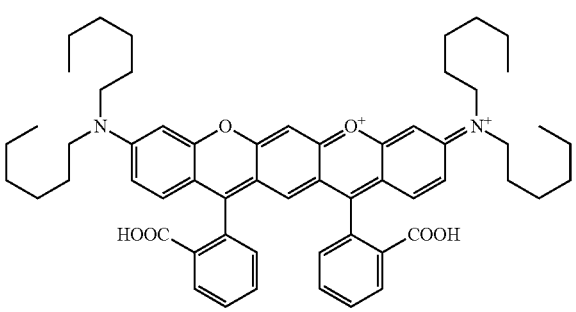
(11)
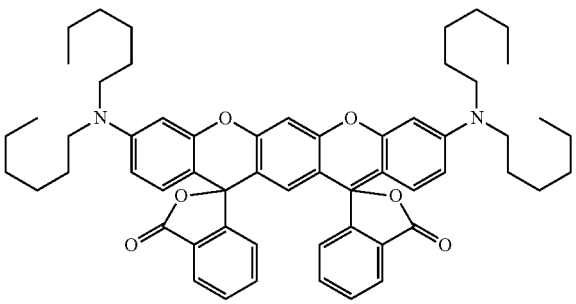
(12)
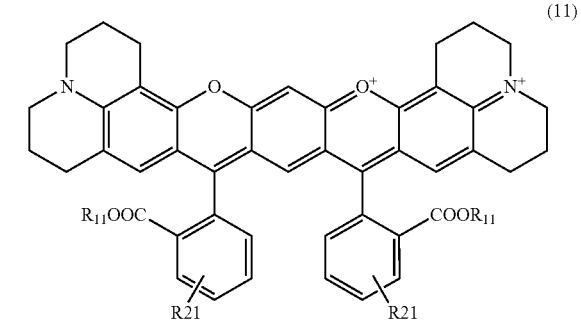
-continued
(13)
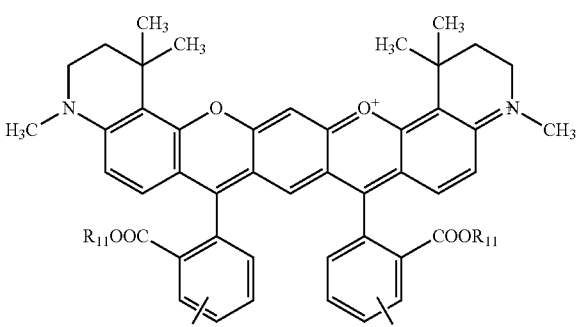
(14)
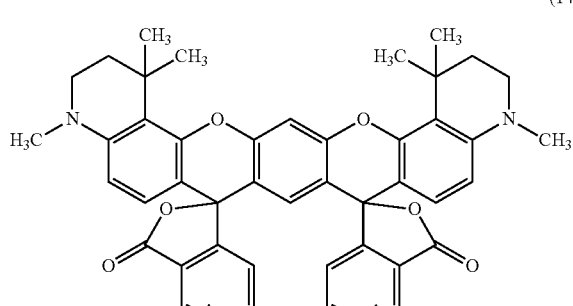
(15)
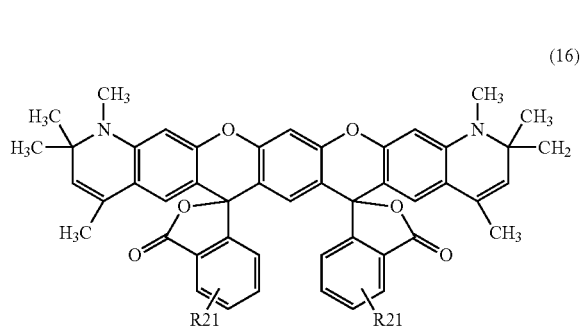
(16)
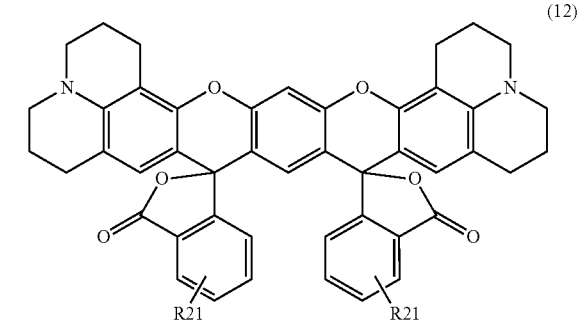
(17)
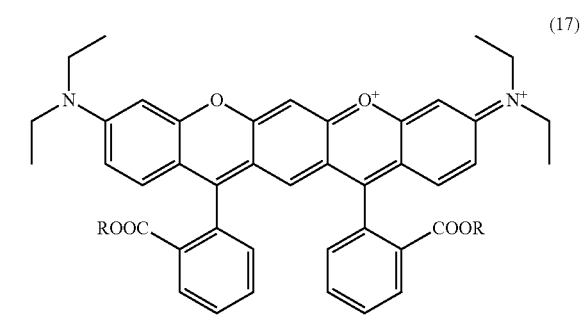

-continued

(18)
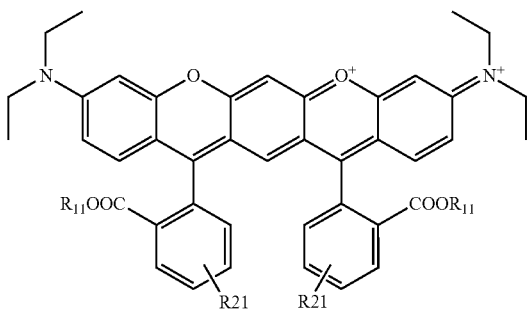

(19)
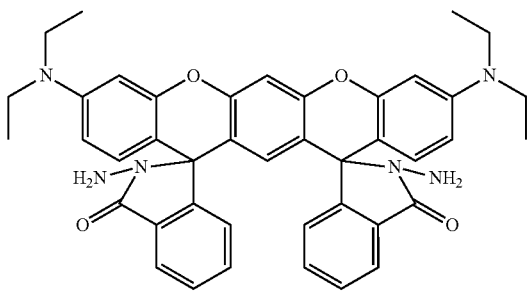

(20)
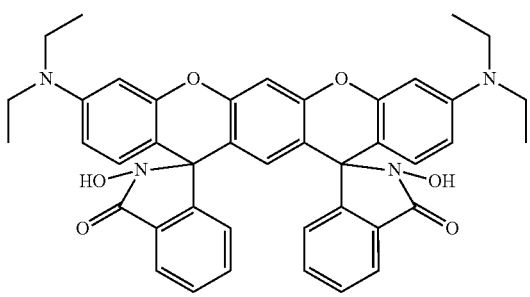

(21)
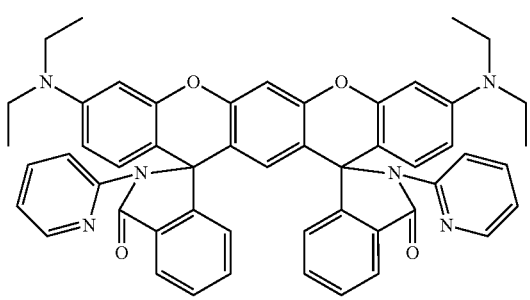

(22)
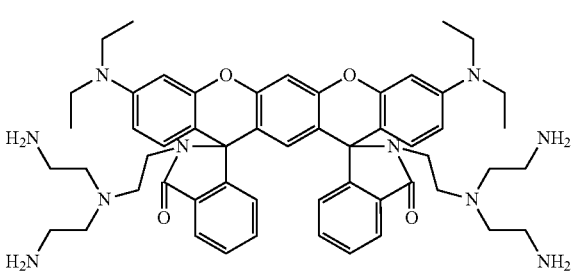

(In the formulae, each R and each R11 independently represent a C1 to C8 alkyl group (which may have a nitrogen atom, an oxygen atom, or a sulfur atom as a heteroatom) or a hydrogen atom; and each R21 independently represents a C1 to C8 alkyl group (which may have a nitrogen atom, an oxygen atom, or a sulfur atom as a heteroatom), a halogen atom, a nitro group, a carboxyl group, an amino group, or a hydrogen atom). That is, in the formulae, each R and each R11 may independently form an o-carboxylic acid and ester in a benzene moiety. The alkyl group and the halogen atom are the same as those explained in the formulae (1) and (2).

When using in the present Description, the compound of the present invention indicates not only a compound having a structure represented by any one of the aforementioned formulae, but also a salt thereof. Examples of the salt are preferably alkali metal salts (e.g., sodium salt, potassium salt), alkaline earth metal salts (e.g., calcium salt, magnesium salt), salts with an inorganic base (e.g., ammonium salt), organic amine salts (e.g., triethylamine salt, pyridine salt, picoline salt, ethanolamine salt, triethanolamine salt, dicyclohexylamine salt, N,N'-dibenzylethyleneamine salt, and the like), inorganic acid salts (e.g., hydrochloride salt, hydrobromate, sulfate, phosphate), organic carboxylate salts (e.g., formic acid, acetic acid, trifluoroacetate, maleate, tartrate, and the like), sulfonate (e.g., methanesulfonate, benzene sulfonate, p-toluene sulfonate, and the like), and salts with amino acids (e.g., arginine, asparaginic acid, glutamine acid, and the like). Further, the compound of the present invention may be a solvate, and may be, for example, hydrate or ethanolate.

Further, the compound of the present invention encompasses its derivative. A preferable example of the derivative in the present invention is a derivative of the compound in which ester is formed in a hydrophilic group (e.g., —OH, —CO$_2$H, —SO$_3$H and the like), and the hydrophilic group may be substituted with an acetyl group, an ethyl group, an ethynyl group, or the like. Further, examples of the derivative encompass: a derivative of the compound in which a hydrophilic group may be substituted with an alkyl group (e.g., a methyl group, an ethyl group, an n-propyl group, an i-propyl group, an n-butyl group, an i-butyl group, a sec-butyl group, a t-butyl group, or the like); and a derivative of the compound in which a hydrophilic group may be substituted with an electron attractive group.

The following explains various properties of the novel compound by taking the compound represented by the formula (3) (hereinafter, also referred to as "ABPX01"), as an example.

Figure 3:
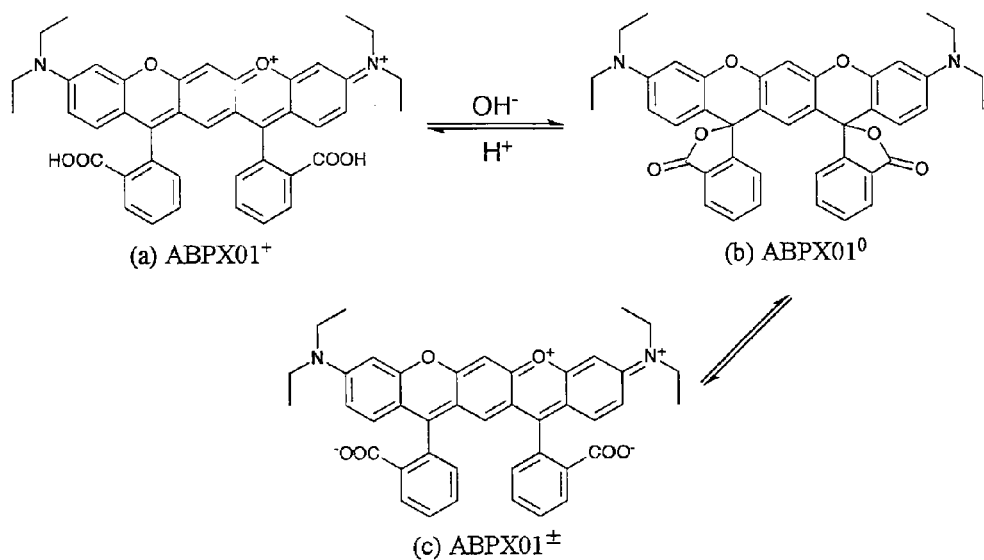
FIG. 3 illustrates three forms of ABPX01 in a solution: (a) ABPX01$^+$, which is a cationic form (colored); (b) ABPX01$^0$, which is a lactonoid form (colorless); and (c) ABPX01$^\pm$, which is a zwitterionic form (colored).

The ABPX01 is assumed to exist in solution in the following three dissociation forms, as illustrated in FIG. 3: (a) a cationic form (ABPX01$^+$), which is a conjugate type and exhibits color development; (b) a colorless lactonoid form (ABPX01$^0$), which is a non-conjugate type; and (c) a zwitterionic form (ABPX01$^\pm$), which exhibits color development. Needless to say, the compound in any of the three forms belongs to the present invention.

Among these three forms, the cationic form and the zwitterionic form are appropriate for use of the AIEE characteristic. In view of this, in order to use the characteristic of aggregation-induced emission enhancement of ABPX01, it is preferable to use ABPX01 under an acid condition in which an amine moiety is protonated. For example, it is preferable to add trifluoroacetic acid (TFA) to maintain protonation, so as to prevent formation of bases. A strong acid condition is preferably not more than pH3, more preferably not more than pH2, and further preferably not more than pH 1. The lower limit of the strong acid condition is not particularly limited because the acid condition is preferable to be as low as possible.

When X-ray crystal structure analysis was carried out on ABPX01, it was demonstrated that a luminophore has a chemical structure in which the luminophore is sandwiched between o-carboxylic acid moieties of benzenes. Further, it was observed that ABPX01 aggregates have a property that a particle size thereof increases over time. Further, the ABPX01 is easy to dissolve in organic solvents, such as chloroform, methanol, acetone, THF, and ethanol, but is not easy to dissolve in water. Further, as will be shown in the after-mentioned examples, the compound of the present invention encompassing the ABPX01 may exhibit different AIEE depending on solvents. Moreover, level-off tails attributed to a Mie scattering effect were observed. Accordingly, there is a possibility that the particle diameter of the aggregates may vary depending on solvents.

Further, due to the property of the compound of the present invention encompassing the ABPX01, it is possible to prepare pseudo aggregates by dissolving the compound in an organic solvent (THF or the like), in which the compound is easily dissolved, and adding water to the organic solution. With the use of the system, it is possible to easily carry out an on-off control of fluorescence by means of the AIEE characteristic, thereby allowing the compound to be used for photo-switching.

Further, compounds (ABPX02, ABPX03, ABPX04) were prepared in each of which a C2 ethyl group included in an amino group in a luminophore moiety of ABPX01 is replaced by any one of a C3 propyl group (for ABPX02), a C4 butyl group (for ABPX03), or a C6 hexyl group (for ABPX04). Then, absorption wavelengths and fluorescent spectra of these compounds were examined. As a result of the examinations, it was found that a long N-alkyl chain does not affect AIEE. On the other hand, it was found that as the N-alkyl chain becomes longer, an fluorescent wavelength tends to shift to a longer-wavelength side (exhibits a red shift). This is presumably related to a change in a sliding angle ($\alpha$) in a pigment array in an aggregate. Thus, these results suggest that ABPX01 to ABPX04 form J-type aggregates when they aggregate.

The above description dealt with the properties of the compound of the present invention, with a focus on ABPX01. These properties thus described are not limited to ABPX01, but also broadly true with the compounds of the present invention, i.e., the compounds represented by the above formulae (1) to (22). Any of the compounds of the present invention exhibits AIEE and has a high luminous efficiency. In other words, any of the compounds of the present invention is very useful.

<2. Production Method of Compound>

A production method for producing the compound of the present invention, i.e., a production method for producing an aminobenzopyro-xanthene dye may include the step of carrying out a condensation process of condensing 2 equivalents of a benzophenone derivative and 1 equivalent of resorcinol in the presence of Lewis acid. In the condensation process, heat condensation reaction is especially preferably carried out. The heat condition is preferably not less than 70° C. but not more than 150° C., more preferably not less than 80° C. but not more than 120° C., further preferably not less than 90° C. but not more than 100° C. A time for the condensation process is preferably not less than 10 minutes but not more than 10 hours, more preferably not less than 30 minutes but not more than 5 hours, further preferably not less than 1 hour but not more than 3 hours, for example.

The Lewis acid that can be used in the present invention is not especially limited and may be any substances that receive a pair of electrons as an electron-pair receptor. Examples of the Lewis acid may be aluminum trichloride, methanesulfonic acid, sulfuric acid, hydrochloric acid, zinc chloride, trifluoroacetic acid, and trifluoromethanesulfonate.

A solvent to be used is not especially limited, and conventionally known solvents can be used. Examples of the solvent to be used preferably may be water, alcohols such as methanol and ethanol, chloroform, dichloromethane, dimethylformamide, dimethylsulfoxyde, tetrahydrofuran, ether, and the like.

Further, it is preferable that the production method for producing the compound of the present invention further include the steps of: (a) adjusting a solution containing a reactant prepared in the condensation process so that the solution becomes basic; (b) mixing the solution with an organic solvent to extract the reactant into an organic phase; and (c) separating the reactant from the organic phase.

Purification of rhodamine dyes is generally difficult because the rhodamine dyes are hydrophilic and form keto-enol tautomers. More specifically, for ABPX01, which has been explained above, ABPX01 exists in solution in the cationic form (ABPX01$^+$) and the zwitterionic form (ABPX01$^\pm$), which have quite similar resonance structure. Therefore, they are difficult to separate from crude products. However, the inventors found the fact that by collecting a reactant as the lactonoid form, it is possible to easily separate the reactant in good yield. More specifically, the ABPX01 is made into the lactonoid form under the basic condition, so that the ABPX01 can be easily separated in good yield. Here, the "basic" is preferably in a range of pH9 to pH13, especially preferably weak basic, for example in a range of pH11 to pH12.

The organic solvent to be used is not especially limited, and conventionally known organic solvents that are usable in a solvent extraction method can be used. Examples of such organic solvents may be dichloromethane, chloroform, ethyl acetate, hexane, ether, and the like.

A method for separating the reactant from the organic phase is not especially limited, but may be, for example, a method using silica gel normal phase chromatography.

Further, the benzophenone derivative used in the production method for producing the compound of the present invention is preferably a compound represented by the following formula (23):

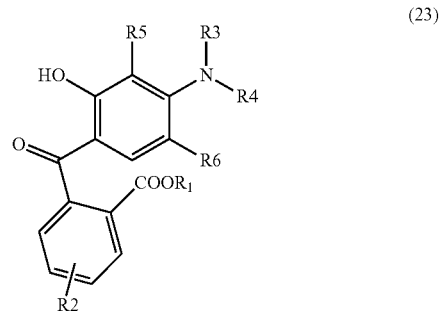

(23)

(wherein R1 represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; R2 represents a C1 to C8 alkyl group (which may have a nitrogen atom, an oxygen atom, or a sulfur atom as a heteroatom), a halogen atom, a nitro group, a carboxyl group, an amino group, or a hydrogen atom; R3 and R4 each independently represent a C1 to C8 alkyl group (which may have a nitrogen atom, an oxygen atom, or a sulfur atom as a heteroatom), an allyl group, an aryl group, or a hydrogen atom; R5 and R6 each independently represent a C1 to C8 alkyl group (which may have a nitrogen atom, an oxygen atom, or a sulfur atom as a heteroatom), an allyl group, a halogen atom, or a hydrogen atom; and R3 and R5, and/or R4 and R6 may be bound to each other to form a ring). The alkyl group, the amino group, the amide group which may have a protective group or a substituent, and the halogen atom are the same as those explained in the formulae (1) and (2), and therefore not explained here.

How to produce the benzophenone derivative is not especially limited, and a generally used synthetic technique can be used. For example, as in the present Example, the benzophenone derivative can be easily produced by Friedel-Crafts acylation (S. Kamino, H. Ichikawa, S. I. Wada, Y. Horio, Y. Usami, T. Yamaguchi, T. Koda, A. Harada, K. Shimanuki, M. Arimoto, M. Doi and Y. Fujita, Bioorg. Med. Chem. Lett., 2008, 18, 4380.).

According to the production method of the compound of the present invention, it is possible to easily produce an aminobenzopyro-xanthene dye which exhibits AIEE and which has a high luminous efficiency.

<3. Use of Compound>

The compound of the present invention is an aminobenzopyro-xanthene dye which exhibits AIEE and which has a high luminous efficiency. The use of the compound of the present invention may be, for example, a fluorescence emission method including the step of causing the compound of the present invention to aggregate. Further, a quenching method for quenching emission of fluorescence, which includes the step of eliminating aggregation of the compound of the present invention, is also included in the present invention. This method is a so-called method for controlling an on-off state of fluorescence. For example, by mixing a readily-soluble solvent in which the compound of the present invention is dissolved, with a poor-soluble solvent, it is possible to easily control an on-off state of fluorescence. The step of causing the compound to aggregate and the step of eliminating the aggregation may be carried out in solution or by doping the compound on a solid. Further, these steps can be also carried out in vitro, in vivo or ex vivo. Further, the compound of the present invention is usable to various fields as described below.

(3-1. Fluorescence Imaging Field)

The compound of the present invention is usable as a fluorescent probe using its AIEE characteristic as a photo-switching mechanism. For example, in the compound of the present invention, an on-off control of its fluorescence state can be performed owing to the AIEE characteristic. This allows the compound of the present invention to be used as a fluorescent probe for analyzing an aggregation mechanism of abnormal protein that causes diseases. The diseases may be, for example, diseases that are considered to occur due to aggregation of protein, such as Alzheimer, Parkinson's disease, Huntington's disease, prion disease, and the like.

More specifically, the compound of the present invention is used to label a target protein (or its precursor protein), so that the aggregation mechanism of the target protein can be analyzed in vitro, in vivo or ex vivo based on an on-off state of fluorescence. For example, assume a case where fluorescence is detected when metal ions are added to a protein solution in which the compound of the present invention is used for labeling the protein. In this case, it can be judged that the presence of the metal ions is closely related to the aggregation of the protein, whereby the aggregation mechanism of the target protein, eventually, a factor of a disease can be analyzed. That is, the present invention also includes a method for analyzing an aggregation mechanism of a target protein, which method includes the step of detecting emission of fluorescence in regard to the target protein labeled by the compound of the present invention.

In a case where a target protein included in a biological sample taken from a test subject is labeled, the method may include the step of incubating the compound of the present invention together with the biological sample. On the other hand, in a case where a target protein is labeled in vivo, the method may include the step of administering into a living organism the compound of the present invention together with a substance that targets the compound to the target protein. In this case, the administration may be preferably carried out by injection via various paths. However, how to administer the compound and the like is not limited to this. Further, doses of the compound and the like may be appropriately designed by a skilled person in the related art, as needed.

Further, by use of the cationic property and the AIEE characteristic of the compound of the present invention, it is possible to detect by fluorescence an electrochemical difference in membrane potential gradient of cells qualitatively and quantitatively.

Moreover, the compound of the present invention can be used as a nano probe for carrying out fluorescence imaging on a diseased portion. For example, a probe obtained by chemically modifying the compound of the present invention and biological molecules (preferably a biorecognition substance) such as antibodies, peptides, nucleotides, or sugars that recognize various diseases such as cancer and inflammation is administered into a living organism, so that only the diseased portion is visualized by fluorescence. That is, the present invention also includes a method for labeling a biological molecule (preferably a biorecognition substance) selected from the group consisting of antibodies, peptides, nucleotides, and sugars, with the use of the compound of the present invention. Further, the present invention also encompasses a method for producing a fluorescent probe which method includes the step of labeling the compound of the present invention and a biological molecule selected from the group consisting of antibodies, peptides, nucleotides, and sugars. Further, a fluorescent probe including the compound of the present invention and a biological molecule (preferably a biorecognition substance) selected from the group consisting of antibodies, peptides, nucleotides, and sugars is also encompassed in the present invention.

Note that general labeling techniques existing as of the filing of the application of the present invention, such as chemical modification, biological binding, ion binding, hydrophobic binding, and electrical binding, are usable as the "labeling" mentioned in the present Description, as appropriate. Further, the "biorecognition substance" indicates a substance that specifically recognizes a living organism, a specific organ, tissues, and cells derived from a living organism, and a biological molecule (including a diseased portion). The biorecognition substance is typified as antibodies.

Further, the present invention includes a method for carrying out diagnostic imaging by fluorescence imaging with the use of the fluorescent probe. That is, a method for analyzing a diseased portion by fluorescence imaging by administering the fluorescent probe into a patient is also encompassed in the present invention. The disease is preferably a cancer.

The "cancer" in the present Description is typified as, for example, malignant tumor of hematopoietic cells, leukosis, lymphoma, Hodgkin's disease, non-Hodgkin's lymphoma, multiple myeloma, brain tumor, breast cancer, uterine body cancer, endocervical cancer, ovary cancer, esophageal cancer, stomach cancer, appendix cancer, large bowel cancer (including colon, rectum, anus, and tissues around them), liver cancer, gallbladder cancer, bile duct cancer, pancreas cancer, adrenal cancer, gastrointestinal stromal tumor, mesothelioma, head and neck cancer, carcinoma laryngis, mouth cancer, cancer of floor of mouth, gum cancer, tongue cancer, buccal mucosa cancer, salivary gland cancer, paranasal cancer, maxillary sinus cancer, frontal sinus cancer, ethmoid antrum cancer, cancer of sinus sphenoidalis, thyroid (gland) cancer, kidney cancer, lung cancer, bone cancer, prostate cancer, testicular tumor and testicle cancer, renal cancer, bladder cancer, rhabdomyosarcoma, skin cancer, anus cancer, and the like.

For example, in a case where the above analyzing method is performed with the use of a biological sample taken from a test subject, the analyzing method may include the steps of (a) incubating the fluorescent probe together with the biological sample; and (b) detecting a fluorescent moiety. In a case where information for diagnosis is directly obtained from a living organism (i.e., in a case of diagnostic imaging), the analyzing method may include the steps of: (a) administering the fluorescent probe into the living organism; and (b) detecting a fluorescent moiety. In this case, the administration is preferably carried out by injection via various paths. However, how to administer the fluorescent probe is not limited to this. Further, doses of the fluorescent probe may be appropriately designed by a skilled person in the related art, as needed.

Moreover, the compound of the present invention may be provided as a labeling kit for labeling various substances. In the present Description, the term "kit" indicates a package including a container (e.g., bottle, plate, tube, dish, or the like) containing specific materials. Preferably, the kit includes an instruction for use of the materials. In the explanation related to the "kit" in the present Description, the term "include (including)" means a state in which materials are contained in any of individual containers constituting the kit. Further, the kit may be a package that packs a plurality of different compositions all together. The "instruction" may be written or printed on paper or the like medium, or may be stored in an electronic medium, such as a magnetic tape, a computer-readable disk or tape, or a CD-ROM. Moreover, the kit may include a container that contains a dilution agent, a solvent, a cleaning fluid, or the like reagent. Further, the kit may include necessary equipment depending on purposes.

(3-2. Medical Field)

The compound of the present invention can be used as a next-generation photosensitive medical agent that can simultaneously diagnose cancer and carry out photodynamic therapy (PDT) on the cancer. Conventionally, photosensitizers (PS) used for PDT have such a problem that they cannot be applied clinically because reactive oxygen species necessary for therapy are difficult to be generated due to a decrease in photosensitivity, which decrease is attributed to aggregation at a tumor. In contrast, the compound of the present invention has a property that as the concentration of the compound becomes high, the compound is improved in luminous efficiency and photosensitivity. In view of this, the compound of the present invention can be used as PS that can simultaneously carry out imaging of a lesioned part and photodynamic therapy on the lesioned part in such a manner that a necessary therapeutic amount (for example, one to tens of thousands of molecules) of the compound is sealed into and/or fixed to particles made of various polymers and the like such as liposome, silica gel, or PEG.

Such application of the compound of the present invention to the medical field can contribute to customized medical services because a delivery concentration of PS can be controlled according to how large cancer is and to which extent the cancer proceeds. Further, by binding, to surfaces of the particles, antibodies or peptides that recognize molecules that are expressed specifically in cancer, or by adjusting a particle system, it is possible to improve PS in specificity to cancer and permeableness into deep portions of tissues. Further, the application of the compound to the fluorescence imaging technique, it is possible to specify cancer and analyze therapeutic effects. Further, as compared with independent administration of PS, quantum dot, and the like, a decrease in toxicity is promising, which can contribute to improvement of QOL of patients.

Accordingly, the present invention encompasses a medicine for photodynamic therapy which contains the compound of the present invention. Further, a method for treating cancer by administering the compound of the present invention into a patient, particularly, a method for treating cancer by photodynamic therapy is also encompassed in the present invention. The administration of the medicine or the compound into a living organism is preferably carried out by injection via various paths, but is not limited in any particular manner. Further, doses of the medicine or the compound may be appropriately designed by a skilled person in the related art, as needed.

(3-3. Environment/Energy Field)

The compound of the present invention has a property that when the compound is aggregated, its photosensitization is increased. Further, the compound of the present invention has a broad light-absorption range (365 nm to 600 nm). In view of this, a novel light-absorbing organic-dye material for a dye-sensitized solar cell having a high photocarrier generation efficiency can be made by fixing a large amount of the compound to a glass or film substrate. Further, since there is no resource constraint and the compound can be produced in large volume at low cost, there is a less possibility to cause negative effects on the environment. In view of this, the present invention can encompass a dye-sensitized solar cell that includes the compound of the present invention as a light-absorbing organic-dye material.

Further, the compound of the present invention is expected to be used for an organic light-emitting diode or the like by doping the compound on a thin film. Thus, the compound of the present invention can be used in the form of various organic light-emitting devices that include the compound therein.

EXAMPLES

The following describes the present invention more specifically based on examples as below. However, the present invention is not limited to the description below.

Reagents were purchased from Wako Pure Chemical Industries, Ltd., NACALAI TESQUE, INC., or TCI Japan. All other solvents were used without further purification. Experiments were conducted under an atmosphere of dry nitrogen or using a guard tube.

$^1$H-NMR and $^{13}$C-NMR spectra were recorded using 300 or 500 MHz spectrometers (Varian UNITY INOVA). Solvents used for NMR measurements were $CDCl_3$, DMSO-$d_6$ or TFA-$d_8$, with TMS as the internal standard. Mass spectra were acquired using a JMX-700 (2) (JEOL Co., Ltd.) MS instrument. Melting points were determined on a Yanagimoto micromelting point apparatus and are uncorrected. Liquid column chromatography was conducted over silica gel (Merck Silica Gel 60 mesh 70-230). Developed TLC plates were visualized under a short-wave UV lamp, by staining with an $I_2$—$SiO_2$ mixture, and/or by heating plates that were dipped in ammonium phosphomolybdate sulfate solution. Dry THF was distilled over sodium benzophenone ketyl under argon atmosphere.

UV-vis spectra were collected on a SHIMADZU UV-1700 spectrophotometer at RT (room temperature) using a 1 cm or a 0.1 cm quartz cuvette. Emission spectra were collected on a HITACHI F-4500 fluorescence spectrophotometer. To obtain an accurate spectrum, spectrum correction was carried out with rhodamine B concentrated solution and a secondary-standard light source. In surface photometry, a cut filter was utilized to eliminate multiple lights, such as secondary light, due to the effects of light scattering. Fluorescence spectra of all samples were measured with excitation with 365 nm. Average particle size was measured by dynamic light scattering (ELSZ-2, Otsuka Electronics).

Initially, a synthesis route for new class of rhodamine dyes: 3',3"-bis(oxospriroisobenzofuran)-3,7-bis(dialkylamino) benzopyrano-xanthene derivatives (ABPX) was examined.

First, as illustrated in FIG. 1, benzophenone derivatives were prepared via Friedel-Crafts acylation (S. Kamino, H. Ichikawa, S. I. Wada, Y. Horio, Y. Usami, T. Yamaguchi, T. Koda, A. Harada, K. Shimanuki, M. Arimoto, M. Doi and Y. Fujita, Bioorg. Med. Chem. Lett., 2008, 18, 4380.). More specifically, to a solution of phthalic anhydride (1 equiv) and anhydrous $AlCl_3$ (1.1 equiv) in $CH_2Cl_2$, a compound (1 equiv) represented by "1" ("1a" to "1d" in FIG. 1) was slowly added and the mixture was stirred under nitrogen at 0° C. for 4 hours. Then, the reaction mixture was poured into a mixture of water/6 M HCl, stirred for 10 minutes, and extracted with $CH_2Cl_2$. The combined organic phases were dried over $MgSO_4$ and evaporated to give the crude product. Recrystallization from $MeOH/H_2O$ solution of crude products "2a" to "2c" was carried out to obtain the pure product as a yellow solid, and a crude product "2d" was purified by silica gel column chromatography to obtain the pure product as yellow viscous oil.

Compound "2a"

(2-[4-(Diethylamino)-2-methoxybenzoyl]benzoic acid)

$^1$-H-NMR ($CDCl_3$, 500 MHz): δ 8.00 (dd, 1H, J=7.8, 0.8 Hz), 7.65 (d, 1H, J=8.9 Hz), 7.53 (td, 1H, J=8.9 Hz), 7.41 (td, 1H, J=7.8, 1.1 Hz), 7.27 (d, 1H, J=7.3 Hz), 6.24 (dd, 1H, J=8.9, 2.3 Hz), 5.99 (sd, 1H, J=2.1 Hz), 3.55 (s, 3H), 3.40 (q, 4H, J=7.1 Hz), 1.20 (t, 6H, J=7.1 Hz). $^{13}$C-NMR ($CDCl_3$, 500 MHz): δ 193.9, 170.7, 162.2, 153.1, 146.4, 134.4, 132.3, 130.4, 127.9, 127.4, 126.9, 114.3, 103.8, 93.6, 55.3, 44.6, 12.6. HRMS (EI) calcd for $C_{18}H_{19}NO_4$ (M$^+$): 327.1471, Found: 327.1471. Yield: 60%.

Compound "2b"

(2-[4-(Dipropylamino)-2-methoxybenzoyl]benzoic acid)

$^1$-H-NMR ($CDCl_3$, 500 MHz): δ 8.00 (dd, 1H, J=7.8, 0.92 Hz), 7.63 (d, 1H, J=8.7 Hz), 7.52 (td, 1H, J=7.3, 1.1 Hz), 7.40 (td, 1H, J=7.6, 1.1 Hz), 7.26 (d, 1H, J=6.6 Hz), 6.23 (dd, 1H, J=9.2, 2.3 Hz), 5.97 (sd, 1H, J=2.3 Hz), 3.54 (s, 3H), 3.28 (brs, 4H), 1.68-1.60 (m, 4H), 0.94 (t, 6H, J=7.3 Hz). $^{13}$C-NMR ($CDCl_3$, 500 MHz): δ 193.8, 170.9, 162.1, 153.5, 146.5, 134.3, 132.3, 130.3, 127.9, 127.4, 126.8, 114.3, 104.0, 93.9, 55.2, 52.8, 20.5, 11.4. HRMS (EI) calcd for $C_{21}H_{25}NO_4$ (M$^+$): 355.1779, Found: 355.1786. Yield: 24%.

Compound "2c"

(2-[4-(Dibutylamino)-2-methoxybenzoyl]benzoic acid)

$^1$-H-NMR ($CDCl_3$, 500 MHz): δ 8.01 (dd, 1H, J=7.8, 0.92 Hz), 7.63 (brs, 1H), 7.53 (td, 1H, J=7.3, 1.1 Hz), 7.41 (td, 1H, J=7.8, 1.1 Hz), 7.26 (d, 1H, J=7.3 Hz), 6.22 (dd, 1H, J=9.2, 2.3 Hz), 5.98 (sd, 1H, J=1.8 Hz), 3.55 (s, 3H), 3.31 (brs, 4H), 1.63-1.57 (m, 4H), 1.40-1.32 (m, 4H), 0.96 (t, 6H, J=7.3 Hz). $^{13}$C-NMR ($CDCl_3$, 500 MHz): δ 193.9, 170.6, 164.7, 162.2, 153.5, 146.4, 134.4, 132.3, 130.4, 127.9, 127.4, 126.9, 114.2, 103.9, 93.8, 55.2, 50.8, 29.4, 20.2, 13.9. HRMS (EI) calcd for $C_{23}H_{29}NO_4$ (M$^+$): 383.2097, Found: 383.2093. Yield: 23%.

Compound "2d"

(2-[4-(Dihexylamino)-2-methoxybenzoyl]benzoic acid)

$^1$-H-NMR ($CDCl_3$, 500 MHz): δ 8.02 (dd, 1H, J=7.8, 0.92 Hz), 7.63 (brs, 1H), 7.53 (td, 1H, J=7.6, 1.4 Hz), 7.42 (td, 1H, J=7.8, 1.4 Hz), 7.27 (d, 1H, J=8.7 Hz), 6.21 (dd, 1H, J=8.9, 2.3 Hz), 5.97 (sd, 1H, J=1.8 Hz), 3.56 (s, 3H), 3.23 (t, 4H, J=7.8 Hz), 1.62-1.58 (m, 4H), 1.40-1.32 (m, 12H), 0.89 (t, 6H, J=7.1 Hz). $^{13}$C-NMR ($CDCl_3$, 500 MHz): 194.0, 170.4, 162.2, 153.5, 146.3, 134.4, 132.3, 131.9, 130.8, 130.5, 129.9, 128.6, 128.0, 127.5, 127.0, 114.2, 103.95, 93.8, 55.2, 52.8, 51.1, 31.6, 27.2, 26.7, 22.6, 14.0. HRMS (EI) calcd for $C_{27}H_{37}NO_4$ (M$^+$): 439.2723, Found: 439.2730.

To a stirred solution of a compound "2" (1.0 equiv) in $CH_2Cl_2$ was added a solution of $BBr_3$ (1.9 equiv) in $CH_2Cl_2$ at −78° C. After 1 hour, the mixture was warmed to −25° C. After completion of the reaction, the mixture was quenched with $H_2O$ and evaporated to give the crude product. Recrystallization from $MeOH/H_2O$ solution of compounds "3a" to "3c" yielded the pure product as a yellow solid, and a compound "3d" was purified by silica gel column chromatography to obtain the pure product as yellow viscous oil.

Compound "3a"

(2-[4-(Diethylamino)-2-hydroxybenzoyl]benzoic acid)

$^1$-H-NMR ($CDCl_3$, 500 MHz): δ 12.65 (s, 1H), 8.07 (dd, 1H, J=7.8, 0.9 Hz), 7.58 (td, 1H, J=7.6, 1.4 Hz), 7.51 (td, 1H, J=7.8, 1.4 Hz), 7.34 (dd, 1H, J=7.6, 1.1 Hz), 6.91 (d, 1H, J=8.9 Hz), 6.11 (sd, 1H, J=2.5 Hz), 6.03 (dd, 1H, J=9.2, 2.5 Hz), 3.37 (q, 4H, J=7.1 Hz), 1.18 (t, 6H, J=7.1 Hz). $^{13}$C-NMR ($CDCl_3$, 500 MHz): δ 199.0, 167.5, 165.2, 153.6, 140.6, 134.6, 131.6, 130.4, 129.5, 128.9, 127.6, 110.1, 103.5, 96.7, 44.5, 12.5. HRMS (EI) calcd for $C_{19}H_{21}NO_4$ (M$^+$): 313.1314, Found: 313.1313. Yield: 65%.

Compound "3b"

(2-[4-(Dipropylamino)-2-hydroxybenzoyl]benzoic acid)

$^1$-H-NMR ($CDCl_3$, 500 MHz): δ 12.53 (s, 1H), 8.10 (d, 1H, J=7.1 Hz), 7.62 (t, 1H, J=7.3 Hz), 7.53 (t, 1H, J=7.3 Hz), 7.36 (dd, 1H, J=7.8, 1.1 Hz), 6.87 (d, 1H, J=9.2 Hz), 6.12 (s, 1H), 6.03 (d, 1H, J=8.9 Hz), 3.26 (t, 4H, J=7.6 Hz), 1.65-1.59 (m, 4H), 0.92 (t, 6H, J=7.3 Hz). $^{13}$C-NMR ($CDCl_3$, 500 MHz): δ $^1$-H-NMR ($CDCl_3$, 500 MHz): δ 198.1, 169.8, 165.4, 154.4, 141.2, 134.5, 132.7, 131.1, 129.1, 128.1, 127.6, 109.9, 104.0, 97.3, 52.8, 20.5, 11.3. HRMS (EI) calcd for $C_{20}H_{23}NO_4$ ($M^+$): 341.1630, Found: 341.1626. Yield: 52%.

Compound "3c"

2-[4-(Dibutylamino)-2-hydroxybenzoyl]benzoic acid $^1$-H-NMR (CDCl$_3$, 500 MHz): δ 12.54 (s, 1H), 8.12 (d, 1H, J=7.8 Hz), 7.63 (t, 1H, J=7.3 Hz), 7.54 (t, 1H, J=7.6 Hz), 7.36 (dd, 1H, J=7.6, 0.92 Hz), 6.87 (d, 1H, J=8.9 Hz), 6.11 (s, 1H), 6.03 (d, 1H, J=8.5 Hz), 3.29 (t, 4H, J=7.3 Hz), 1.58 (brs, 4H), 1.37-1.30 (m, 4H), 0.94 (t, 6H, J=7.3 Hz). $^{13}$C-NMR (CDCl$_3$, 500 MHz): δ 198.1, 169.5, 165.5, 154.4, 141.1, 134.5, 132.7, 131.1, 129.2, 128.1, 127.6, 109.8, 103.9, 97.2, 50.9, 29.4, 20.2, 13.9. HRMS (EI) calcd for $C_{22}H_{27}NO_4$ ($M^+$): 369.1940, Found: 369.1932. Yield: 49%.

Compound "3d"

(2-[4-(Dihexylamino)-2-hydroxybenzoyl]benzoic acid)

$^1$-H-NMR (CDCl$_3$, 500 MHz): δ 12.55 (s, 1H), 8.10 (dd, 1H, J=8.0, 0.92 Hz), 7.62 (dd, 1H, J=7.6, 1.4 Hz), 7.53 (td, 1H, J=7.8, 1.4 Hz), 7.34 (dd, 1H, J=7.1, 0.92 Hz), 6.87 (d, 1H, J=9.2 Hz), 6.11 (sd, 1H, J=2.5 Hz), 6.02 (dd, 1H, J=9.2, 2.5 Hz), 3.27 (brs, 4H), 1.59 (brs, 4H), 1.33-1.30 (m, 12H), 0.90-0.88 (m 6H). $^{13}$C-NMR (CDCl$_3$, 500 MHz): δ 198.1, 169.0, 165.5, 154.4, 141.1, 134.5, 132.6, 131.1, 129.1, 128.1, 127.7, 109.8, 103.9, 97.2, 51.1, 31.59, 27.3, 26.7, 22.6, 14.0. HRMS (EI) calcd for $C_{26}H_{35}NO_4$ ($M^+$): 425.2563, Found: 425.2569.

Figure 2:
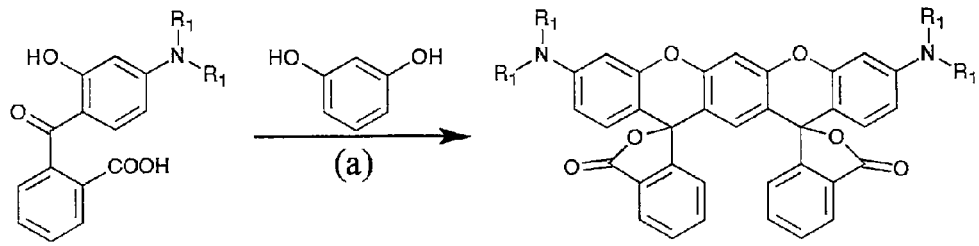
FIG. 2 illustrates a synthetic route for 3',3"-bis(oxospiroisobenzofuran)-3,7-bis(dialkylamino)benzopyrano-xanthene derivatives (ABPX).

Subsequently, the compound "3" thus obtained was condensed with resorcinol in CH$_3$SO$_3$H at 95° C. for 2 hours to obtain desired ABPX series. More specifically, as shown in the scheme illustrated in FIG. 2, the compound "3" (2.0 equiv) and resorcinol (1.0 equiv) were mixed in methanesulfuric acid (2.0 mL) in a sealed tube and heated at 90° C. for 2 hours. The reactant was poured into stirred ice water, its pH was adjusted to pH11 to pH12 with 1.0 M sodium hydroxide aqueous solution, and the mixture was stirred for 20 minutes. Then, the mixture was extracted with CH$_2$Cl$_2$ three times. The organic phases were dried over MgSO$_4$ and evaporated to give the crude product. This was purified by silica gel column chromatography and further recrystallized from acetonitrile solution to obtain the pure product as a white solid. ABPX01 has an N,N'-diethyl substituted entity. ABPX02 to ABPX04 were designed to have long N,N'-dialkyl chains and higher hydrophobicity than ABPX01.

Compound "4a"

(3',3"-Bis (oxospriroisobenzofuran)-3,7-bis(diethylamino)benzopyranoxanthene (ABPX01))

δ $^1$-H-NMR (THF-d$_8$, 500 MHz): δ 7.73-7.72 (m, 1H), 7.70 (dt, 1H, J=7.6, 1.1 Hz), 7.61 (td, 1H, J=7.6, 0.92 Hz), 7.52 (td, 1H, J=7.3, 0.9 Hz), 7.47-7.43 (m, 2H), 7.16 (dt, 1H, J=7.6, 0.9 Hz), 7.11 (s, 1H), 6.94-6.92 (m, 1H), 6.50-6.49 (m, 2H), 6.47 (d, 1H, J=7.6 Hz), 6.45 (d, 1H, J=7.6 Hz), 6.37-6.34 (m, 2H), 6.07 (s, 1H), 3.30-3.25 (m, 8H), 0.92 (t, 12H, J=7.6 Hz). $^{13}$C-NMR (CDCl$_3$, 500 MHz): δ 168.4, 168.3, 154.0, 153.9, 153.8, 153.1, 153.0, 151.0, 150.9, 135.5, 134.8, 130.3, 130.0, 129.7, 129.4, 129.3, 128.8, 128.4, 128.1, 125.0, 124.9, 124.8, 124.4, 118.00, 117.8, 109.6, 106.6, 106.5, 104.4, 104.3, 98.6, 98.5, 83.0, 82.8, 53.4, 11.5. $^{13}$C-NMR (CDCl$_3$, 500 MHz): 6 HRMS (FAB) calcd for $C_{42}H_{37}N_2O_6$ (M+H): 665.2651, Found: 665.2654. Yield: 72%.

Compound "4b"

(3',3"-Bis(oxospriroisobenzofuran)-3,7-bis(dipropylamino)benzopyranoxanthene (ABPX02))

$^1$-H-NMR (THF-d$_8$, 500 MHz): δ 7.73-7.72 (m, 1H), 7.70 (dt, 1H, J=7.6, 1.1 Hz), 7.61 (td, 1H, J=7.6, 0.92 Hz), 7.52 (td, 1H, J=7.3, 0.9 Hz), 7.47-7.43 (m, 2H), 7.16 (dt, 1H, J=7.6, 0.9 Hz), 7.11 (s, 1H), 6.94-6.92 (m, 1H), 6.50-6.49 (m, 2H), 6.47 (d, 1H, J=7.6 Hz), 6.45 (d, 1H, J=7.6 Hz), 6.37-6.34 (m, 2H), 6.07 (s, 1H), 3.30-3.25 (m, 8H), 1.65-1.57 (m, 8H), 0.92 (t, 12H, J=7.6 Hz). $^{13}$C-NMR (CDCl$_3$, 500 MHz): δ 168.4, 168.3, 154.0, 153.9, 153.8, 153.7, 153.2, 153.0, 151.0, 150.9, 135.5, 134.8, 130.3, 130.0, 129.7, 129.4, 129.3, 128.8, 128.4, 128.1, 125.0, 124.9, 124.8, 124.4, 118.0, 117.8, 109.6, 106.6, 106.5, 104.4, 104.3, 98.6, 98.5, 83.0, 82.8, 53.4, 21.1, 11.5. HRMS (FAB) calcd for $C_{46}H_{45}N_2O_6$ (M+H): 721.3278, Found: 721.3276. Yield: 56%.

Compound "4c"

(3',3"-Bis(oxospriroisobenzofuran)-3,7-bis(dibutylamino)benzopyranoxanthene (ABPX03))

$^1$-H-NMR (THF-d$_8$, 500 MHz): δ 7.74-7.72 (m, 1H), 7.70 (dt, 1H, J=7.6, 0.92 Hz), 7.62 (td, 1H, J=7.6, 1.1 Hz), 7.52 (td, 1H, J=7.3, 0.92 Hz), 7.47-7.43 (m, 2H), 7.16 (dt, 1H, J=7.6, 0.92 Hz), 7.13 (s, 1H), 6.94-6.92 (m, 1H), 6.50-6.49 (m, 2H), 6.47 (d, 1H, J=7.8 Hz), 6.45 (d, 1H, J=7.8 Hz), 6.37-6.34 (m, 2H), 6.07 (s, 1H), 3.33-3.30 (m, 8H), 1.60-1.54 (m, 8H), 1.40-1.32 (m, 8H), 0.95 (t, 12H, J=7.3 Hz). $^{13}$C-NMR (CDCl$_3$, 500 MHz): δ 168.4, 168.3, 154.0, 153.9, 153.8, 153.7, 153.2, 153.0, 151.0, 150.9, 135.4, 134.8, 130.3, 130.0, 129.7, 130.0, 129.4, 128.8, 128.5, 128.1, 125.0, 124.9, 124.8, 124.4, 118.0, 117.8, 109.6, 106.6, 106.5, 104.5, 104.4, 98.6, 98.5, 83.0, 82.8, 51.4, 30.2, 21.0, 14.3. HRMS (FAB) calcd for $C_{50}H_{53}N_2O_6$ (M+H): 777.3903, Found: 777.3911. Yield: 52%.

Compound "4d"

(3',3"-bis(oxospriroisobenzofuran)-3,7-bis(dihexylamino)benzopyranoxanthene (ABPX04))

$^1$-H-NMR (THF-d$_8$, 500 MHz): δ 7.74-7.72 (m, 1H), 7.70 (d, 1H, J=7.8 Hz), 7.62 (td, 1H, J=7.6, 0.92 Hz), 7.52 (td, 1H, J=7.6, 0.92 Hz), 7.47-7.44 (m, 2H), 7.16 (d, 1H, J=7.6 Hz), 7.12 (s, 1H), 6.94-6.92 (m, 1H), 6.49-6.48 (m, 2H), 6.47 (d, 1H, J=8.7 Hz), 6.45 (d, 1H, J=8.0 Hz), 6.36-6.34 (m, 2H), 6.06 (s, 1H), 3.31 (brs, 8H), 1.59 (brs, 8H), 1.33 (brs, 24H), 0.90 (brs, 12H). $^{13}$C-NMR (CDCl$_3$, 500 MHz): δ 168.4, 168.3, 154.0, 154.0, 153.9, 153.8, 153.7, 153.2, 153.0, 151.0, 150.9, 150.8, 135.4, 134.8, 130.3, 130.0, 129.7, 129.4, 129.3, 128.7, 128.5, 128.1, 125.0, 125.9, 124.8, 124.4, 118.0, 117.8, 109.6, 106.6, 106.5, 104.5, 104.4, 98.6, 98.5, 83.0, 82.8, 51.7, 32.7, 28.0, 27.6, 23.6, 14.4. HRMS (FAB) calcd for $C_{58}H_{69}N_2O_6$ (M+H): 889.5155, Found: 889.5165

FIG. 17 to FIG. 40 show NMR data of benzophenone derivatives and ABPX01 to ABPX04 synthesized in Examples.

Purification of rhodamine dyes is difficult because they are hydrophilic and form keto-enol tautomers. ABPX01 is speculated to exist in solution in a cationic form, ABPX01$^+$, and a neutral form, ABPX01, similarly to rhodamines (FIG. 3). The latter is represented by an equilibrium mixture of a colorless lactonoid form, ABPX01⁰, and a colored zwitterionic form, ABPX01±. That is, ABPX01 is expected to exist in solution in the following forms: (a) the cationic (colored) form, ABPX01⁺, (b) the lactonoid (colorless) form, ABPX01⁰, and (c) the zwitterionic (colored) form ABPX01±. The cationic form ABPX01⁺ as a resonance structure is appropriate for evaluation of AIEE. Therefore, trifluoroacetic acid (TFA) is added to ensure protonation and prevent pseudobase formation. ABPX01⁺ and ABPX01±, which have quite similar resonance structure, are difficult to separate from crude products. ABPX01 to ABPX04 were simply purified by silica gel normal phase chromatography via conversion into ABPX01⁰ to ABPX04⁰, respectively, by extraction in an alkaline solution. ABPX01⁰ was characterized by $^1$H and $^{13}$C-NMR spectroscopy in THF-$d_8$. The NMR profiles suggested that both stereoisomers of trans-ABPX01⁰ and cis-ABPX01⁰ derived from two stereocenters at 11- and 11'-positions were present at the ratio of approximately 1:1. ABPX02⁰ to ABPX04⁰ were also obtained as mixtures of the same stereoisomers (1:1). To further elucidate the structure of ABPX01, a single crystal of ABPX01⁰ suitable for X-ray diffraction analysis was grown by the slow evaporation of acetonitrile solution. Crystallographic data and experimental data are given as follows:

Crystal and experimental data: $C_{42}H_{37}N_2O_6$, M=665.76, orthorhombic, Fdd2, a=17.5837 (11), b=23.2759 (11), c=18.2237 (9) Å, α, β, γ=90°, V=7458.5 (7) Å$^3$, Z=8, Dx=1.186 g cm$^{-3}$, F(000)=2808, μ(MoKα)=0.079 mm$^{-1}$.

The data were collected on a Rigaku RAXIS-RAPID area detector using graphite-monochromated MoKa radiation at 293.1 K. A total of 17,587 reflections were measured up to $\theta_{max}$=27.46° (0.85 Å resolution) and merged to 14,495 reflections with $R_{int}$=0.034. The structure was solved using CrystalStructure 3.8 and refined with CrystalStructure 3.8. Non-hydrogen atoms were refined anisotropically. Hydrogen atoms were calculated at the ideal positions and isotropically included in the calculations of the structure factors. The structure was converted at goodness of fit=1.232, $(\Delta/\sigma)_{max}$=0.0088, $\Delta\rho_{max}$=2.50 eÅ$^{-3}$, $\Delta\rho_{min}$=-2.27 eÅ$^{-3}$, R=0.0589, and wR=0.0772. Crystallographic data (excluding structure factors) for the structure of ABPX01⁰ reported in the Description are deposited with the Cambridge Crystallographic Data Centre as supplementary publication number CCDC-779022. The data can be obtained free of charge from The Cambridge Crystallographic Data Centre.

Figure 4:
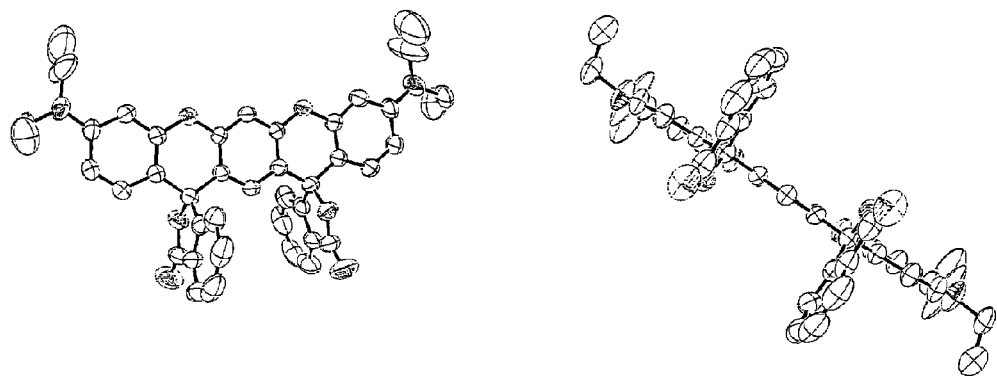
FIG. 4 is an ORTEP drawing of ABPX01$^0$.

ORTEP diagrams of ABPX01⁰ are shown in FIG. 4. The five rings of trans-ABPX01⁰ are aligned with a high degree of planarity. The conformational and structural behavior of ABPX appeared to be complicated in both solution and solid forms.

Figure 5:
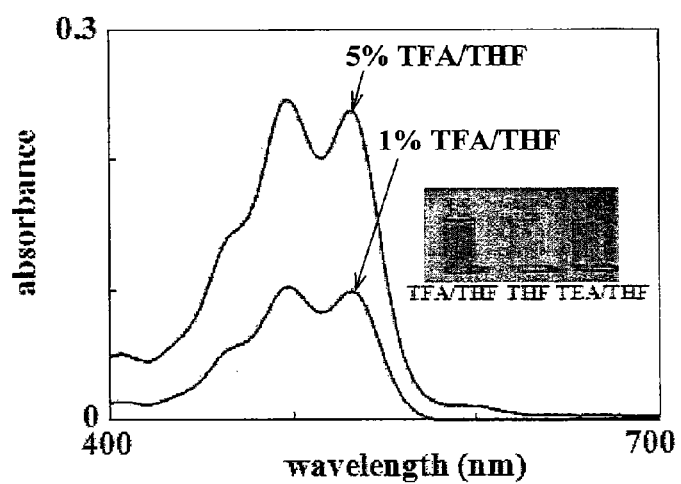
FIG. 5 shows effects of protonation reaction on absorption spectra of ABPX01 in TFA/THF solutions (TFA: trifluoroacetic acid, TEA: triethylamine). An inset is a photograph of the solutions under room light.

What molecular species of ABPX are appropriate for the evaluation of AIEE in solution was examined. In order to examine to find the appropriate ABPX01 species, the absorbance spectra of 5 M of ABPX01 were measured in acid or alkaline solution. Results thereof are shown in FIG. 5. In THF solution and 1% TEA/THF mixture, the spectra had no peaks that were attributable to the neutral lactonoid species ABPX01⁰. In the strong acid solutions of the TFA/THF mixtures, the absorbance spectra having two peaks at 490 nm and 540 nm should be attributable to the cationic form of ABPX01⁺. ABPX01⁺ is a quinonoid form delocalized over the luminophore and is therefore appropriate for the emission analysis. Hence, the AIEE characteristic of ABPX was estimated in a strong acid solution.

Figure 6:
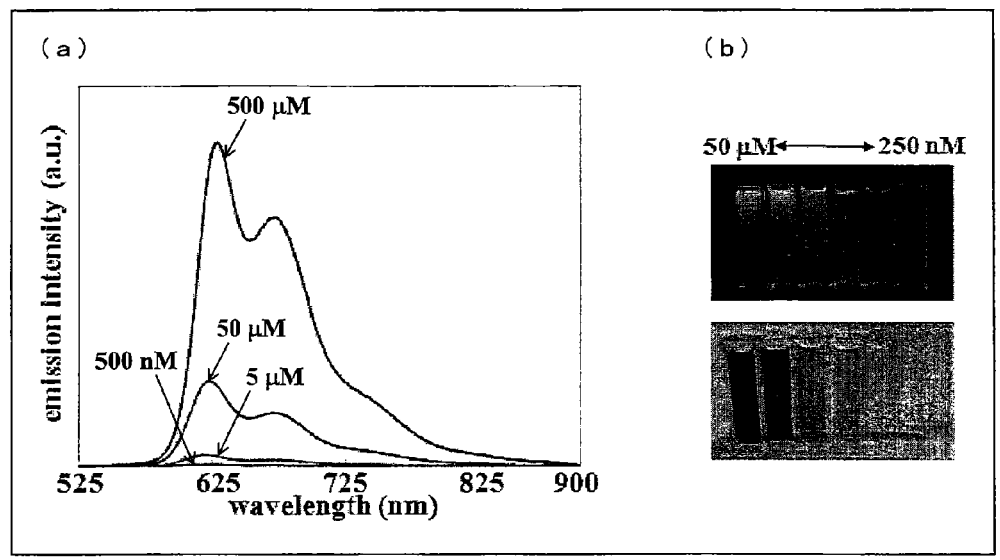
FIG. 6($a$) of FIG. 6 shows emission spectra at various concentrations of ABPX01$^+$. (b) of FIG. 6 shows appearances of the solutions: an upper photograph illustrates appearances of the solutions under 365 nm irradiation; and a bottom photograph illustrates appearances of the solutions under room light.
Figure 7:
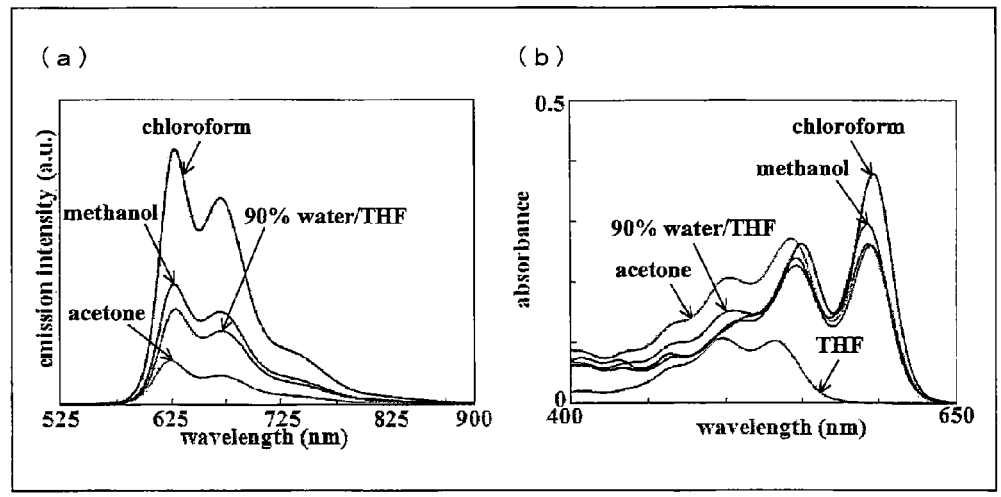
FIG. 7 shows emission and absorption spectra of ABPX01$^+$ in various solvents: (a) of FIG. 7 shows emission spectra of 500 µM of ABPX01$^+$; and (b) of FIG. 7 shows absorption spectra of 5 µM of ABPX01$^+$. 1 vol % TFA was added to ensure protonation and prevent pseudobase formation (ABPX01$^0$) during measurement.
Figure 8:
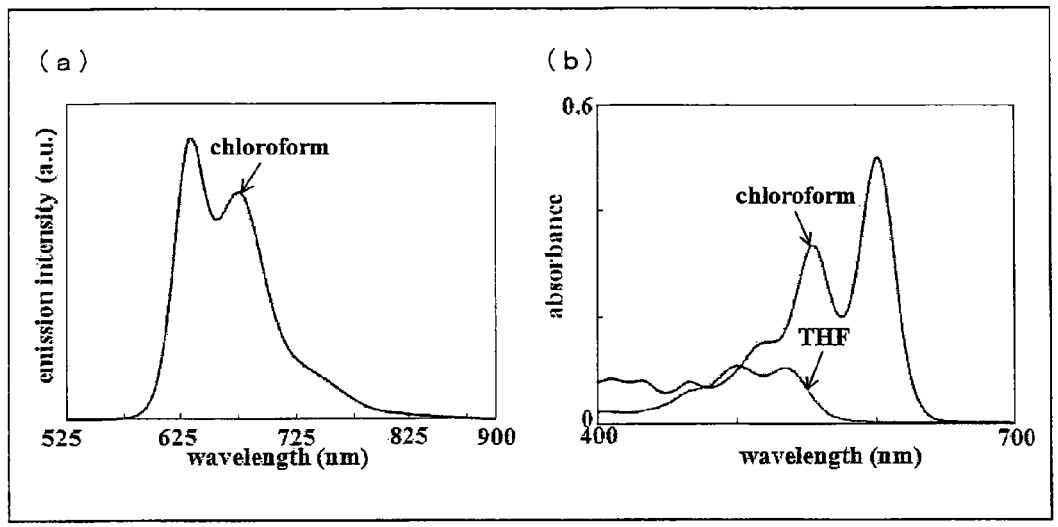
FIG. 8 shows emission and absorption spectra of ABPX02$^+$ in various solvents: (a) of FIG. 8 shows emission spectra of 500 µM of ABPX02$^+$; and (b) of FIG. 8 shows absorption spectra of 5 µM of ABPX02$^+$.
Figure 9:
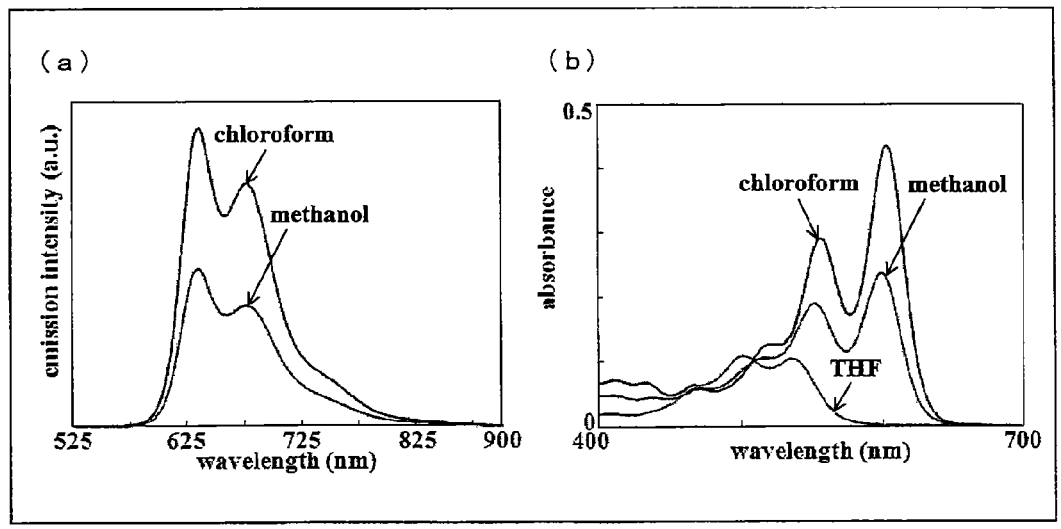
FIG. 9 shows emission and absorption spectra of ABPX03$^+$ in various solvents: (a) of FIG. 9 shows emission spectra of 500 µM of ABPX03$^+$; and (b) of FIG. 9 shows absorption spectra of 5 µM of ABPX03$^+$.
Figure 10:
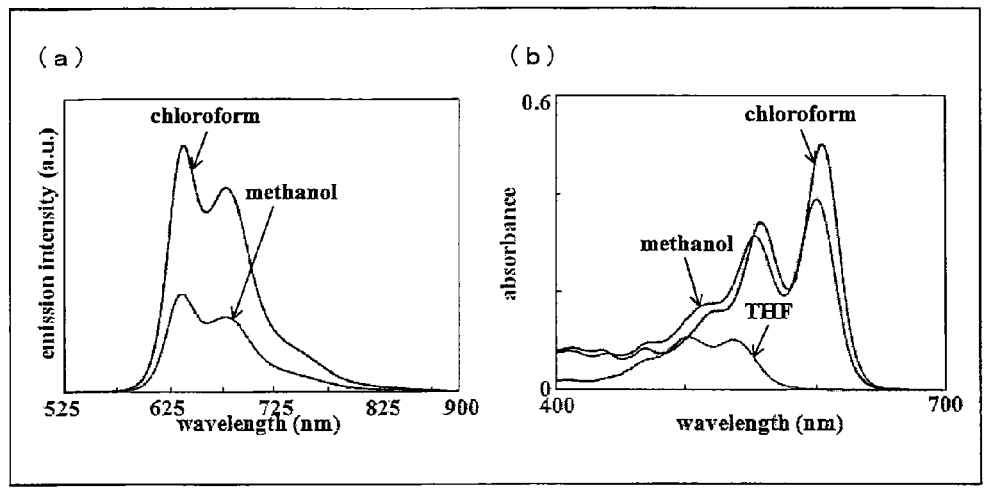
FIG. 10 shows emission and absorption spectra of ABPX04$^+$ in various solvents: (a) of FIG. 10 shows emission spectra of 500 µM of ABPX04$^+$; and (b) of FIG. 10 shows absorption spectra of 5 µM of ABPX04$^+$.

The emission spectra of ABPX01⁺ (5 μM, 50 μM, and 500 μM) dissolved in 1% TFA/methanol mixture were measured to determine whether ABPX01⁺ exhibits AIEE. The emission intensity increased as ABPX01⁺ concentration increased, as shown in FIG. 6. In contrast, the emission behavior of rhodamines in aqueous solution was reported to decrease at 10$^{-4}$ M and above because of the formation of the H-dimer. The behavior of ABPX01⁺ was directly opposite to the concentration quenching of common hydrophobic dyes.

Figure 11:
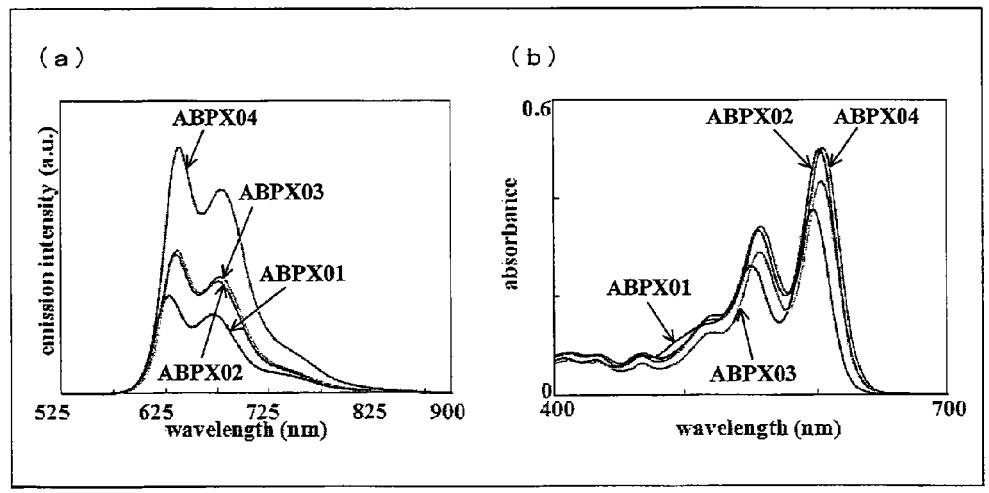
FIG. 11($a$) of FIG. 11 shows emission spectra of ABPX01$^+$ to ABPX04$^+$ in chloroform; and (b) of FIG. 11 shows absorption spectra of ABPX01$^+$ to ABPX04$^+$ in chloroform.

The AIEE characteristics of 500 μM of ABPX01⁺ to ABPX04⁺ were investigated in various solvents. Results thereof are shown in FIG. 7 to FIG. 10. In 1% TFA/chloroform, methanol, ethanol, or acetone mixtures, ABPX01⁺ were well dispersed and exhibited AIEE. The emission spectrum of 500 μM of ABPX01⁺ in THF was nonemissive. In contrast, ABPX02⁺ to ABPX04⁺ similarly showed AIEE and a slightly continuous red shift was observed with an increase in the N,N'-dialkyl chain length (FIG. 11). Marked aggregation and enhanced emission were observed in ABPX⁺ as the N-alkyl chain length was increased. These results suggested that ABPX⁺ exhibited unique AIEE and the AIEE of ABPX⁺ was driven by hydrophobic forces. ABPX⁺ showed long-wavelength emission over the near-infrared region compared with representative AIEE-active silole, anthracene, and other derivatives.

Figure 12:
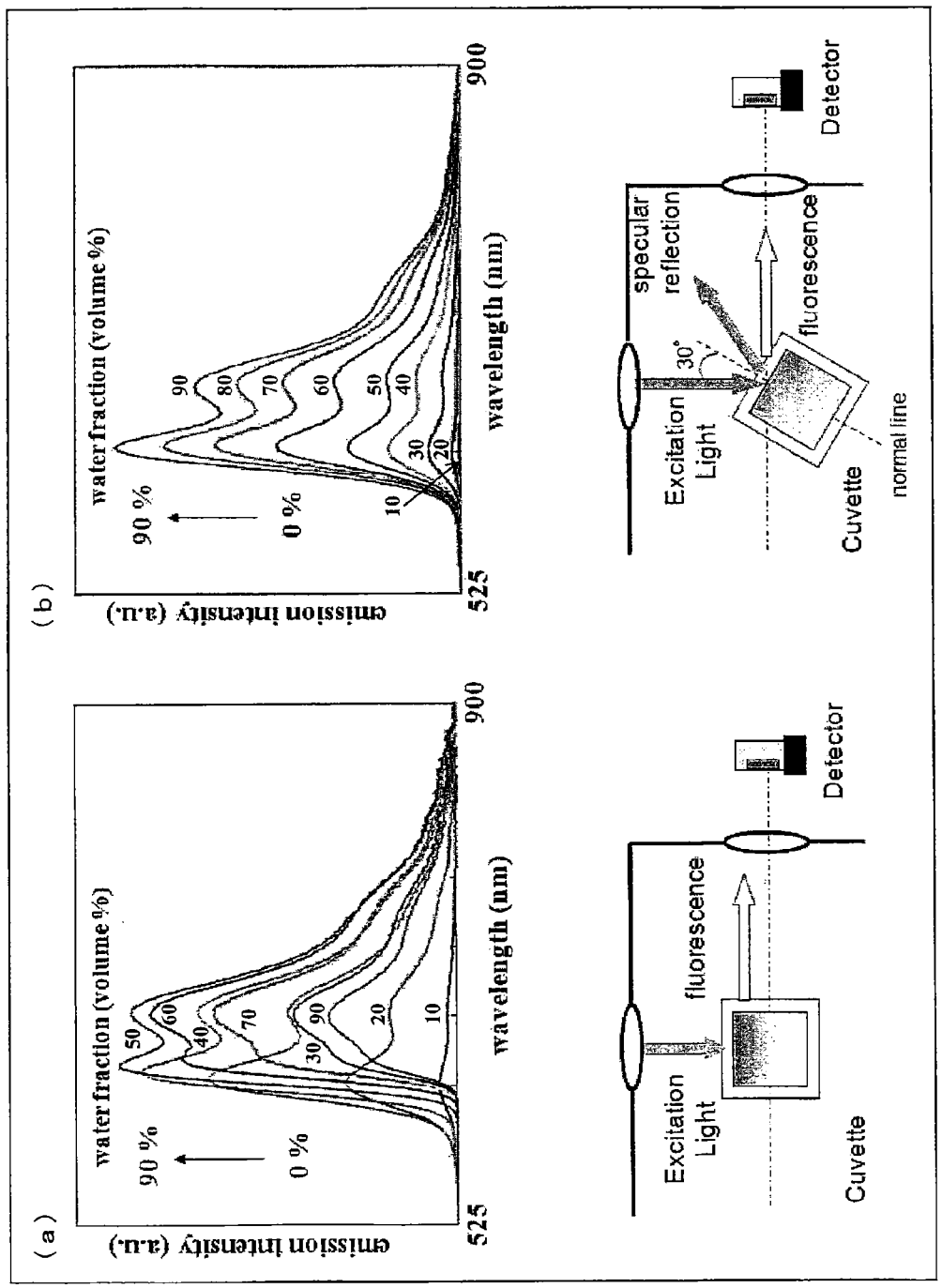
FIG. 12 shows emission spectra of ABPX01: (a) of FIG. 12 shows emission spectra of ABPX01 by a conventional photometric method; and (b) of FIG. 12 shows emission spectra of ABPX01 by a surface photometric method.

The emission spectra by a conventional photometric method showed a random shift of the maximum wavelength, which was caused by the internal shielding effect when ABPX01⁺ was measured at a high concentration. The problem was solved by using the surface photometric method (FIG. 12). Explained below are the respective surface photometric equipment configurations. The emission spectra by the conventional photometric method showed random shifts of the maximum wavelengths, which were caused by the internal filter effect when measurement of ABPX01⁺ was conducted at a high concentration. The problem was solved by using the surface photometric method. A sample holder was set at an angle of 30° with respect to the excitation light. However, attention should be paid to the linearity of the emission intensity against the concentration for the accurate evaluation of high-concentration sample solutions, such as AIEE molecules. In addition, the relative quantum yields of ABPX in solution could not be determined because of the lack of a standard compound. The use of the surface photometric method allows development of an apparatus for the measurement of the absolute fluorescence quantum yields of high-concentration solutions.

Figure 13:
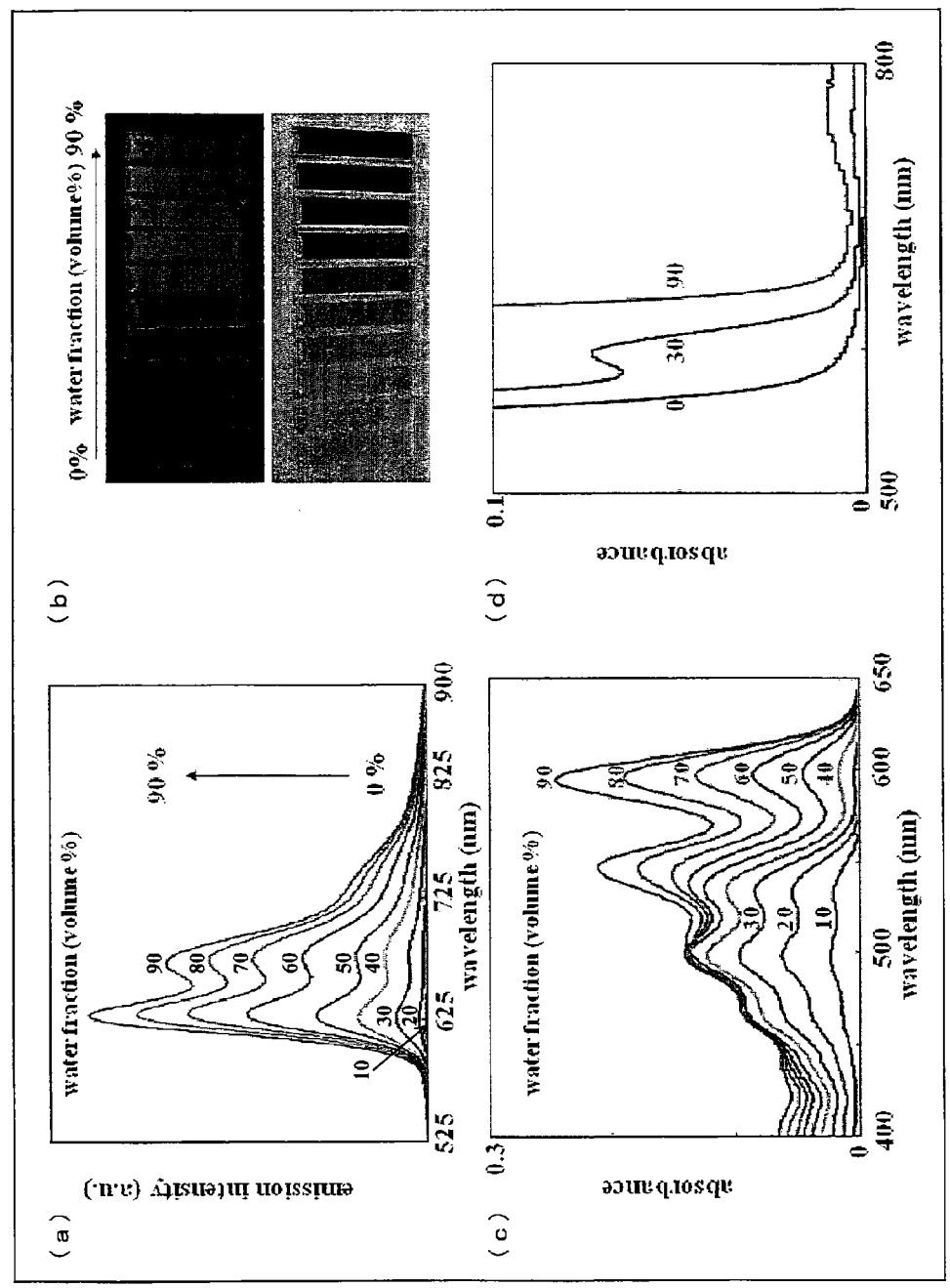
FIG. 13($a$) of FIG. 13 shows emission spectra of 500 µM of ABPX01$^+$ in water/THF mixtures by the surface photometric method. (b) of FIG. 13 shows appearances of the solutions in (a) of FIG. 13: an upper photograph illustrates appearances of the solutions under 365 nm irradiation; and a bottom photograph illustrates appearances of the solutions under room light. (c) of FIG. 13 shows absorption spectra of 5 µM of ABPX01$^+$ in water/THF mixtures. (d) of FIG. 13 shows level-off tails in 0%, 30%, and 90% water/THF mixtures owing to the Mie scattering effect. Emission and absorption spectra of ABPX01$^+$ were measured immediately after preparation.

The emission properties of ABPX01⁺ were investigated in the mixed solution of THF and water with different ratios, as ABPX01⁺ is easily dissolved in THF but not in water. The emission spectra are shown in (a) and (b) of FIG. 13. The emission could be observed when 30% volume fraction of water was added. The emission was enhanced when 50% to 90% volume fraction of water was added. Absorption measurements were similarly carried out in water/THF mixtures (containing 1% TFA). As the water fraction increased, the sharp aggregate spectra appearing at approximately 548 and 600 nm grew, as shown in (c) of FIG. 13. From 30% volume fraction of water addition, level-off tails were seen, which were attributed to Mie scattering caused by nanosized particles. ABPX01⁺ exhibits AIEE behavior and the aggregation functional photo-switching character is useful to control an on/off emission system.

The aggregation phenomena of ABPX01⁺ were confirmed by spectrophotometric analysis. Level-off tails in the visible region of the absorption spectra in methanol or water/THF mixtures clearly suggested the formation of suspended particles owing to the Mie scattering effect in (a) of FIG. 14. The tails in chloroform could not be observed although AIEE was shown in any of ABPX01⁺ to ABPX04⁺. The result indicated that the particle size of ABPX01⁺ might be different in response to solvent changes.

Figure 14:
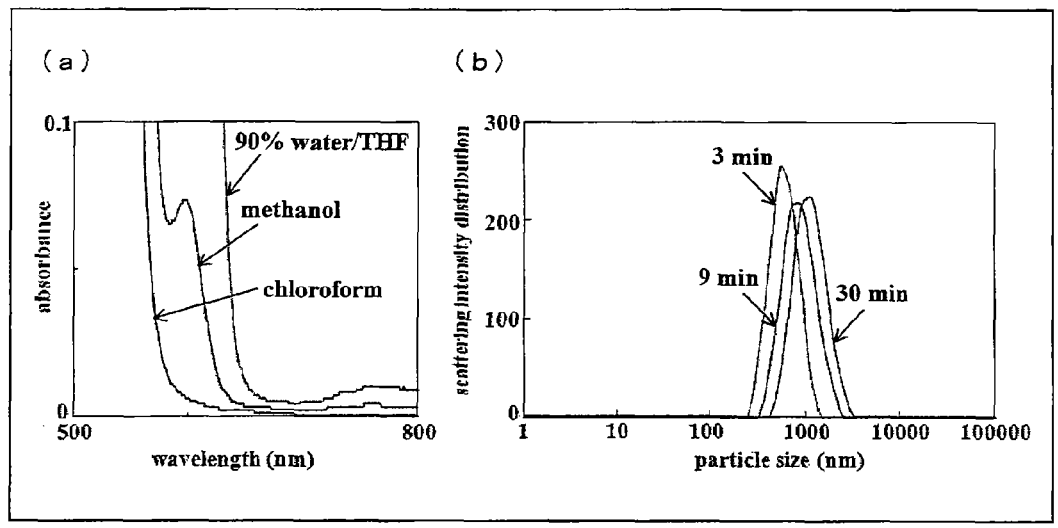
FIG. 14($a$) of FIG. 14 shows level-off tails of 500 µM of ABPX01$^+$ observed in chloroform, methanol, and 90 vol % water/THF mixture solutions. (b) of FIG. 14 shows time dependence of particle size distributions of 500 µM of ABPX01$^+$ in 90 vol % water/THF mixtures, examined by means of dynamic laser scattering.

With the use of dynamic laser scattering (DLS), the particle size of ABPX01⁺ was examined in 90% water/THF mixtures (containing 1% TFA) at 25° C. (b) of FIG. 14 shows the time dependence of the particle size distribution of 500 μM of ABPX01⁺. As illustrated in (b) of FIG. 14, the particle size of ABPX01⁺ aggregates was 500 nm immediately after the preparation of ABPX01+. The ABPX01+ aggregates then grew to a size of more than 1200 nm after 30 min. The particle size of ABPX01+ in methanol and chloroform (respectively, containing 1% TFA) could not be calculated because the fluctuation of the scattered photons was not sufficiently observed owing to the subnanometer size. These results indicated that the particle size might be dependent on the dispersion of ABPX01+ in various solvents.

Figure 15:
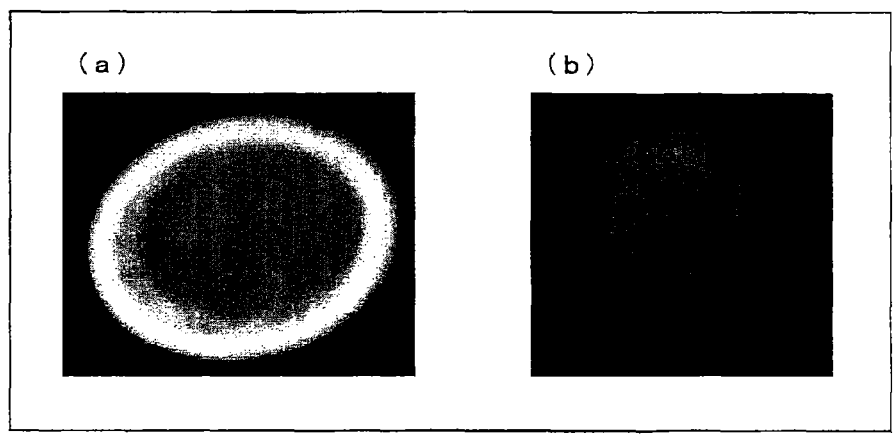
FIG. 15 shows membrane filter photographs each illustrating ABPX01$^+$ in a 90 vol % water/THF mixture (containing 1 vol % TFA) in which ABPX01$^+$ is collected by use of a membrane filter having a pore of 500 nm. (a) of FIG. 15 is a photograph of the membrane filter under room light, and (b) of FIG. 15 is a photograph of the membrane filter under 365 nm irradiation.

In order to further visualize the aggregates with emission measurements, aggregates of ABPX01+ in 90% water/THF mixtures (containing 1% TFA) were collected after 30 min using a membrane of 500 nm pore size and emission was noted under 365 nm irradiation. Results thereof are shown in FIG. 15. Evidence showing that ABPX+ possess the AIEE characteristic can be found in the above-mentioned results.

Figure 16:
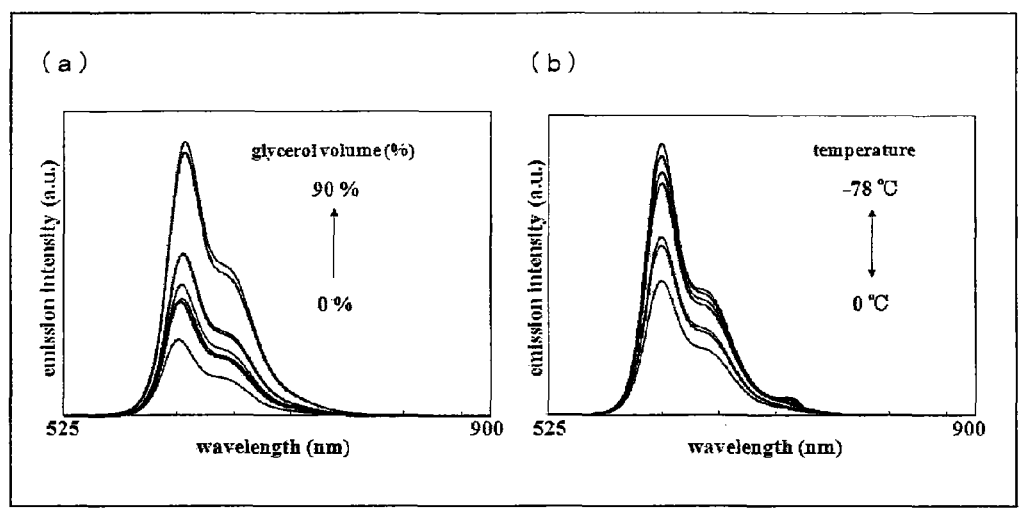
FIG. 16($a$) of FIG. 16 shows effects (viscochromism) of a composition of a glycerol/methanol mixture on emission intensity of ABPX01. (b) of FIG. 16 shows effects (thermochromism) of temperature on emission intensity of ABPX01 in methanol.
Figure 17:
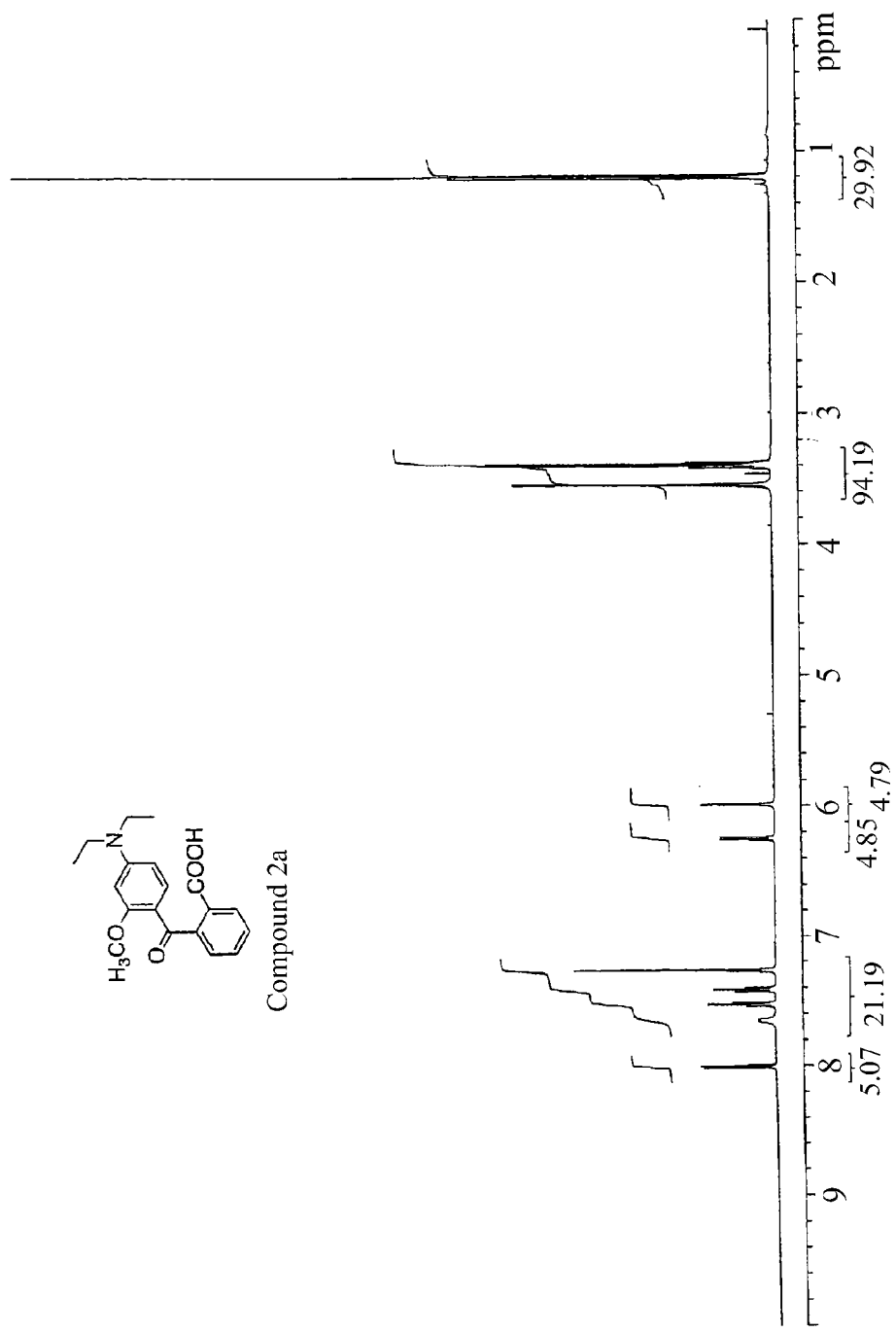
FIG. 17 shows NMR data of a benzophenone derivative "2a". Additional data associated with FIG. 17 includes, but is not limited to:
MDABP 04
Pulse Sequence: s2pul
   Solvent: CDCl3
   Ambient temperature
INOVA-500 "inova1"
   Relax. delay 3.000 sec
   Pulse 45.0 degrees
   Acq. Lime 3.500 sec
Width 7497.7 Hz
16 repetitions
OBSERVE H1, 499.5954798 MHz
DATA PROCESSING
FT size 65536
Total time 1 min. 44 sec
Figure 18:
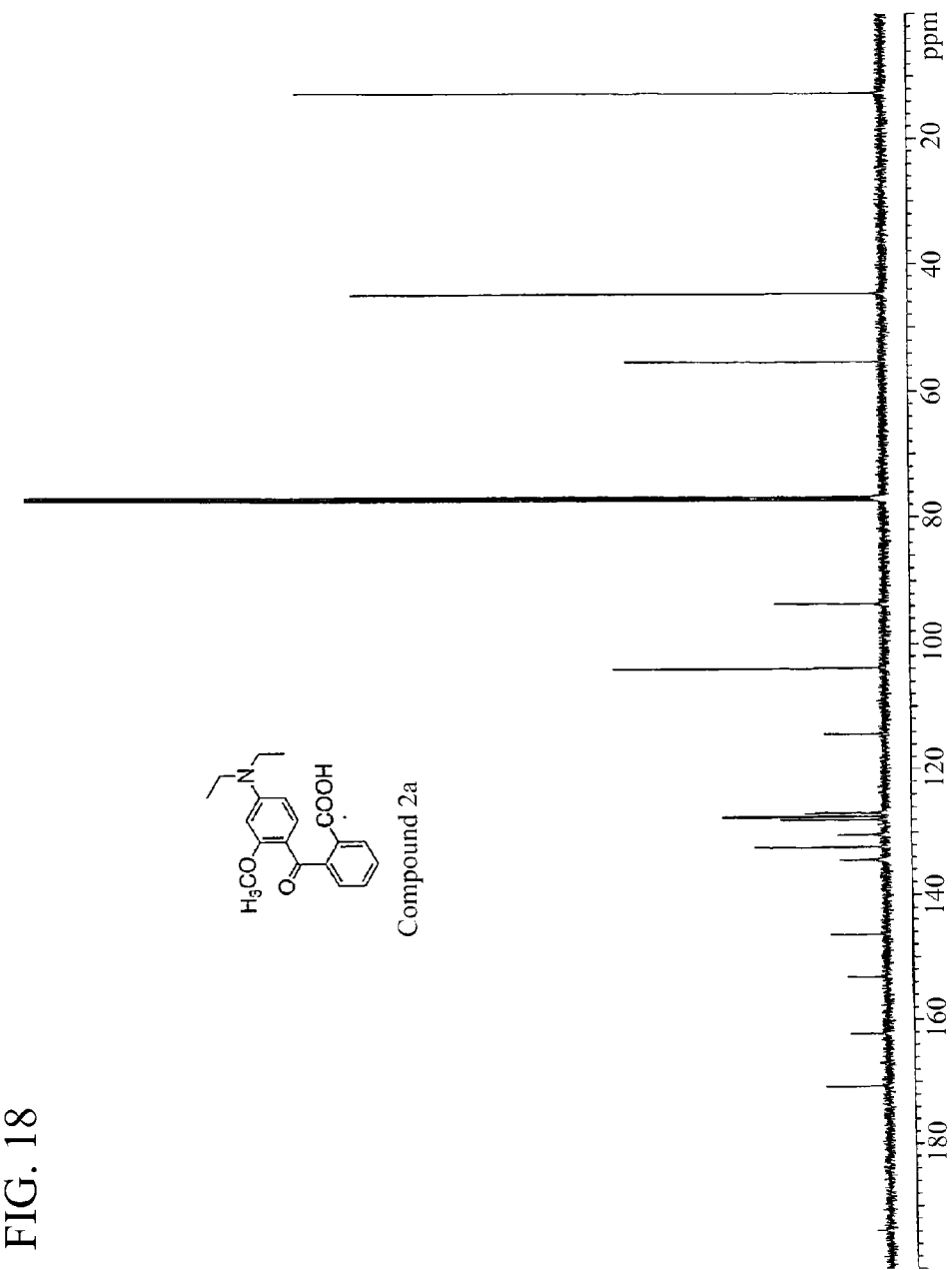
FIG. 18 shows NMR data of a benzophenone derivative "2a". Additional data associated with FIG. 18 includes, but is not limited to:
MDABP 04
Pulse Sequence s2pul
   Solvent: CDCl3
   Ambient temperature
INOVA-500 "inova1"
   Relax. delay 2.000 sec
   Pulse 45.0 degrees
   Acq. time 1.500 sec
   Width 31421.8 HZ
   1424 repetitions
OBSERVE C13, 125.6233865 MHz
DECOUPLE H1, 499.5979715 MHz
   Power 36 dB
   continuously on
   GARP-1 modulated
DATA PROCESSING
   Line broadening 1.0 Hz
FT size 131072
Total time 9 hr, 44 min, 49 sec
Figure 19:
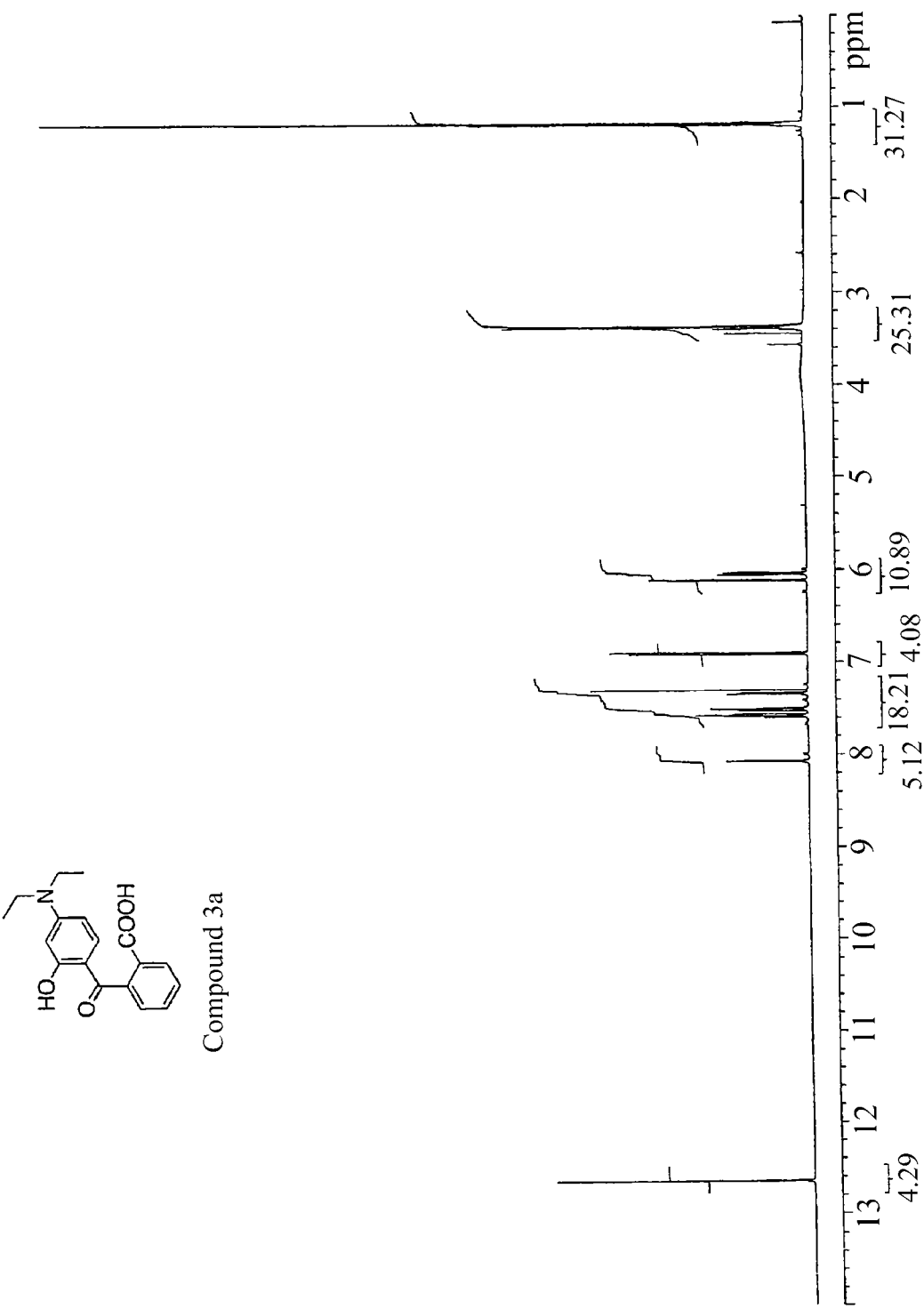
FIG. 19 shows NMR data of a benzophenone derivative "3a" Additional data associated with FIG. 19 includes, but is not limited to:
HDABP 04
Pulse Sequence: s2pul
   Solvent: CDCl3
   Ambient temperature
INOVA-500 "inova1"
   Relax. delay 2.000 sec
   Pulse 45.0 degrees
   Acq. time 3.500 sec
   Width 7497.7 Hz
   16 repetitions
OBSERVE H1, 499.5954002 MHz
DATA PROCESSING
   FT size 65536
Total time 1 min, 28 sec
Figure 20:
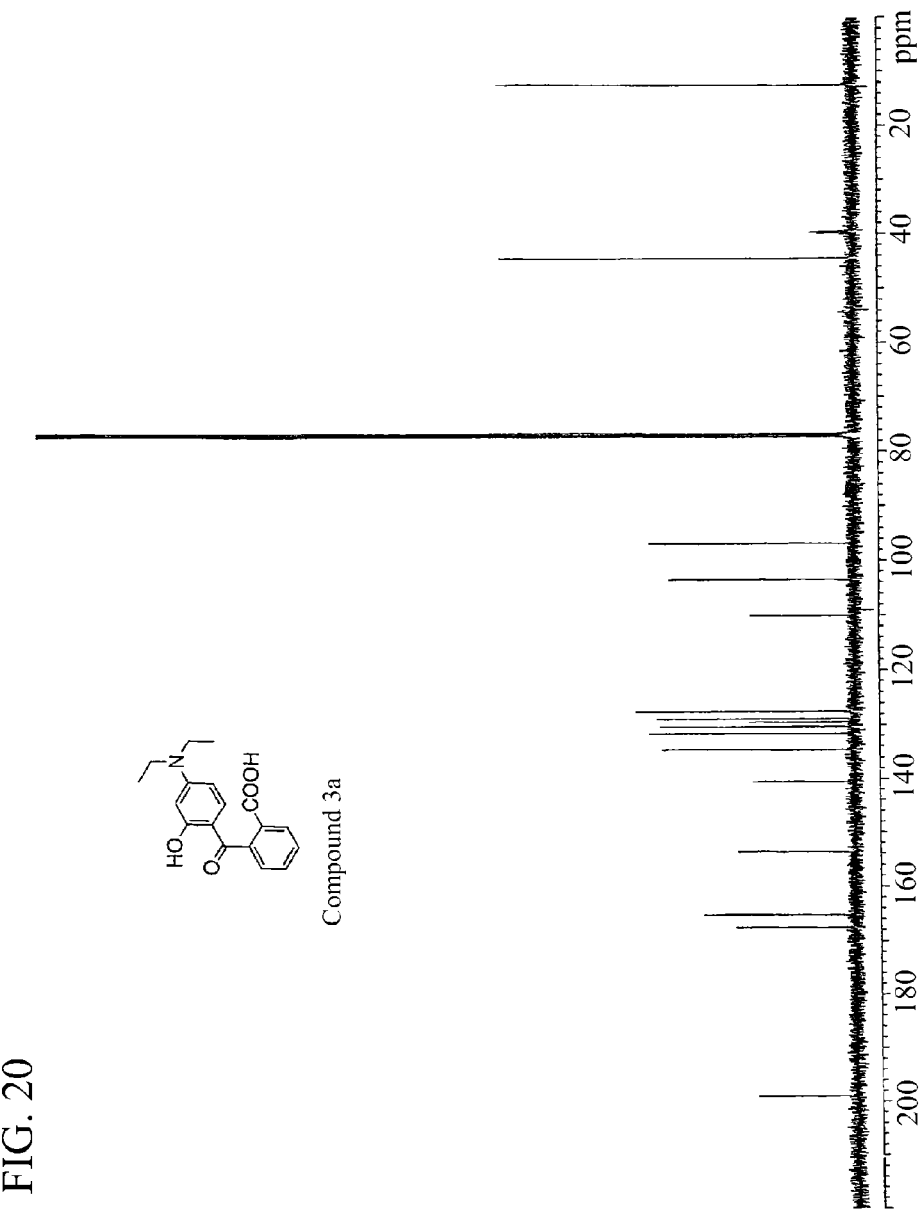
FIG. 20 shows NMR data of a benzophenone derivative "3a". Additional data associated with FIG. 20 includes, but is not limited to:
HDABP 04
Pulse Sequence: s2pul
   Solvent; CDCl3
   Ambient temperature
INOVA-500 "inova1"
   Relax. delay 2.000 sec
   Pulse 45.0 degrees
   Acq. time 1.500 sec
   Width 31421.8 Hz
   544 repetitions
OBSERVE C13, 125.6233941 MHz
DECOUPLE H1, 499.5979715 MHz
   Power 36 dB
   continuously on
   GARP-1 modulated
DATA PROCESSING
   Line broadening 1.0 Hz
FT size 131072
Total time 9 hr, 44 min, 43 sec
Figure 21:
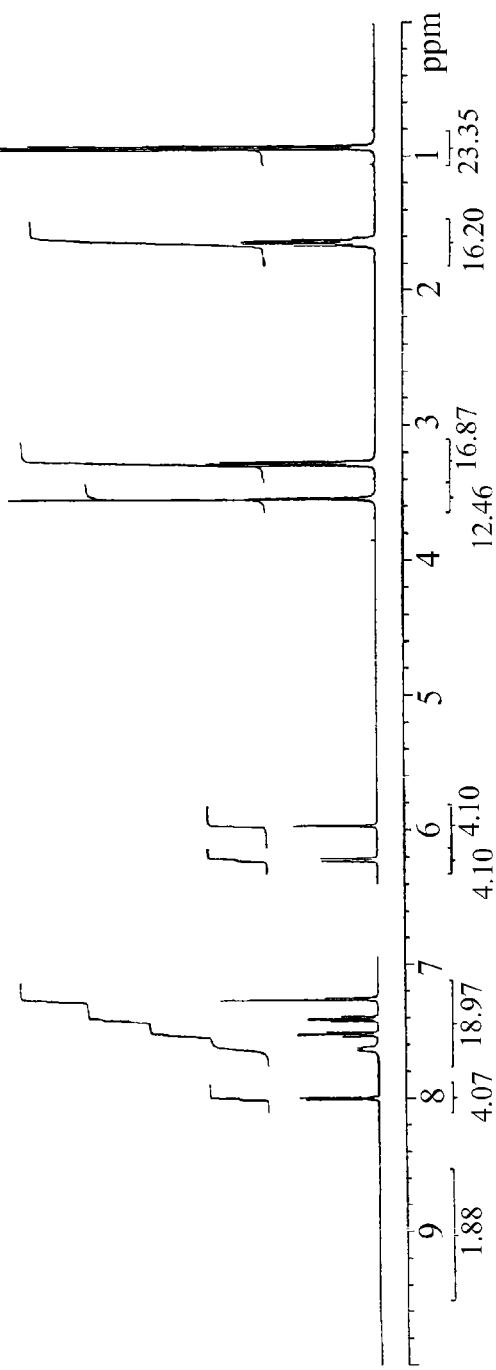
FIG. 21 shows NMR data of a benzophenone derivative "2b". Additional data associated with FIG. 21 includes, but is not limited to:
OLM02-C3
Pulse Sequence: s2pul
   Solvent; CDCl3
   Ambient temperature
INOVA-500 "inova1"
   Relax. delay 2.000 sec
   Pulse 45.0 degrees
   Acq. time 3.500 sec
   Width 7497.7 Hz
   16 repetitions
OBSERVE H1, 499.5726794 MHz
DATA PROCESSING
FT size 65536
Total time 1 min, 28 sec
Figure 22:
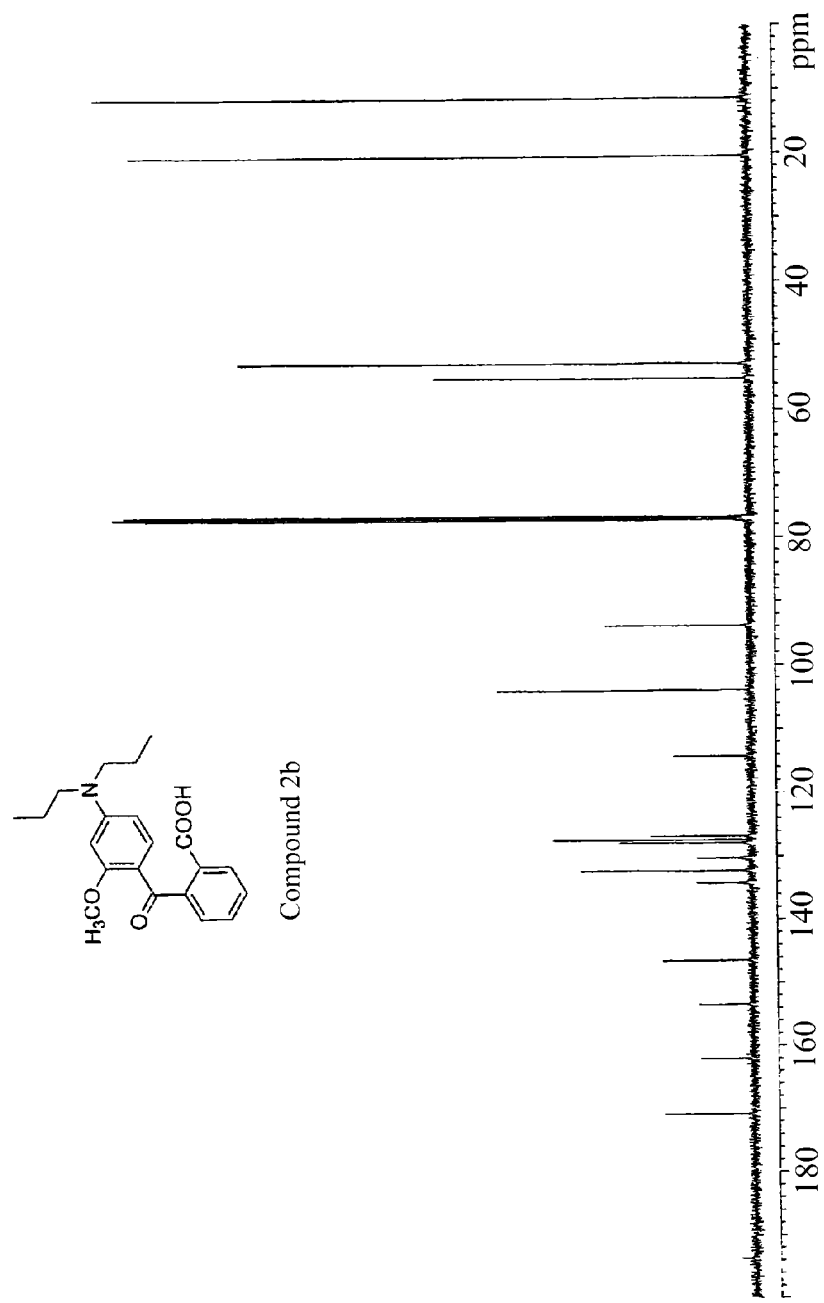
FIG. 22 shows NMR data of a benzophenone derivative "2b". Additional data associated with FIG. 22 includes, but is not limited to:
OLM02-C3
Pulse Sequence: s2pul
   Solvent: CDCl3
   Ambient temperature
INOVA-500 "inova1"
   Relax. delay 2.000 sec
   Pulse 45.0 degrees
   Acq. time 1.500 sec
   Width 31121.0 Hz
   592 repetitions
OBSERVE C13, 125.6176582 MHz
DECOUPLE H1, 499.5751711 MHz
   Power 86 dB
   continuously on
   GARP-1 modulated
DATA PROCESSING
   Line broadening 1.0 Hz
FT Size 191072
Total time 9 hr, 44 min, 49 sec
Figure 23:
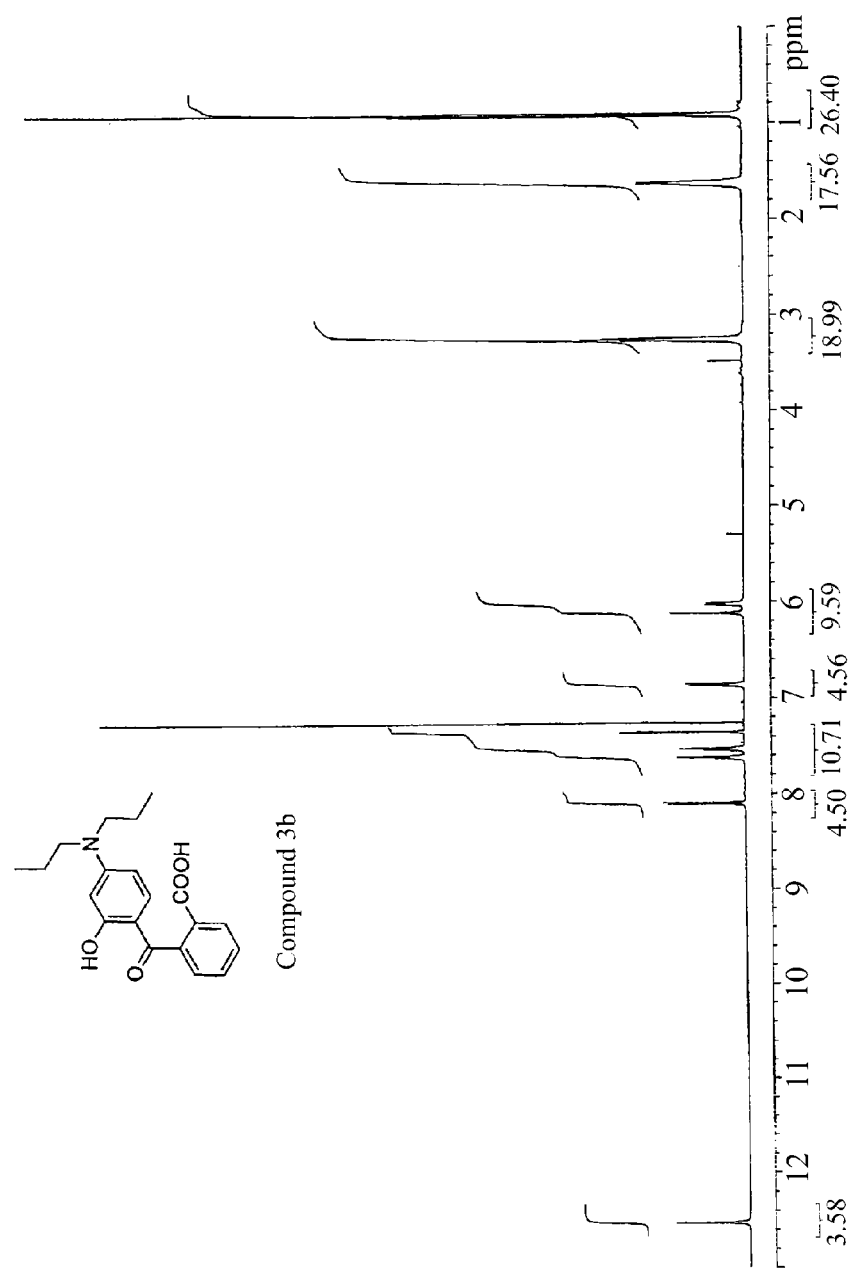
FIG. 23 shows NMR data of a benzophenone derivative "3b". Additional data associated with FIG. 23 includes, but is not limited to:
OLM02-C4
Pulse Sequence; s2pul
   Solvent: CDCl3
   Ambient temperature
INOVA-500: "inova1"
   Relax. delay 2.000 sec
   Pulse 45.0 degrees
   Acq. time 3.500 sec
   Width 7497.7 Hz
   32 repetitions
OBSERVE H1, 499.5726803 MHz
DATA PROCESSING
FT size 65536
Total time 2 min, 56 sec
Figure 24:
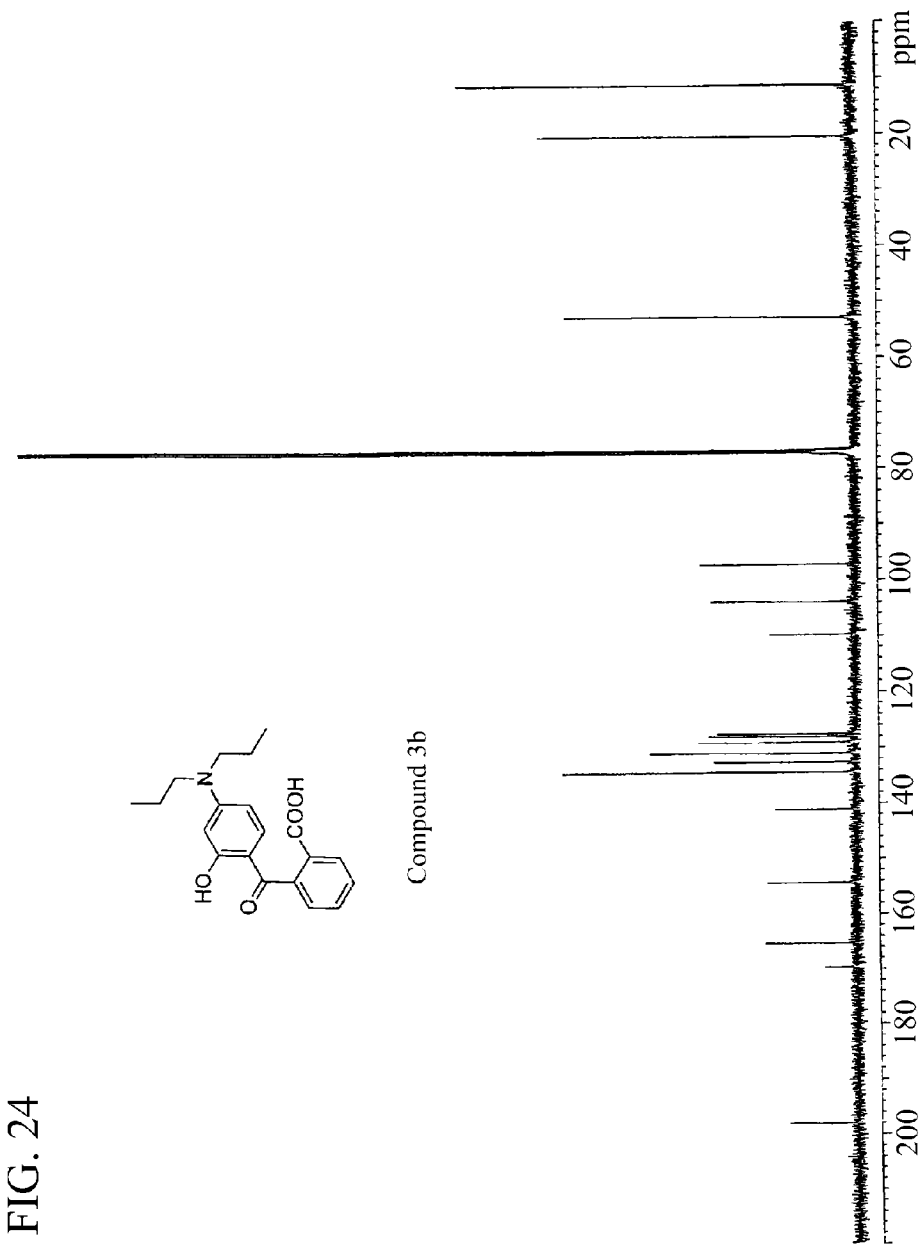
FIG. 24 shows NMR data of a benzophenone derivative "3b". Additional data associated with FIG. 24 includes, but is not limited to:
OLM02-C4
Pulse Sequence; s2pul
   Solvent: CDCl3
   Ambient temperature
INOVA-500 "inova1"
   Relax. delay 2.000 sec
   Pulse 45.0 degrees
   Acq. time 1.500 sec
   Width 31421.8 Hz
   10000 repetitions
OBSERVE C13, 125.6176509 MHz
DECOUPLE H1, 499.5751711 MHz
   Power 36 dB
   continuously on
   GARP-1 modulated
DATA PROCESSING
   Line broadening 1.0 Hz
FT size 131072
Total time 9 hr, 44 min, 49 sec
Figure 25:
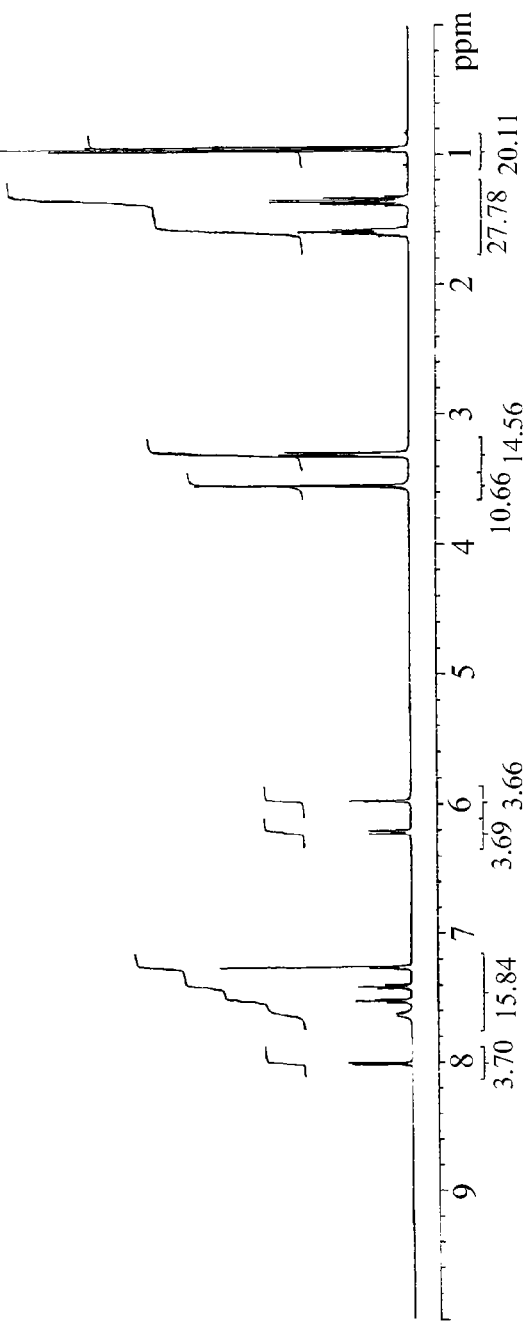
FIG. 25 shows NMR data of a benzophenone derivative "2c". Additional data associated with FIG. 25 includes, but is not limited to:
OLM03-C3
Pulse Sequence: s2pul
   Solvent: CDCl3
   Ambient temperature
INOVA-500 "inova1"
   Relax. delay 2.000 sec
   Pulse 45.0 degrees
   Acq. time 3.500 sec
   Width 7497.7 Hz
   16 repetitions
OBSERVE H1, 499.5726801 MHz
DATA PROCESSING
FT size 65538
Total time 1 min, 28 sec
Figure 26:
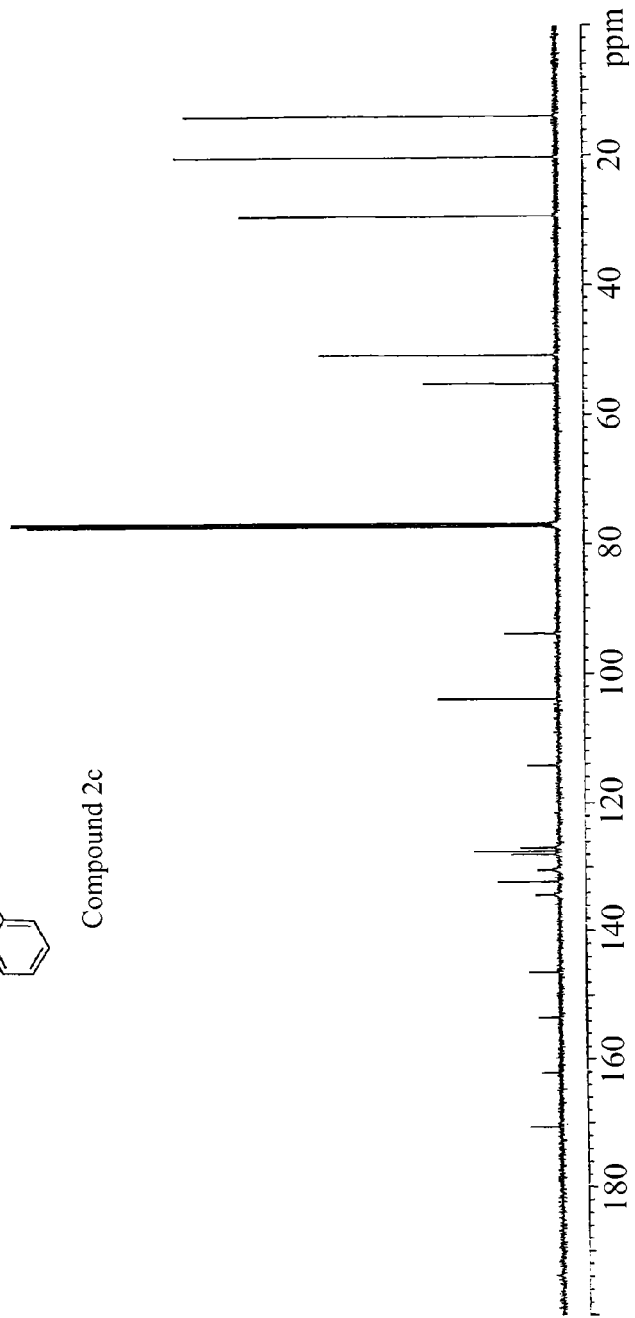
FIG. 26 shows NMR data of a benzophenone derivative "2c". Additional data associated with FIG. 26 includes, but is not limited to:
OLM03-C3
Pulse Sequence: s2pul
  Solvent: CDCl3
  Ambient temperature
INOVA-500 "inova1"
  Relax. delay 2.000 sec
  Pulse 45.0 degrees
  Acq. time 1.500 sec
  Width 31421.8 Hz
  944 repetitions
OBSERVE C13, 125.6176533 MHz
DECOUPLE H1, 499.5751711 MHz
  Power 36 dB
  continuously on
  GARP-1 modulated
DATA PROCESSING
  Line broadening 1.0 Hz
FT size 131072
Total time 9 hr, 44 min, 49 sec
Figure 27:
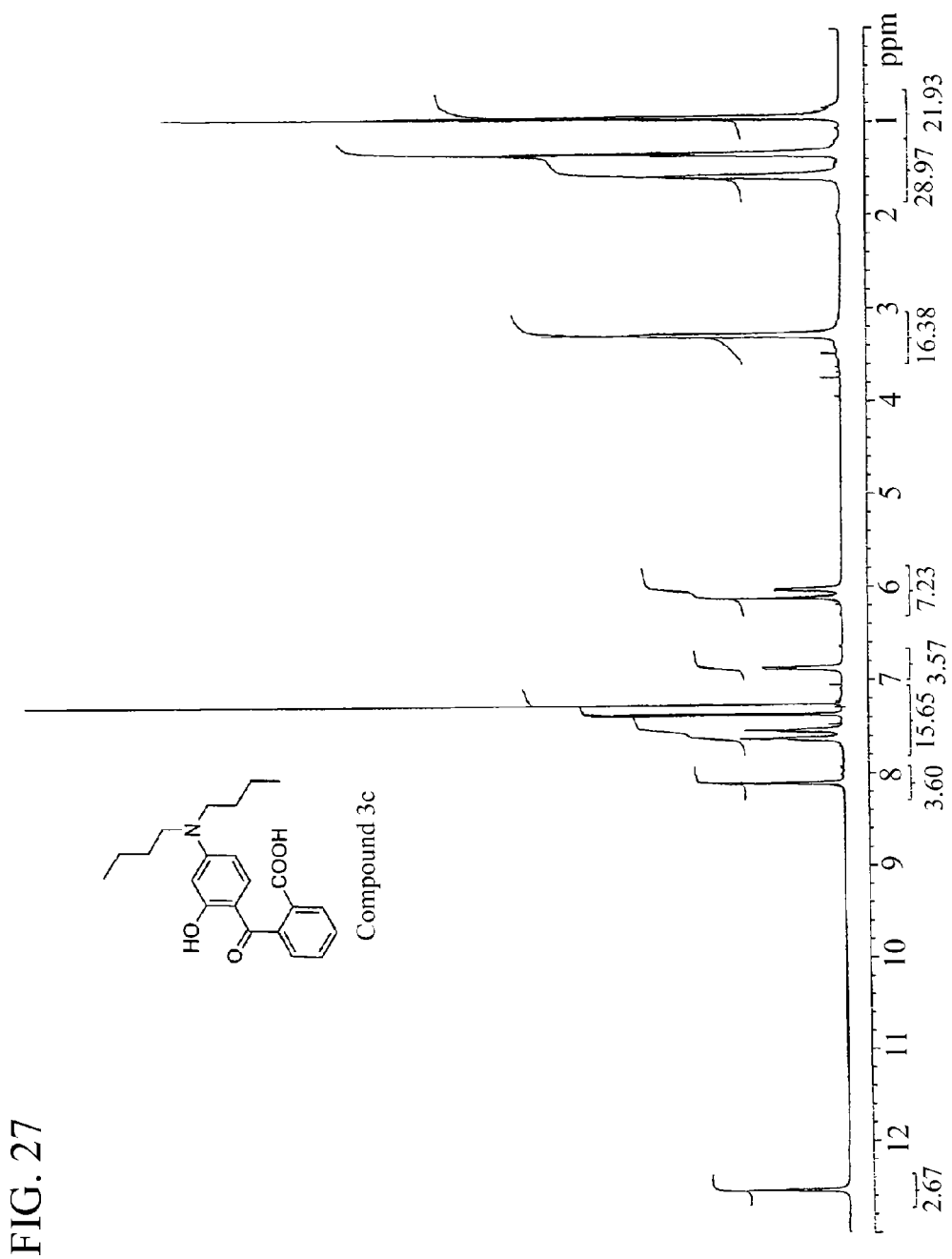
FIG. 27 shows NMR data of a benzophenone derivative "3c". Additional data associated with FIG. 27 includes, but is not limited to:
OLM03-C4
Pulse Sequence: s2pul
  Solvent: CDCl3
  Ambient temperature
INOVA-500 "inova1"
  Relax. delay 2.000 sec
  Pulse 45.0 degrees
  Acq. time 3.500 see
  Width 7497.7 Hz
  32 repetitions
OBSERVE H1, 499.5726797 MHz
DATA PROCESSING
FT size 65536
Total time 2 min, 56 sec
Figure 28:
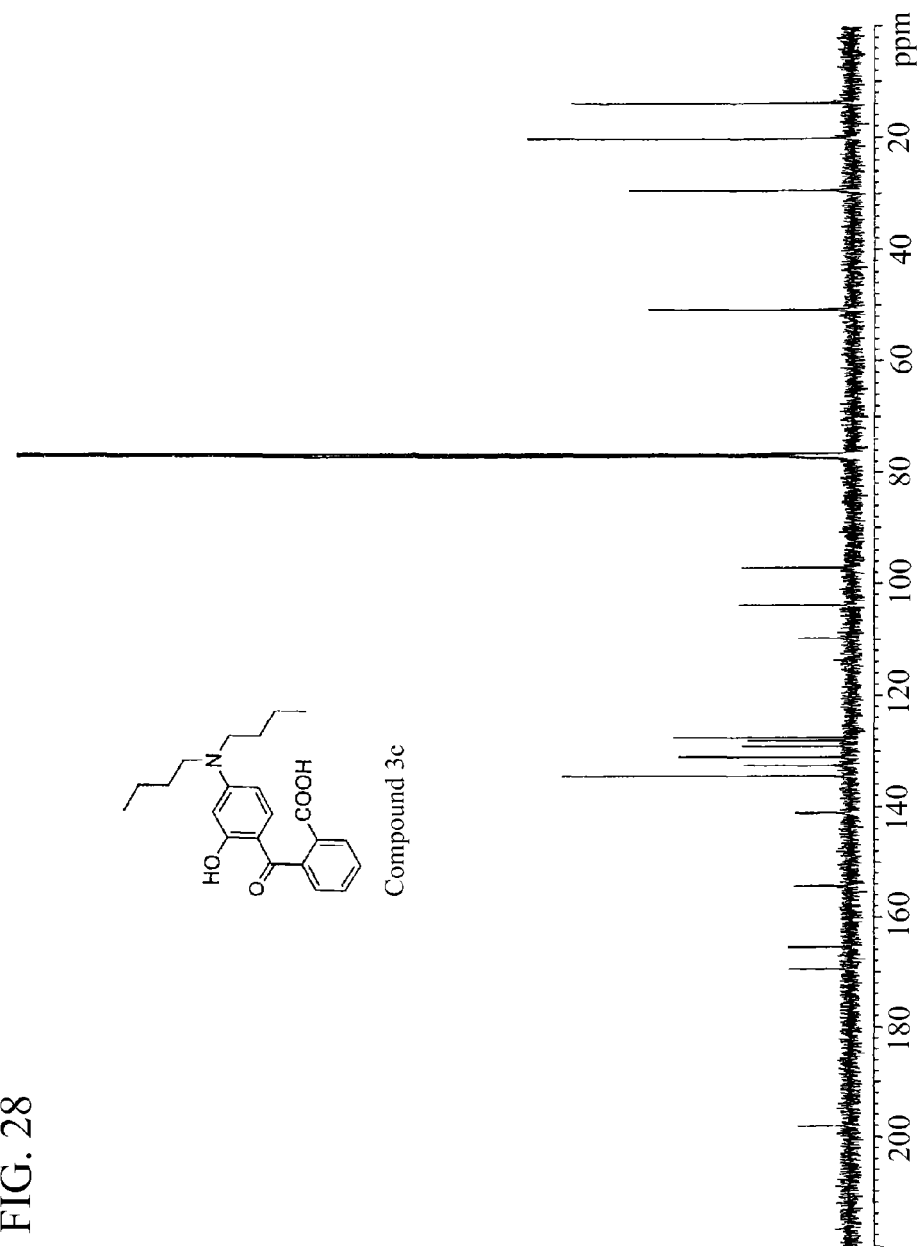
FIG. 28 shows NMR data of a benzophenone derivative "3c". Additional data associated with FIG. 28 includes, but is not limited to:
OLM03-C4
Pulse Sequence: s2pul
  Solvent: CDCl3
  Ambient temperature
INOVA-500 "inova1"
  Relax, delay 2.000 sec
  Pulse 45.0 degrees
  Acq. time 1.500 sec
  Width 31421.8 Hz
  7792 repetitions
OBSERVE C13, 125.6176499 MHz
DECOUPLE H1, 499.5751711 MHz
  Power 36 dB
  continuously on
  GARP-1 modulated
DATA PROCESSING
  Line broadening 1.0 Hz
FT size 131072
Total time 15 hr, 35 min, 43 sec
Figure 29:
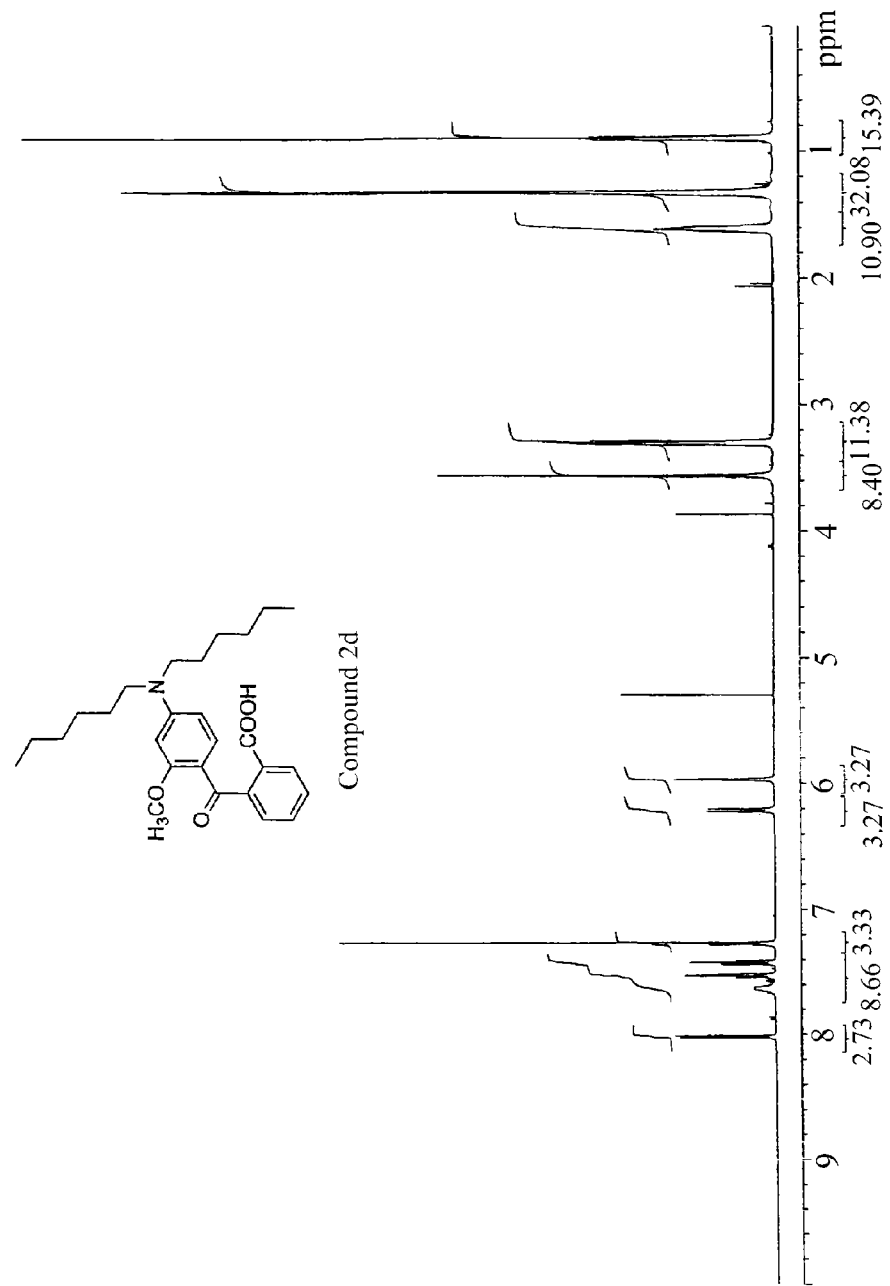
FIG. 29 shows NMR data of a benzophenone derivative "2d". Additional data associated with FIG. 29 includes, but is not limited to:
C3 OFL06
Pulse Sequence: s2pul
  Solvent: CDCl3
  Ambient temperature
File: H1sw
INOVA-500 "inova1"
  Relax. delay 2.000 sec
  Pulse 45.0 degrees
  Acq. time 3.500 sec
  Width 7497.7 Hz
  16 repetitions
OBSERVE H1, 499.5954791 MHz
DATA PROCESSING
FT size 65536
Total time 1 min, 28 sec
Figure 30:
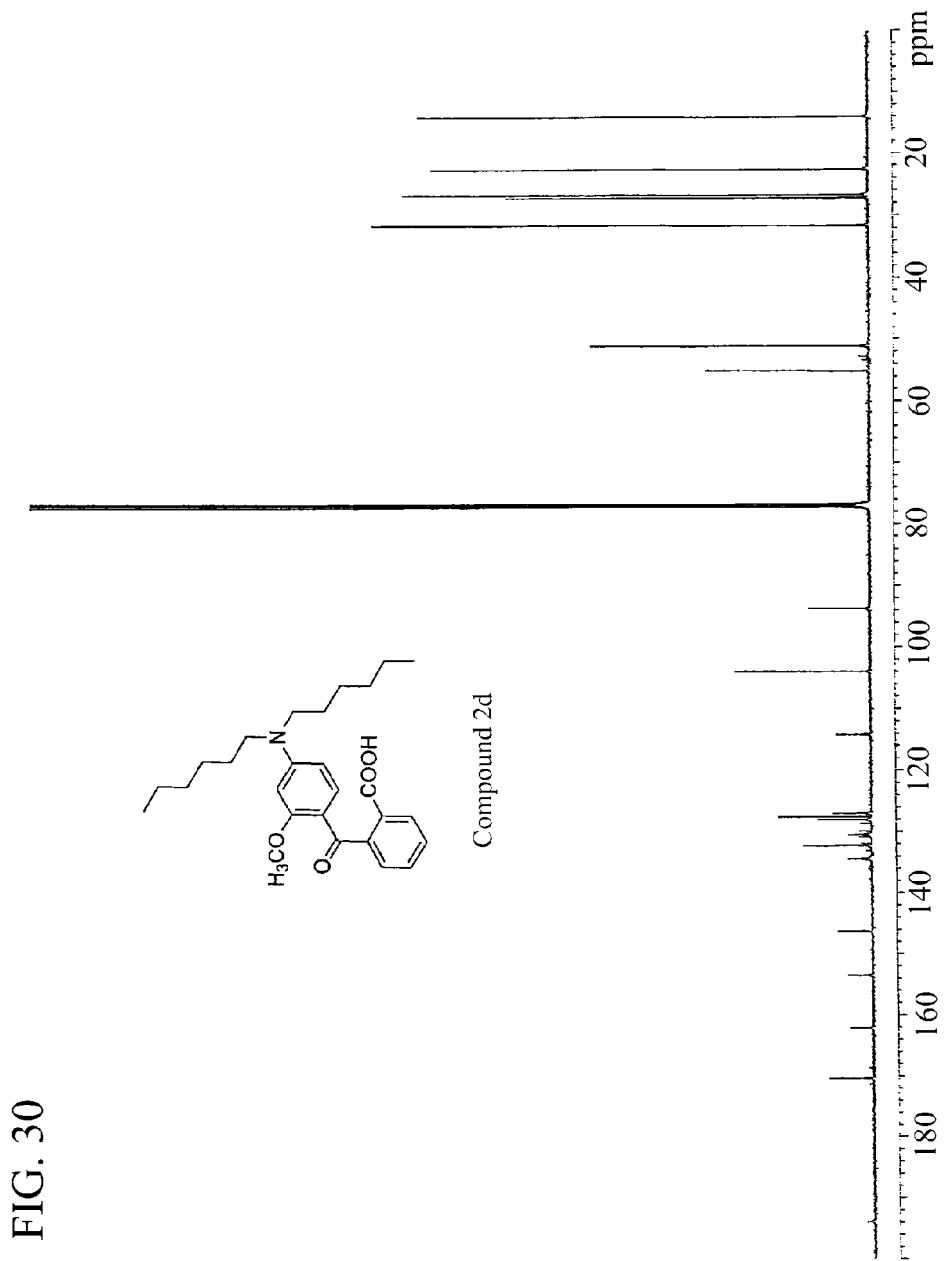
FIG. 30 shows NMR data of a benzophenone derivative "2d". Additional data associated with FIG. 30 includes, but is not limited to:
C3 OFL06
Pulse Sequence: s2 pul
  Solvent: CDCl3
  Ambient temperature
File: C13
INOVA-500 "inova1"
  Relax. delay 2.000 sec
  Pulse 45.0 degrees
  Acq. time 1.500 sec
  Width 31421.8 Hz
  8240 repetitions
OBSERVE C13, 125.8233850 MHz
DECOUPLE H1, 499.5979715 MHz
  Power 26 dB
  continuously on
  GARP-1 modulated
DATA PROCESSING
  Line broadening 1.0 Hz
FT size 131072
Total time 19 hr, 29 min, 39 sec
Figure 31:
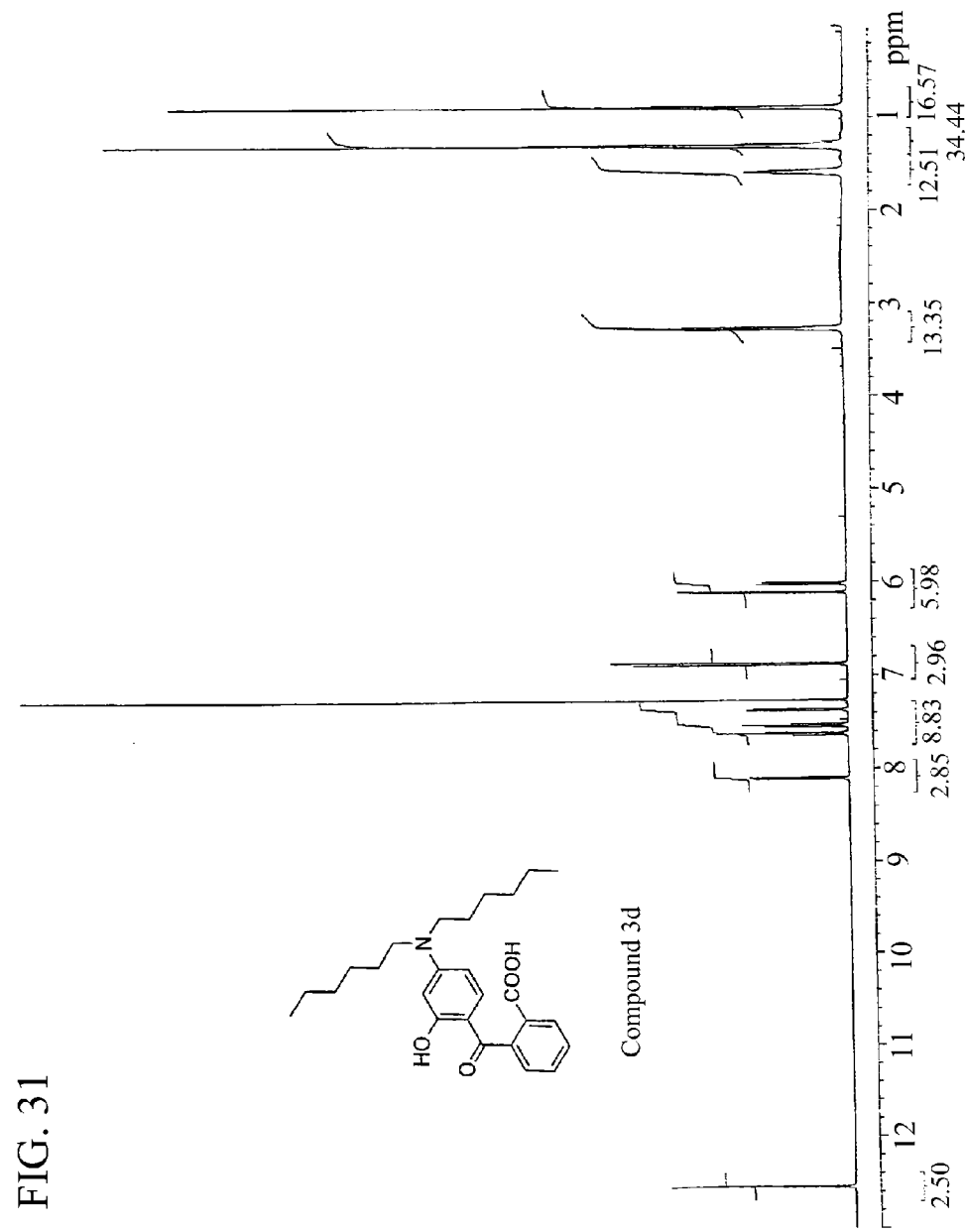
FIG. 31 shows NMR data of a benzophenone derivative "3d". Additional data associated with FIG. 31 includes, but is not limited to:
C4 OLM04
Pulse Sequence: s2 pul
  Solvent: CDCl3
  Ambient temperature
INOVA-500 "inova1"
  Relax. delay 2.000 sec
  Pulse 45.0 degrees
  Acq. time 1.500 sec
  Width 7497.7 Hz
  16 repetitions
OBSERVE H1, 499.5661719 MHz
DATA PROCESSING
FT size 65536
Total time 1 min, 28 sec
Figure 32:
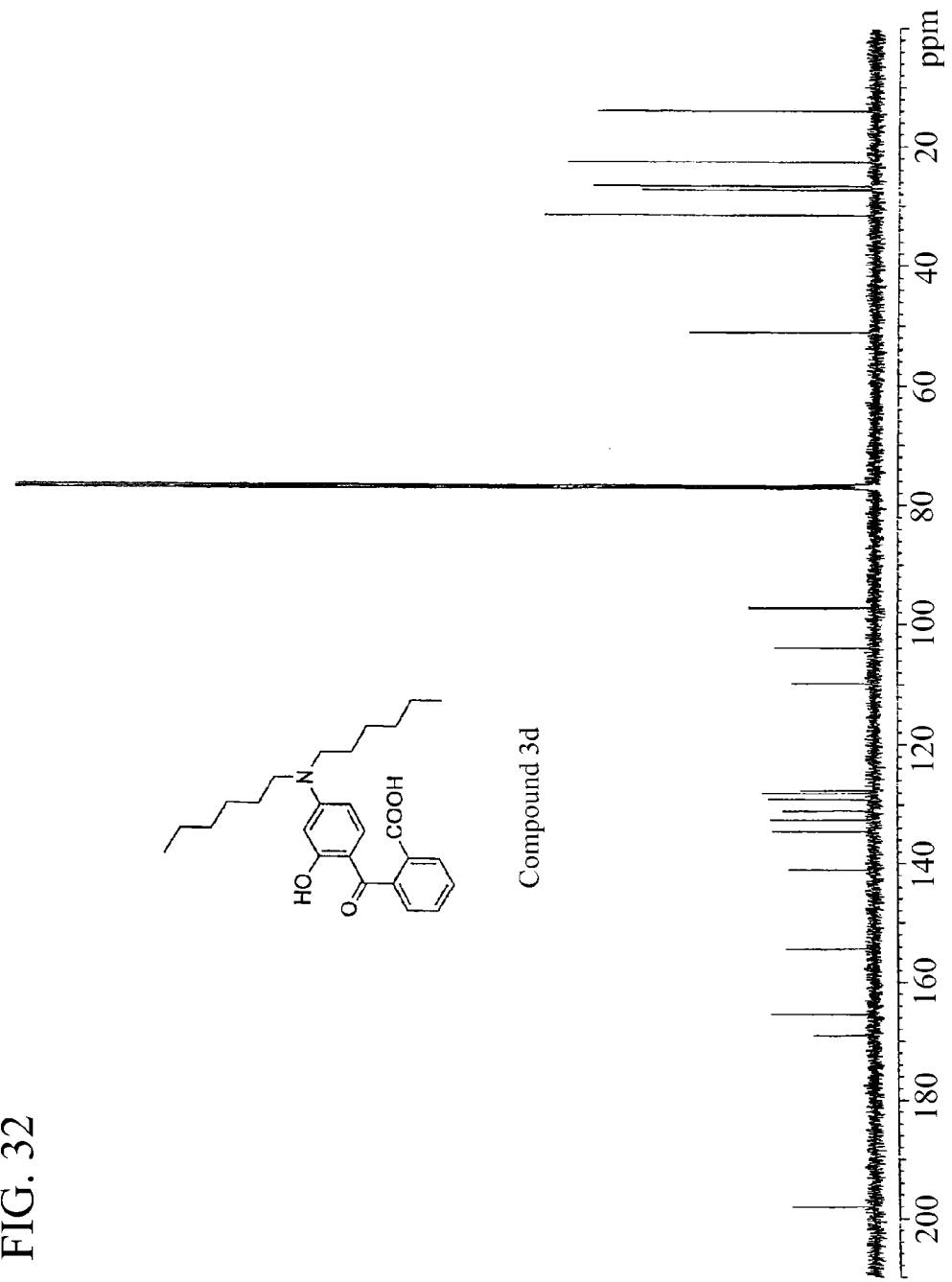
FIG. 32 shows NMR data of a benzophenone derivative "3d". Additional data associated with FIG. 32 includes, but is not limited to:
C4 OLM04
Pulse Sequence: s2 pul
  Solvent: CDCl3
  Ambient temperature
INOVA-500 "inova1"
  Relax. delay 2.000 sec
  Pulse 45.0 degrees
  Acq. time 1.500 sec
  Width 31421.8 Hz
  3264 repetitions
OBSERVE C13, 125.8160138 MHz
DECOUPLE H1, 499.5686567 MHz Power 36 dB
  continuously on
  GARP-1 modulated
DATA PROCESSING
  Line broadening 1.0 Hz
FT size 131072
Total time 9 hr, 44 min, 49 sec
Figure 33:
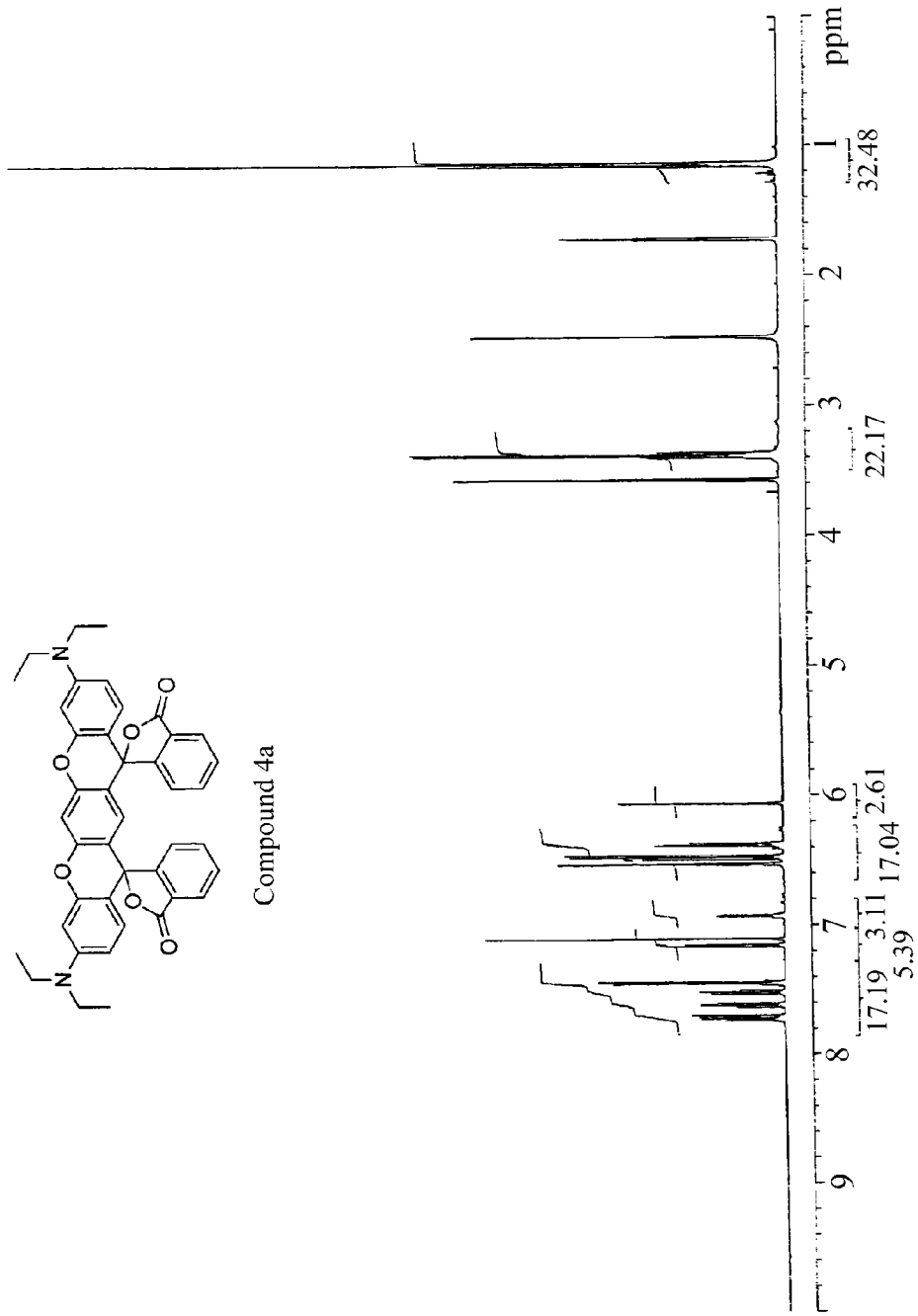
FIG. 33 shows NMR data of a compound "4a" (ABPX01). Additional data associated with FIG. 33 includes, but is not limited to:
OLM01
in THF
100624
Pulse Sequence: s2 pul
  Solvent: Acetone
  Ambient temperature
File: H1sw
INOVA-500 "inova1"
  Relax. delay 2.000 sec
  Pulse 45.0 degrees
  Acq. time 3.500 sec
  Width 7497.7 Hz
  16 repetitions
OBSERVE H1, 499.5754425 MHz
DATA PROCESSING
FT size 65536
Total time 1 min, 28 sec
Figure 34:
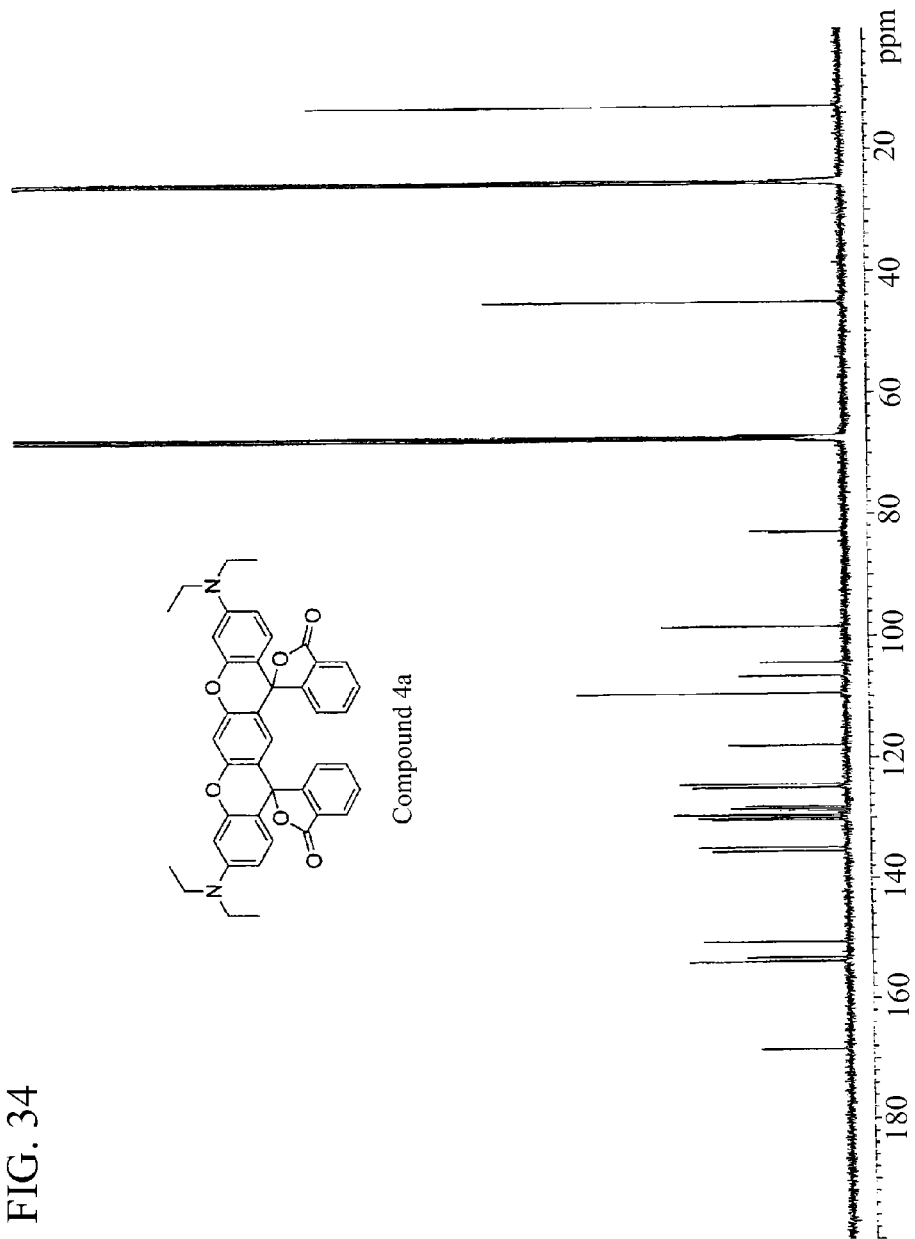
FIG. 34 shows NMR data of a compound "4a" (ABPX01). Additional data associated with FIG. 34 includes, but is not limited to:
OLM01
in THF
100624
Pulse Sequence: s2 pul
  Solvent: Acetone
  Ambient temperature
File: C13
INOVA-500 "inova1"
  Relax. delay 2.000 sec
  Pulse 45.0 degrees
  Acq. time 1.500 sec
  Width 31421.8 Hz
  3584 repetitions
OBSERVE C13, 125.6182185 MHz
DECOUPLE H1, 499.5777630 MHz
  Power 36 dB
  continuously on
  GARP-1 modulated
DATA PROCESSING
  Line broadening 1.0 Hz
FT size 131072
Total time 9 hr, 44 min, 49 sec
Figure 35:
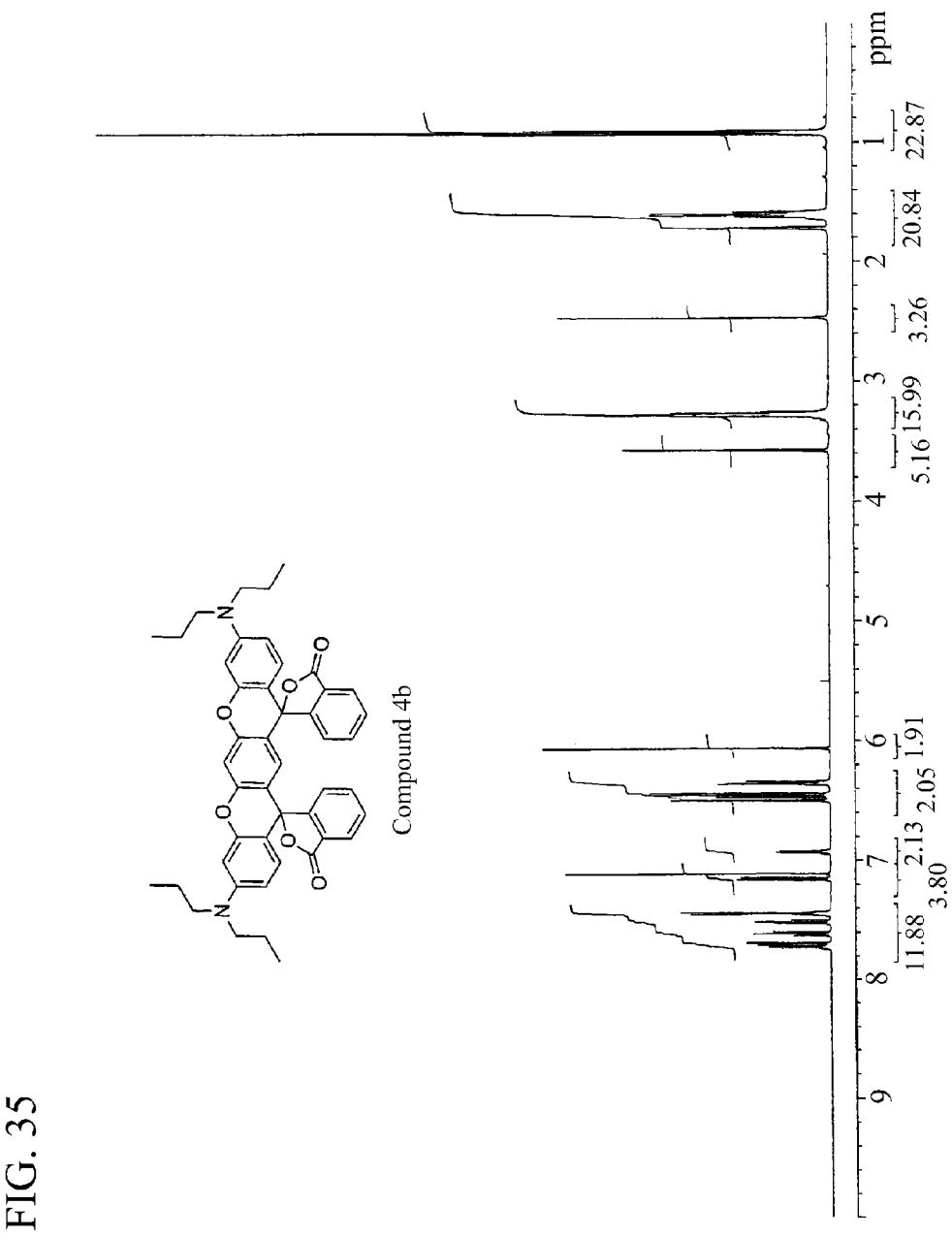
FIG. 35 shows NMR data of a compound "4b" (ABPX02). Additional data associated with FIG. 35 includes, but is not limited to:
OLM02
Pulse Sequence: s2 pul
  Solvent: Acetone
  Ambient temperature
INOVA-500 "inova1"
  Relax. delay 2.000 sec
  Pulse 45.0 degrees
  Acq. time 3.500 sec
  Width 7497.7 Hz
  32 repetitions
OBSERVE H1, 499.5754436 MHz
DATA PROCESSING FT size 65536
Total time 2 min, 56 sec
Figure 36:
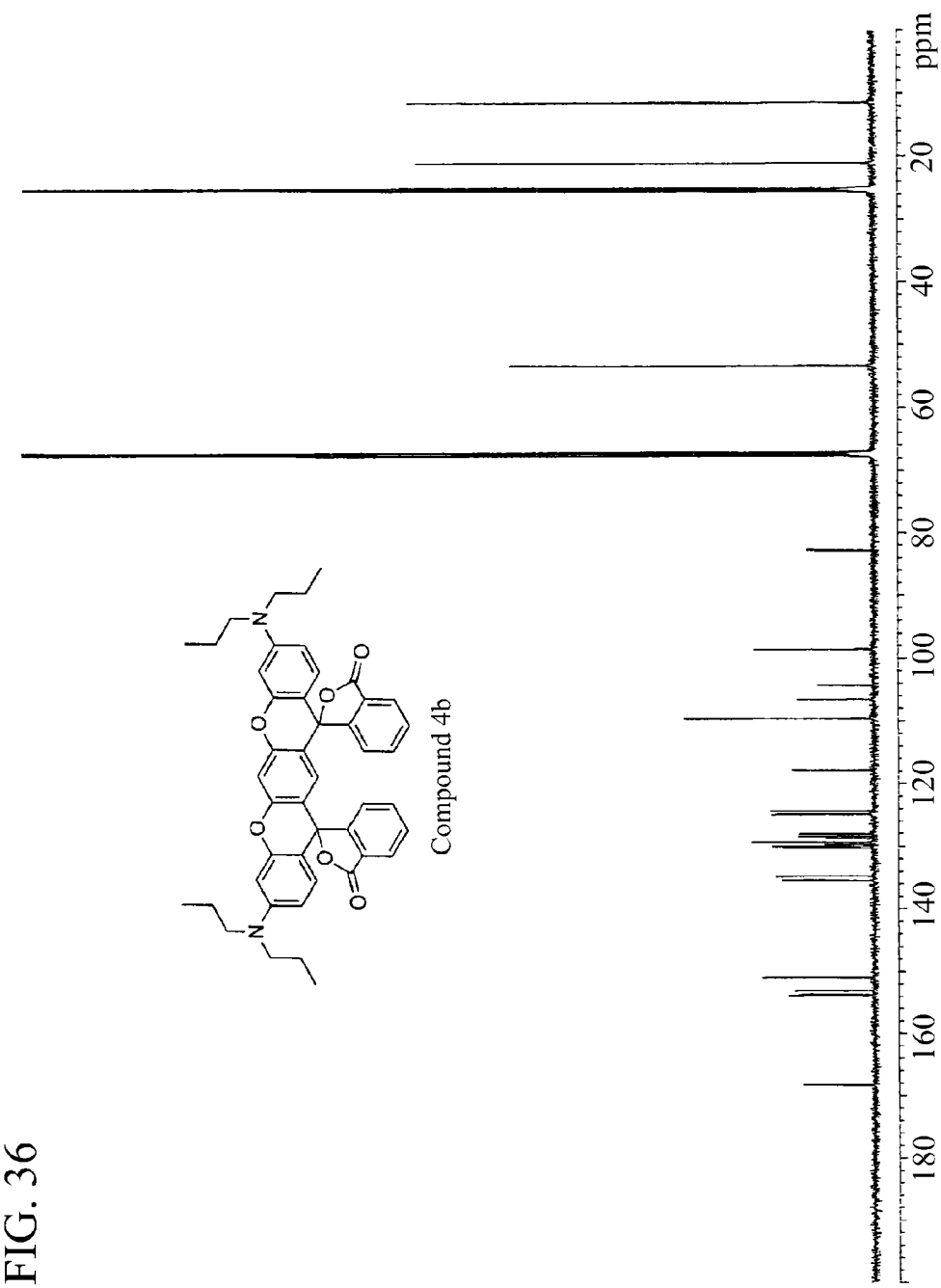
FIG. 36 shows NMR data of a compound "4b" (ABPX02). Additional data associated with FIG. 36 includes, but is not limited to:
OLM02
Pulse Sequence: s2 pul
  Solvent: Acetone
  Ambient temperature
INOVA-500 "inova1"
  Relax. delay 2.000 sec
  Pulse 45.0 degrees
  Acq. time 1.500 sec
  Width 31421.8 Hz
  1360 repetitions
OBSERVE C13, 125.6182194 MHz
DECOUPLE H1, 499.5777639 MHz
  Power 36 dB
  continuously on
  GARP-1 modulated
DATA PROCESSING
  Line broadening 1.0 Hz
FT size 131072
Total time 9 hr, 44 min, 49 sec
Figure 37:
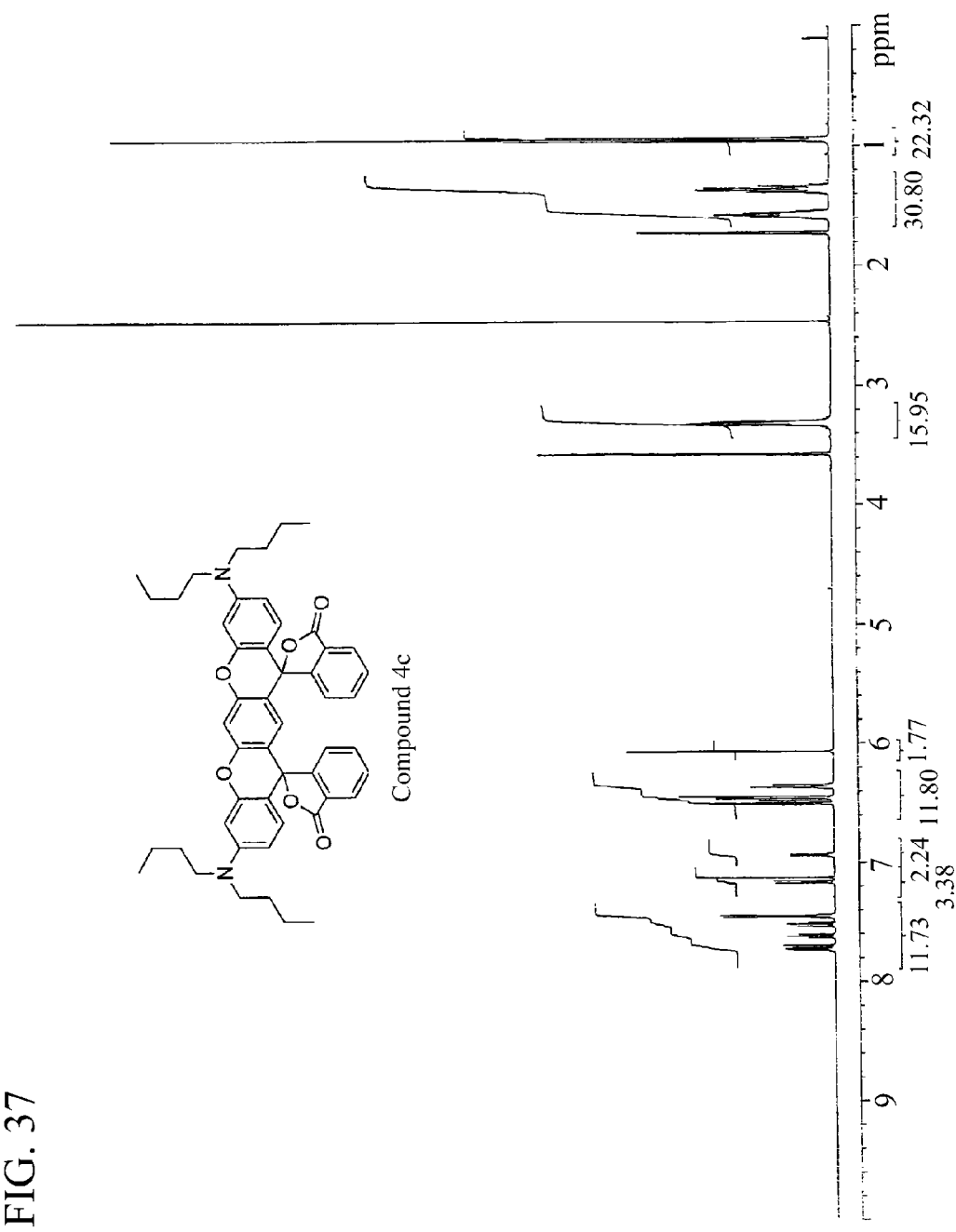
FIG. 37 shows NMR data of a compound "4c" (ABPX03). Additional data associated with FIG. 37 includes, but is not limited to:
OLM03
Pulse Sequence: s2 pul
  Solvent: Acetone
  Ambient temperature
INOVA-500 "inova1"
  Relax. delay 2.000 sec
  Pulse 45.0 degrees
  Acq. time 3.500 sec
  Width 7497.7 Hz
  32 repetitions
OBSERVE H1, 499.5754427 MHz
DATA PROCESSING
FT size 65536
Total time 2 min, 56 sec
Figure 38:
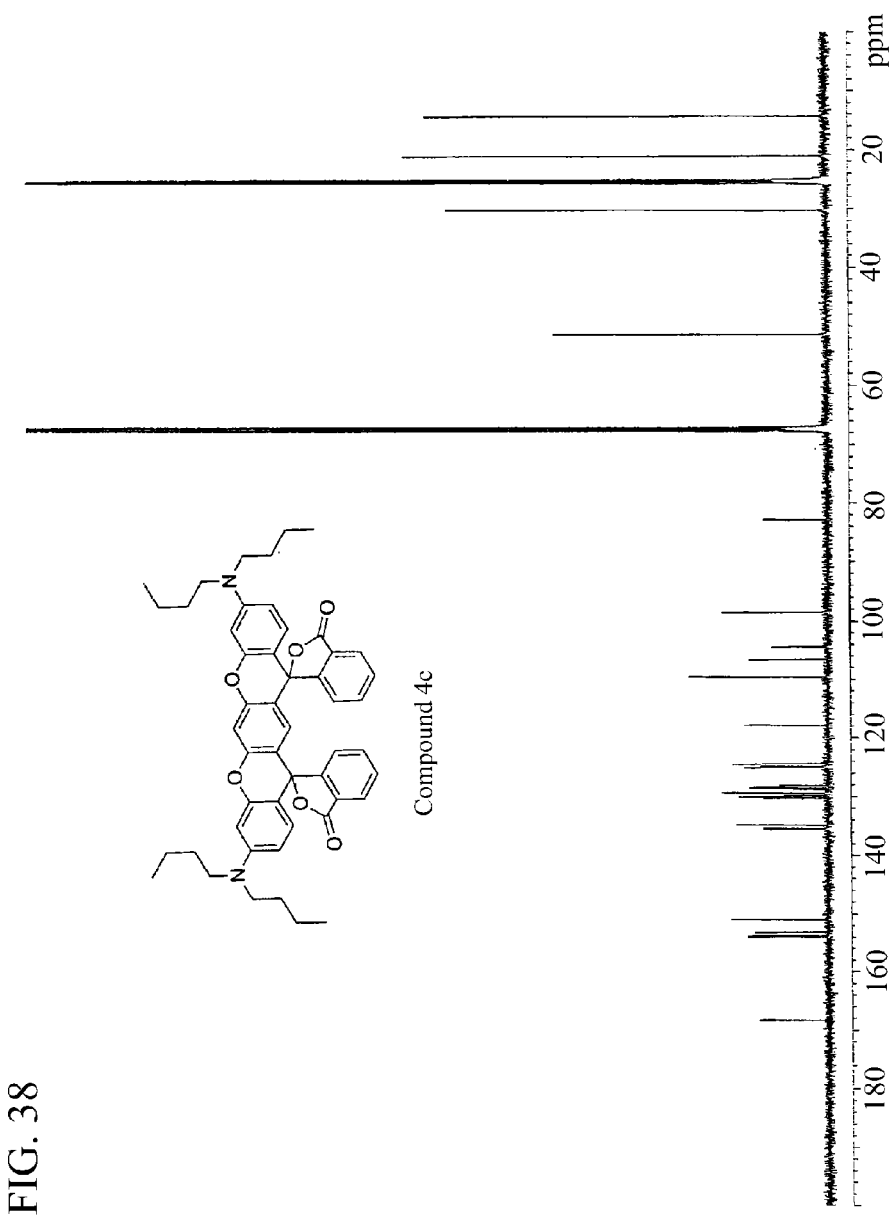
FIG. 38 shows NMR data of a compound "4c" (ABPX03). Additional data associated with FIG. 38 includes, but is not limited to:
OLM03
Pulse Sequence: s2 pul
  Solvent: Acetone
  Ambient temperature
INOVA-500 "inova1"
  Relax. delay 2.000 sec
  Pulse 45.0 degrees
  Acq. time 1.500 sec
  Width 31421.8 Hz
  2368 repetitions
OBSERVE C13, 125.6182194 MHz
DECOUPLE H1, 499.5777639 MHz
  Power 36 dB
  continuously on
  GARP-1 modulated
DATA PROCESSING
  Line broadening 1.0 Hz
FT size 131072
Total time 9 hr, 44 min, 49 sec
Figure 39:
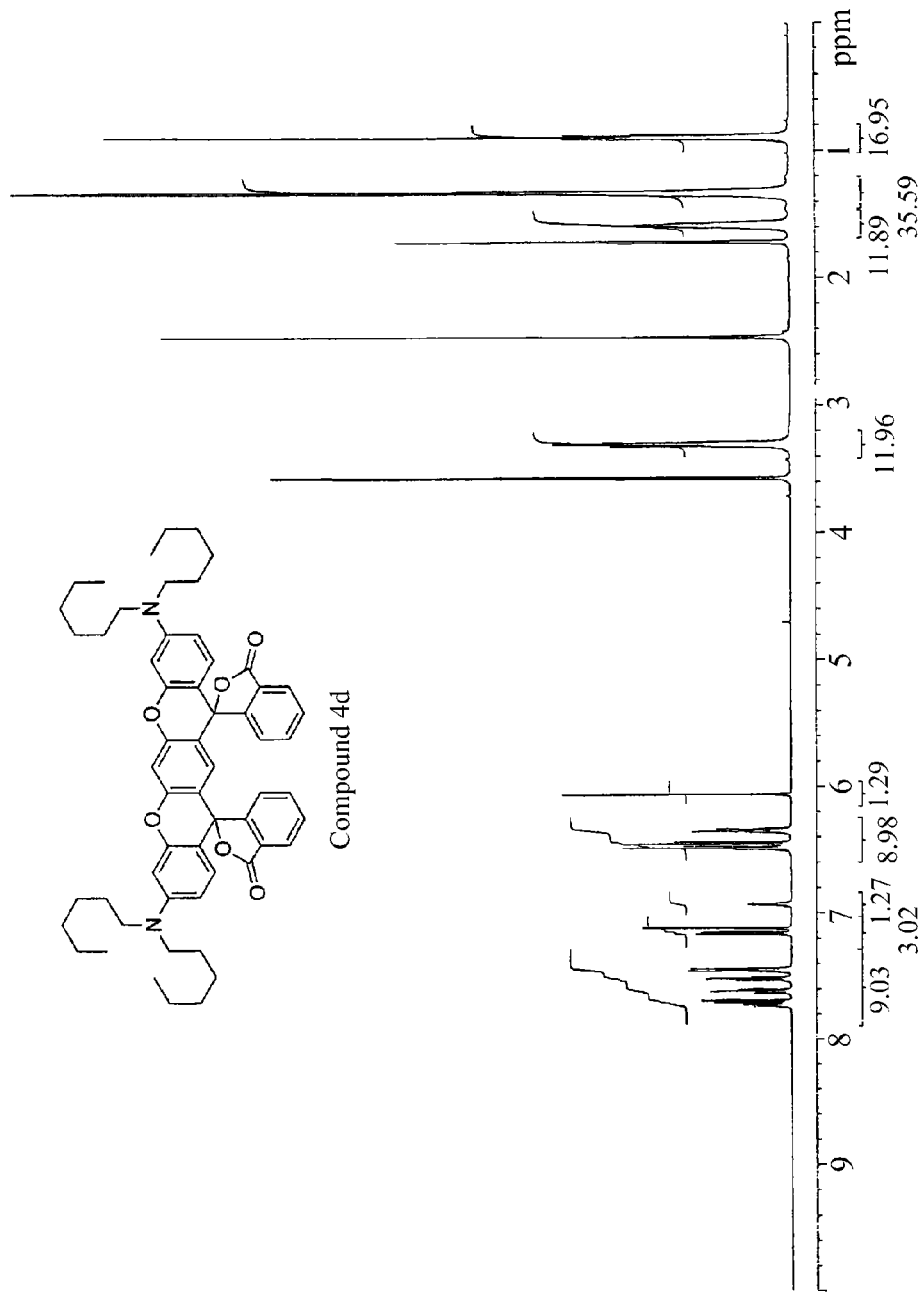
FIG. 39 shows NMR data of a compound "4d" (ABPX04). Additional data associated with FIG. 39 includes, but is not limited to:
OLM04
Pulse Sequence: s2 pul
  Solvent: Acetone
  Ambient temperature
INOVA-500 "inova1"
  Relax. delay 2.000 sec
  Pulse 45.0 degrees
  Acq. time 3.500 sec
  Width 7497.7 Hz
  16 repetitions
OBSERVE H1, 499.5754425 MHz
DATA PROCESSING
FT size 65536
Total time 1 min, 28 sec
Figure 40:
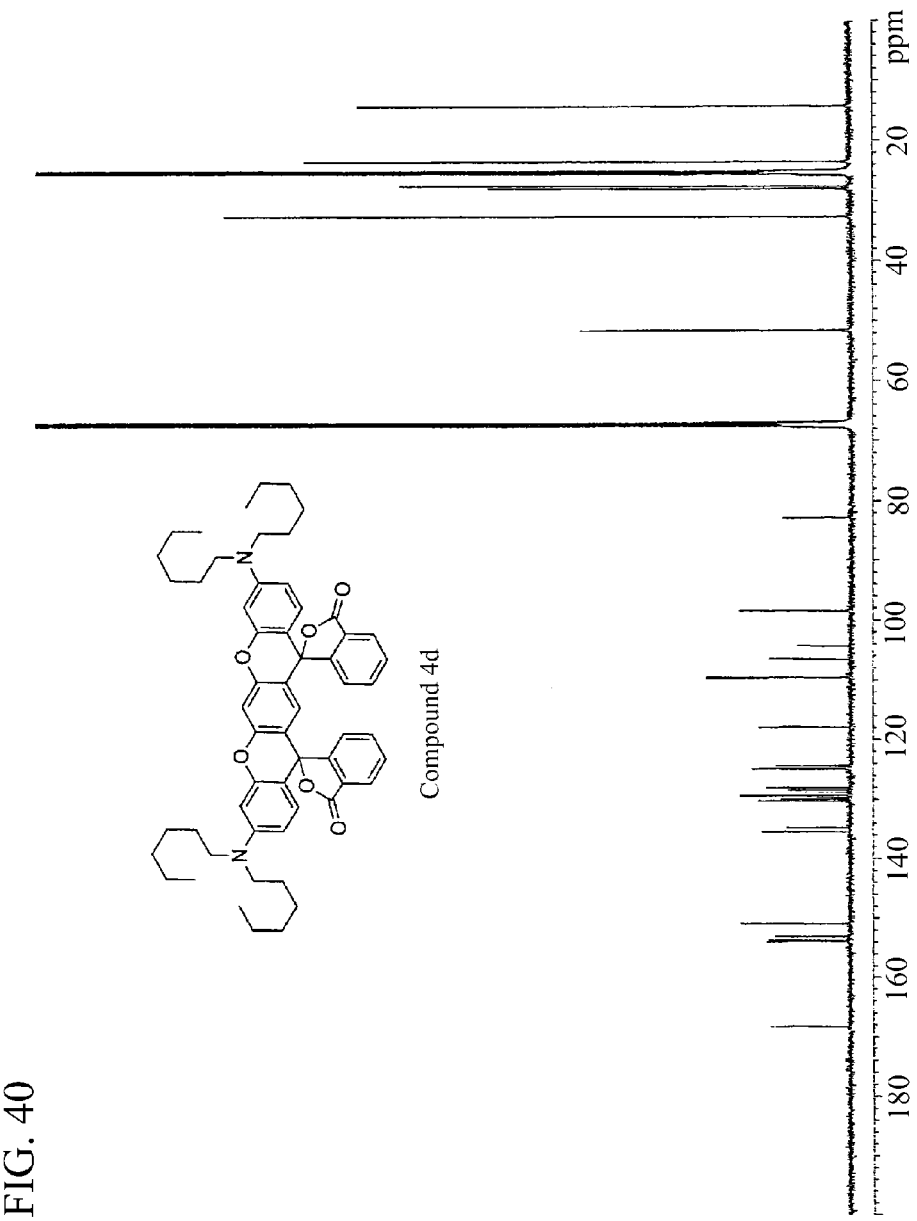
FIG. 40 shows NMR data of a compound "4d" (ABPX04). Additional data associated with FIG. 40 includes, but is not limited to:
OLM04
Pulse Sequence: s2 pul
  Solvent: Acetone
  Ambient temperature
INOVA-500 "inova1"
  Relax. delay 2.000 sec
  Pulse 45.0 degrees
  Acq. time 1.500 sec
  Width 31421.8 Hz
  10,000 repetitions
OBSERVE C13, 125.6182194 MHz
DECOUPLE H1, 499.5777639 MHz
  Power 36 dB
  continuously on
  GARP-1 modulated
DATA PROCESSING
  Line broadening 1.0 Hz
FT size 131072
Total time 9 hr, 44 min, 49 sec

In order to check whether or not restriction of intermolecular rotation (RIR) is involved in AIEE of ABPX01+, viscochromism and thermochromism of the ABPX01+ emission were examined. RIR was affected by the viscosity and temperature of the solvent. As the viscosity of the solvent (glycerol/methanol) increased or the temperature of methanol decreased, the emission exhibited by ABPX01+ increased (FIG. 16). ABPX01+ inhibited intramolecular rotation and induced AIEE at high viscosity and low temperature. These results indicate that RIR in ABPX01+ plays a crucial role in the emission enhancement in the aggregates states.

As such, novel rhodamine dyes (ABPX) were synthesized in Examples. ABPX can be feasibly synthesized by the condensation of individual benzophenone derivative with resorcinol. The emission behavior of ABPX was directly opposite to the concentration quenching of conventional rhodamine dyes. These results indicated that ABPX exhibited unique AIEE. The success of ABPX series is expected to lead to further technological applications in the fields of nano-biotechnology, photonics, and optoelectronics, and potential uses in photodynamic therapy.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

We claim:

1. A compound represented by the following formula (1) or (2):

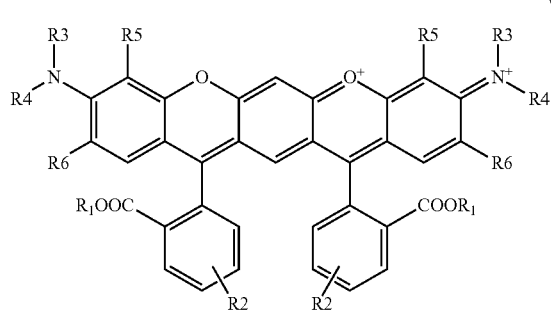

(1)

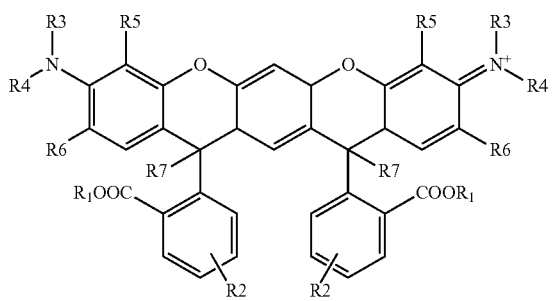

(2)

wherein in the formulae (1) and (2), each R1 independently represents a C1 to C8 alkyl group (which may have a nitrogen atom, an oxygen atom, or a sulfur atom as a heteroatom), or a hydrogen atom; each R2 independently represents a C1 to C8 alkyl group (which may have a nitrogen atom, an oxygen atom, or a sulfur atom as a heteroatom), a halogen atom, a nitro group, a carboxyl group, an amino group, or a hydrogen atom; each R3 and each R4 independently represent a C1 to C8 alkyl group (which may have a nitrogen atom, an oxygen atom, or a sulfur atom as a heteroatom), an allyl group, an aryl group, or a hydrogen atom; each R5 and each R6 independently represent a C1 to C8 alkyl group (which may have a nitrogen atom, an oxygen atom, or a sulfur atom as a heteroatom), an allyl group, a halogen atom, or a hydrogen atom; and R3 and R5, and/or R4 and R6 may be bound to each other to form a ring, and in the formula (2), each R7 independently represents a C1 to C8 alkyl group (which may have a nitrogen atom, an oxygen atom, or a sulfur atom as a heteroatom), an amino group, an amide group which may have a protective group or a substituent, a halogen atom, or a hydrogen atom; and R1 and R7 may be bound to each other to form a ring.

2. The compound as set forth in claim 1, represented by any one of the following formulae (3) to (22):

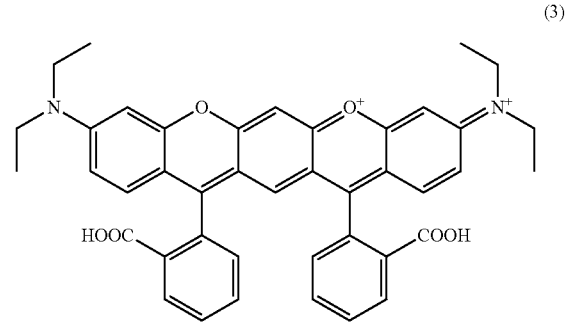

(3)

(4)
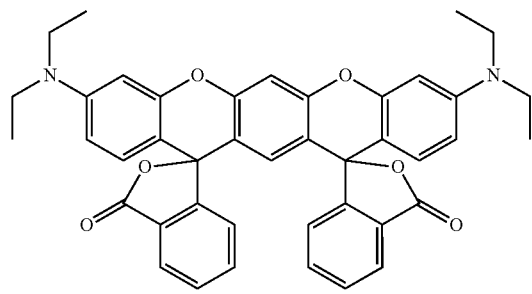
(5)
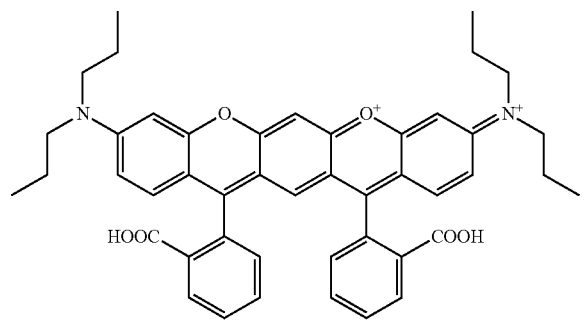
(6)
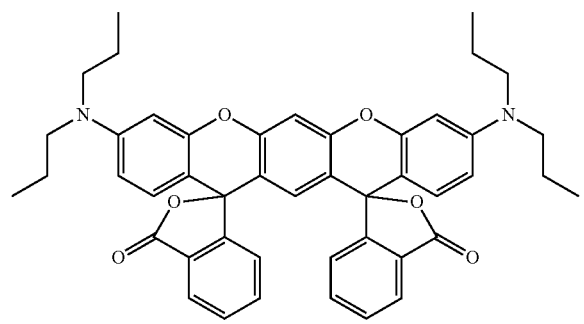
(7)
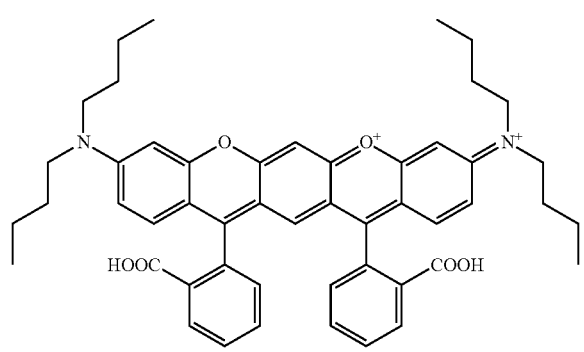
(8)
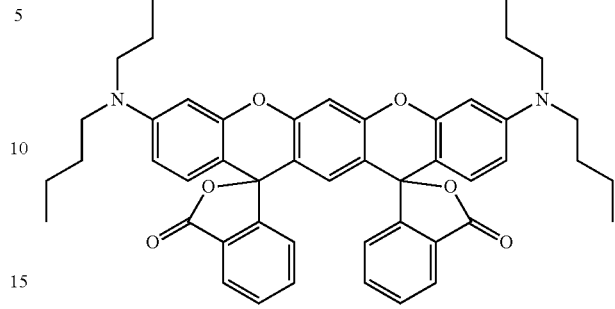
(9)
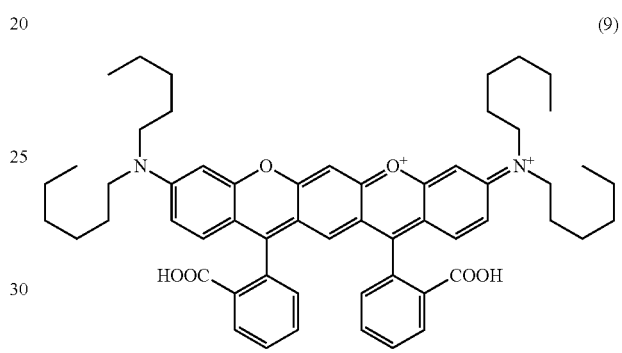
(10)
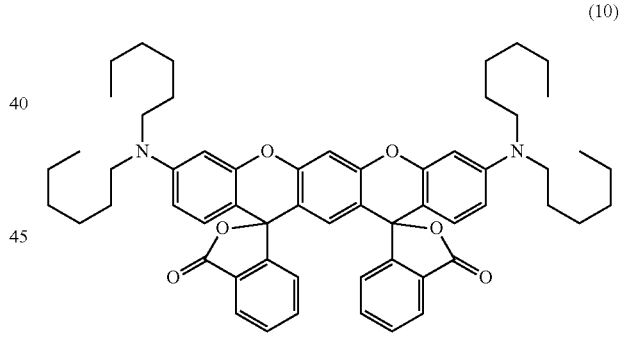
(11)
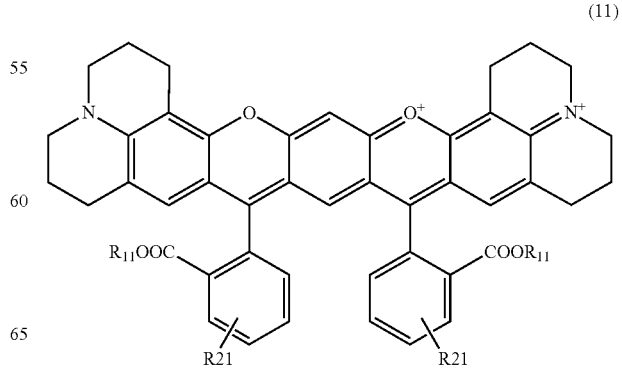

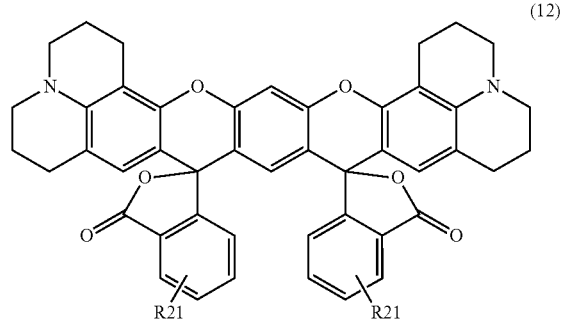
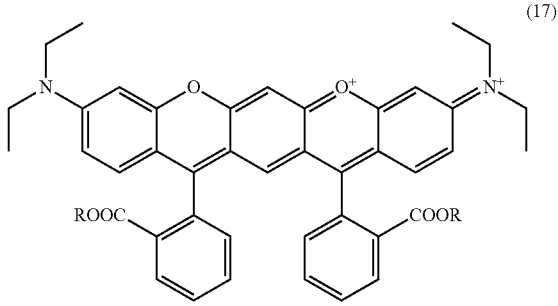
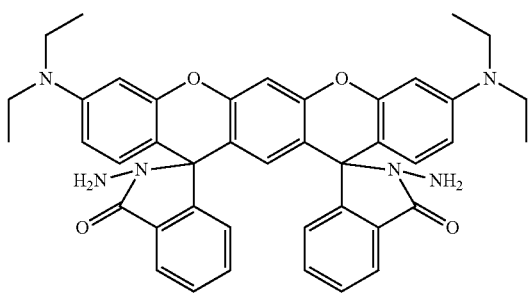
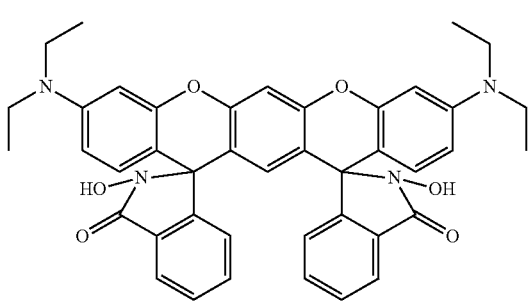
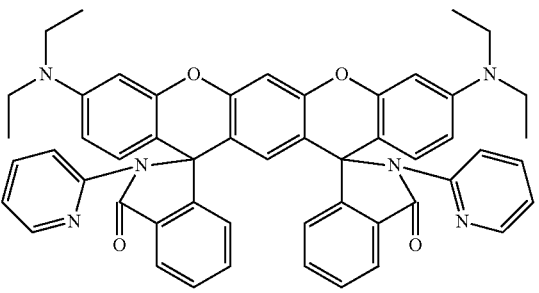

-continued (22)

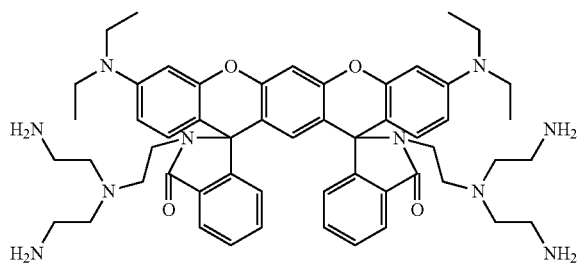

wherein each R and each R11 independently represent a C1 to C8 alkyl group (which may have a nitrogen atom, an oxygen atom, or a sulfur atom as a heteroatom) or a hydrogen atom; and each R21 independently represents a C1 to C8 alkyl group (which may have a nitrogen atom, an oxygen atom, or a sulfur atom as a heteroatom), a halogen atom, a nitro group, a carboxyl group, an amino group, or a hydrogen atom.

3. A method for producing a compound, comprising the step of carrying out a condensation process of condensing 2 equivalents of a benzophenone derivative and 1 equivalent of resorcinol in the presence of Lewis acid.

4. The method as set forth in claim 3, further comprising the steps of:
(a) adjusting a solution containing a reactant prepared in the condensation process so that the solution becomes basic;
(b) mixing the solution with an organic solvent to extract the reactant into an organic phase; and
(c) separating the reactant from the organic phase.

5. The method as set forth in claim 4, wherein:
the step (c) separates the reactant from the organic phase as a lactonoid form.

6. The method as set forth in claim 3, wherein:
the benzophenone derivative is a compound represented by the following formula (23):

(23)

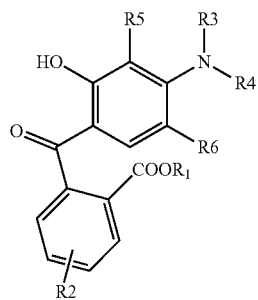

wherein R1 represents a C1 to C8 alkyl group (which may have a nitrogen atom, oxygen atom, or a sulfur atom as a heteroatom), or a hydrogen atom; R2 represents a C1 to C8 alkyl group (which may have a nitrogen atom, an oxygen atom, or a sulfur atom as a heteroatom), a halogen atom, a nitro group, a carboxyl group, an amino group, or a hydrogen atom; R3 and R4 each independently represent a C1 to C8 alkyl group (which may have a nitrogen atom, an oxygen atom, or a sulfur atom as a heteroatom), an allyl group, an aryl group, or a hydrogen atom; R5 and R6 each independently represent a C1 to C8 alkyl group (which may have a nitrogen atom, an oxygen atom, or a sulfur atom as a heteroatom), an allyl group, a halogen atom, or a hydrogen atom; and R3 and R5, and/or R4 and R6 may be bound to each other to form a ring.

7. A fluorescence emission method comprising the step of causing a compound as set forth in claim 1 to aggregate.

8. A quenching method for quenching emission of fluorescence, comprising the step of eliminating aggregation of a compound as set forth in claim 1.

9. A labeling kit comprising a compound as set forth in claim 1.

10. A labeling method for labeling, by use of a compound as set forth in claim 1, a biological molecule selected from the group consisting of antibodies, peptides, nucleotides, and sugars.

11. An analysis method for analyzing an aggregation mechanism of a target protein, which is labeled by a compound as set forth in claim 1, said method comprising the step of detecting emission of fluorescence.

12. A fluorescent probe comprising:
a biological molecule selected from the group consisting of antibodies, peptides, nucleotides, and sugars; and
a compound as set forth in claim 1.

13. A method for producing a fluorescent probe, said method comprising the step of labeling, by use of a compound as set forth in claim 1, a biological molecule selected from the group consisting of antibodies, peptides, nucleotides, and sugars.

14. A fluorescence imaging method comprising the step of visualizing a diseased portion by fluorescence by administering to a patient a fluorescent probe including a compound as set forth in claim 1 and a biological molecule selected from the group consisting of antibodies, peptides, nucleotides, and sugars.

15. The fluorescence imaging method as set forth in claim 14, wherein:
the biological molecule is a substance that recognizes cancer, and the disease is cancer.

16. A medicine for photodynamic therapy, comprising a compound as set forth in claim 1.

17. The medicine as set forth in claim 16, which is a medicine for treating cancer.

18. A method for treating cancer by photodynamic therapy by administering to a patient a compound as set forth in claim 1.

19. A dye-sensitized solar cell comprising a compound as set forth in claim 1 as a light-absorbing organic-dye material.

20. A light-emitting device comprising a compound as set forth in claim 1.

* * * * *